US012790298B2

(12) United States Patent
Hidber et al.

(10) Patent No.: US 12,790,298 B2
(45) Date of Patent: Nov. 10, 2026

(54) CRYSTALLINE POTASSIUM SALT OF 1-ETHYL-N-((1,2,3,5,6,7-HEXAHYDRO-S-INDACEN-4-YL)CARBAMOYL) PIPERIDINE-4-SULFONAMIDE

(71) Applicant: Hoffmann-La Roche Inc., Little Falls, NJ (US)

(72) Inventors: Pirmin Hidber, Seengen (CH); Dennis Dimo Enkelmann, Freiburg im Breisgau (DE); Marc Wermelinger, Kingersheim (FR)

(73) Assignee: Hoffman-La Roche Inc., Branchburg, NJ (US)

( * ) Notice: Subject to any disclaimer, the term of this patent is extended or adjusted under 35 U.S.C. 154(b) by 304 days.

(21) Appl. No.: 18/545,689

(22) Filed: Dec. 19, 2023

(65) Prior Publication Data

US 2024/0208904 A1 Jun. 27, 2024

Related U.S. Application Data

(63) Continuation of application No. PCT/EP2022/067278, filed on Jun. 23, 2022.

(30) Foreign Application Priority Data

Jun. 23, 2021 (EP) .................................... 21181211

(51) Int. Cl.
*C07D 211/54* (2006.01)

(52) U.S. Cl.
CPC .................................. *C07D 211/54* (2013.01)

(58) Field of Classification Search
CPC .................................................... C07D 211/54
See application file for complete search history.

(56) References Cited

U.S. PATENT DOCUMENTS 11,981,667 B2 * 5/2024 Cooper ................ C07D 211/54

FOREIGN PATENT DOCUMENTS

| | | | |
|---|---|---|---|
| JP | 2014189462 | A | 10/2006 |
| WO | 2016/131098 | A1 | 8/2016 |
| WO | 2019/008025 | A1 | 1/2019 |
| WO | 2001/51919 | A2 | 7/2019 |
| WO | 2011/115069 | A1 | 9/2022 |

OTHER PUBLICATIONS

Baldwin, A.G., et al., "Inhibiting the Inflammasome: A Chemical Perspective" J Med Chem 59(5):1691-1710 (Mar. 10, 2016).
"International Preliminary Report on Patentability—PCT/EP2022/067278" (Report Issuance Date: Dec. 14, 2023; Chapter I), :pp. 1-7 (Jan. 4, 2024).
"International Search Report—PCT/EP2022/067278" (w/Written Opinion), :pp. 1-13 (Sep. 30, 2022).
Lee, E.,, "A practical guide to pharmaceutical polymorph screening & selection" Asian J Pharma Sci 9(4):163-175 (Mar. 16, 2014).
Caira, M.R., Design of Organic Solids "Crystalline Polymorphism of Organic Compounds" Weber, E, Aoyama, Y, et al., eds., Berlin, Heidelberg-Germany: Springer, vol. 198:163-208 (1998).
Aaltonen et al., "Solid form screening—A review" European Journal of Pharmaceutics and Biopharmaceutics 71:23-37 ( 2009).
Byrn, S., et al., "Pharmaceutical Solids: A Strategic Approach to Regulatory Considerations" Pharmaceutical Res 12(7):945-954 (Jul. 1, 1995).
Hirayama Handbook for Producing Crystals of Organic Compounds (with English. Machine translation), Maruzen Co., Ltd,:57-84 (Jul. 25, 2008) With English Machine Translation.
Kawaguchi et al., "Pharmaceuticals and Crystal Polymorphs" Life Science and Technology Research 4(2):310-317 ( 2002) With English Machine Translation.
Kummerer, K., "Pharmaceuticals in the Environment" Ann Rev Environ Res 35:57- 75 (Nov. 1, 2010).
Lee E.H. et al., "A practical guide to pharmaceutical polymorph screening & selection" Asian Jour of Pharma Sci. 9(4):pp. 163-175 (Aug. 2014) https://doi.org/10.1016/j.ajps.2014.05.002.
Rodriguez-Spong et al., "General principles of pharmaceutical solid polymorphism: a supramolecular perspective" Adv Drug Delivery Rev 56:241-274 ( 2004).
Sarma et al., "olid formation of pharmaceuticals: Polymorphs, salt and cocrystals" Korean Journal of Chemical Engineering 28(2):315-322 (2011).
Variankaval et al., "From Form to Function: Crystallization of Active Pharmaceutical Ingredients" AIChE, 54(7):1682-1688 ( 2008).
Yamano et al., "Approach to Crystal Polymorphism Phenomenon in Pharmaceutical Process. Research" Journal of the Society of Synthetic Organic Chemistry 65(9):907-913 (Sep. 1, 2007) With English Machine Translation.

* cited by examiner

*Primary Examiner* — Timothy R Rozof
(74) *Attorney, Agent, or Firm* — Jelena Libby

(57) ABSTRACT

The present invention relates to a crystalline potassium salt of 1-ethyl-N-((1,2,3,5,6,7-hexahydro-s-indacen-4-yl)carbamoyl)piperidine-4-sulfonamide and to hydrates, solvates and polymorphic forms thereof. The present invention further relates to pharmaceutical compositions comprising this compound and the use of this compound in the treatment and prevention of medical diseases, disorders and conditions, most especially by NLRP3 inhibition.

21 Claims, 25 Drawing Sheets

CRYSTALLINE POTASSIUM SALT OF 1-ETHYL-N-((1,2,3,5,6,7-HEXAHYDRO-S-INDACEN-4-YL)CARBAMOYL) PIPERIDINE-4-SULFONAMIDE

CROSS-REFERENCE TO RELATED APPLICATIONS

This application is a continuation of International Application No. PCT/EP2022/067278, filed Jun. 23, 2022, which claims benefit of priority to European Application No. 21181211.0 filed Jun. 23, 2021, each of which is incorporated herein by reference in its entirety.

FIELD OF THE INVENTION

The present invention relates to a crystalline potassium salt of 1-ethyl-N-((1,2,3,5,6,7-hexahydro-s-indacen-4-yl) carbamoyl)piperidine-4-sulfonamide and to hydrates, solvates and polymorphic forms thereof. The present invention further relates to pharmaceutical compositions comprising this compound and the use of this compound in the treatment and prevention of medical diseases, disorders and conditions, most especially by NLRP3 inhibition.

BACKGROUND OF THE INVENTION

Several small molecules have been shown to inhibit the NLRP3 inflammasome. Glyburide inhibits IL-1β production at micromolar concentrations in response to the activation of NLRP3 but not NLRC4 or NLRP1. Other previously characterised weak NLRP3 inhibitors include parthenolide, 3,4-methylenedioxy-β-nitrostyrene and dimethyl sulfoxide (DMSO), although these agents have limited potency and are nonspecific.

Certain sulfonylurea-containing compounds are also disclosed as inhibitors of NLRP3 (see for example, Baldwin et al., J. Med. Chem., 59(5), 1691-1710, 2016; and WO 2016/131098 A1). WO 2019/008025 A1 discloses an amorphous potassium salt of 1-ethyl-N-((1,2,3,5,6,7-hexahydro-s-indacen-4-yl)carbamoyl)piperidine-4-sulfonamide.

There is a need to provide compounds with improved pharmacological and/or physiological and/or physicochemical properties and/or those that provide a useful alternative to known compounds.

SUMMARY OF THE INVENTION

A first aspect of the present invention provides a crystalline form of a potassium salt of 1-ethyl-N-((1,2,3,5,6,7-hexahydro-s-indacen-4-yl)carbamoyl)piperidine-4-sulfonamide, or a hydrate or solvate thereof.

A second aspect of the present invention provides a crystalline polymorphic form of a monopotassium salt of 1-ethyl-N-((1,2,3,5,6,7-hexahydro-s-indacen-4-yl)carbamoyl)piperidine-4-sulfonamide, or a hydrate or solvate thereof. Preferred examples of such polymorphs include the polymorphs referred to herein as Form A, Form D and Form B. Other examples of such polymorphs include the polymorphs referred to herein as Form C, Form E, Form F, Form G, Form H, Form I, Form J, Form K, Form L, Form M, and Form N.

A third aspect of the present invention provides a pharmaceutical composition comprising a crystalline form of the first aspect of the invention or a polymorphic form of the second aspect of the invention, and a pharmaceutically acceptable excipient.

Further aspects of the present invention provide medical uses and methods of treatment or prevention of a disease, disorder or condition, most especially by NLRP3 inhibition.

DETAILED DESCRIPTION OF THE INVENTION

Figure 1A:
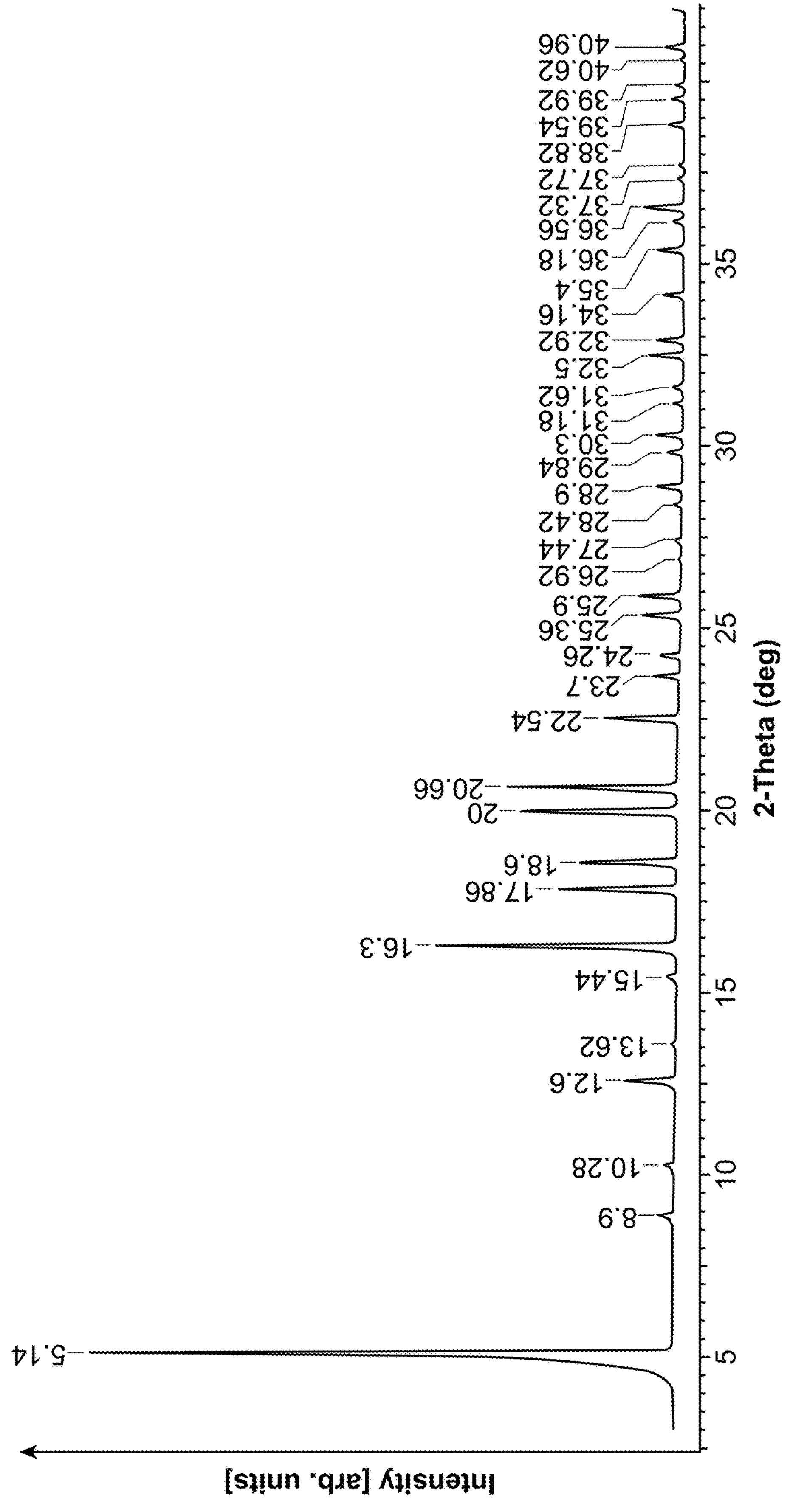
FIGS. 1A and 1B show an XRPD analysis of polymorphic Form A.

Differences between solid forms of an active pharmaceutical compound can have profound effects on the properties of the compound. For example, differences can arise in the crystallinity, solubility, intrinsic dissolution rate, bioavailability, stability to mechanical grinding, storage stability, and stability in aqueous and other media of a polymorphic form of a compound as compared to the amorphous and other polymorphic forms of the same compound.

The present invention provides a crystalline potassium salt of 1-ethyl-N-((1,2,3,5,6,7-hexahydro-s-indacen-4-yl) carbamoyl)piperidine-4-sulfonamide, or a hydrate or solvate thereof, which has certain advantages over the amorphous form. The present invention also provides polymorphs of the crystalline monopotassium salt of 1-ethyl-N-((1,2,3,5,6,7-hexahydro-s-indacen-4-yl)carbamoyl)piperidine-4-sulfonamide, or a hydrate or solvate thereof, which have certain advantages over other polymorphs and over the amorphous form.

A first aspect of the present invention provides a crystalline form of a potassium salt of 1-ethyl-N-((1,2,3,5,6,7-hexahydro-s-indacen-4-yl)carbamoyl)piperidine-4-sulfonamide, or a hydrate or solvate thereof. 1-Ethyl-N-((1,2,3,5, 6,7-hexahydro-s-indacen-4-yl)carbamoyl)piperidine-4-sulfonamide (also referred to as the free acid) has the formula:

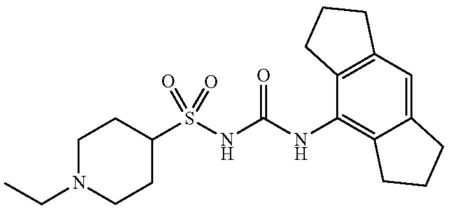 [SMILES: CCN1CCC(S(=O)(=O)NC(=O)Nc2c3c(cc4c2CCC4)CCC3)CC1]

The crystalline form of the first aspect of the present invention encompasses salts having any ratio of the conjugate base of the free acid to potassium ion, for example, the monopotassium salt, dipotassium salt and hemipotassium salt. In one embodiment, the crystalline potassium salt of 1-ethyl-N-((1,2,3,5,6,7-hexahydro-s-indacen-4-yl)carbamoyl)piperidine-4-sulfonamide is a monopotassium salt.

The crystalline form of the first aspect of the present invention may be anhydrous or in the form of a hydrate (e.g. a hemihydrate, monohydrate, dihydrate, trihydrate or non-stoichiometric hydrate) or other solvate. Such solvates may be formed with common organic solvents, including but not limited to alcoholic solvents e.g. methanol, ethanol or isopropanol. In one embodiment, the crystalline potassium salt of 1-ethyl-N-((1,2,3,5,6,7-hexahydro-s-indacen-4-yl)carbamoyl)piperidine-4-sulfonamide is an anhydrate. In one embodiment, the crystalline potassium salt of 1-ethyl-N-((1,2,3,5,6,7-hexahydro-s-indacen-4-yl)carbamoyl)piperidine-4-sulfonamide is a hydrate.

The crystalline form of the first aspect of the invention preferably has a degree of crystallinity of 50% or more (e.g. 60% or more, 70% or more, 80% or more, 90% or more, 95% or more, or 99% or more). As used herein a crystalline form of the first aspect of the invention is typically referred to as crystalline, if it has a degree of crystallinity of 90% or more (e.g. 95% or more, or 99% or more). As used herein the degree of crystallinity is the weight percentage of the crystalline form of the first aspect of the invention which is in one or more polymorphic forms, expressed as a percentage of the total weight of the salt. Typically the degree of crystallinity is determined by XRPD or DSC, preferably by XRPD.

The crystalline form of the first aspect of the invention preferably has a chemical purity as measured by HPLC of at least 95 wt %, more preferably at least 97 wt %, more preferably at least 98 wt %, more preferably at least 99 wt %, more preferably at least 99.5 wt %, even more preferably at least 99.8 wt %, and most preferably at least 99.9 wt %.

The crystalline form of the first aspect of the invention preferably has a chemical purity as measured by $^{1}H$ NMR of at least 95 wt %, more preferably at least 97 wt %, more preferably at least 98 wt %, more preferably at least 99 wt %, and more preferably at least 99.5 wt %.

In one embodiment, the crystalline potassium salt of 1-ethyl-N-((1,2,3,5,6,7-hexahydro-s-indacen-4-yl)carbamoyl)piperidine-4-sulfonamide is a crystalline monopotassium salt of 1-ethyl-N-((1,2,3,5,6,7-hexahydro-s-indacen-4-yl)carbamoyl)piperidine-4-sulfonamide anhydrate.

In one embodiment, the crystalline potassium salt of 1-ethyl-N-((1,2,3,5,6,7-hexahydro-s-indacen-4-yl)carbamoyl)piperidine-4-sulfonamide is a crystalline monopotassium salt of 1-ethyl-N-((1,2,3,5,6,7-hexahydro-s-indacen-4-yl)carbamoyl)piperidine-4-sulfonamide hydrate (e.g. a hemihydrate, monohydrate, dihydrate, trihydrate or non-stoichiometric hydrate).

A crystalline form of the first aspect of the invention may exist in one or more polymorphic forms. Polymorphism refers to the ability of a solid substance to exist in one or more distinct crystal structures (i.e. with one or more distinct arrangements of molecules relative to each other in the crystal lattice). Different polymorphs of a substance may have different physical properties such as bioavailability, solubility, intrinsic dissolution rate and calorimetric behaviour (e.g. melting point). Different polymorphs may also exhibit differences in stability (e.g. differences in stability with respect to conversion to other crystalline or amorphous forms or differences in stability to grinding). The physical properties of an active pharmaceutical ingredient may affect the drug product safety performance and efficacy. It is therefore advantageous to identify polymorphic forms of a drug substance which have pharmaceutically acceptable properties.

Accordingly, a second aspect of the present invention provides a crystalline polymorphic form of a monopotassium salt of 1-ethyl-N-((1,2,3,5,6,7-hexahydro-s-indacen-4-yl)carbamoyl)piperidine-4-sulfonamide, or a hydrate or solvate thereof.

The crystalline form of the first aspect of the invention and the polymorphic forms of the second aspect of the invention may contain any stable isotope including, but not limited to $^{12}C$, $^{13}C$, $^{1}H$, $^{2}H$ (D), $^{14}N$, $^{15}N$, $^{16}O$, $^{17}O$, $^{18}O$, $^{19}F$ and $^{127}I$, and any radioisotope including, but not limited to $^{11}C$, $^{14}C$, $^{3}H$ (T), $^{13}N$, $^{15}O$, $^{18}F$, $^{123}I$, $^{124}I$, $^{125}I$ and $^{131}I$.

A polymorphic form of the second aspect of the invention preferably comprises more than 80% of a single crystalline polymorph of the compound, preferably more than 90%, more preferably more than 95%, even more preferably more than 98%, and most preferably more than 99% as measured by XRPD or DSC, preferably as measured by XRPD.

In certain embodiments, the polymorphic form of the second aspect is a polymorph of 1-ethyl-N-((1,2,3,5,6,7-hexahydro-s-indacen-4-yl)carbamoyl)piperidine-4-sulfonamide monopotassium salt.

Preferred examples of polymorphic forms of the second aspect include the polymorphs referred to herein as Form A, Form D and Form B. Other examples of such polymorphs include the polymorphs referred to herein as Form C, Form E, Form F, Form G, Form H, Form I, Form J, Form K, Form L, Form M, and Form N.

The Form A to Form N polymorphs can be characterised by techniques including X-Ray Powder Diffraction (XRPD), Differential Scanning calorimetry (DSC), Thermogravimetric Analysis (TGA) and/or Thermogravimetric Analysis coupled to Fourier-Transform Infrared Spectroscopy (TGA-FTIR).

As used herein, XRPD data are typically those which can be obtained using CuKa1 radiation at 20° C. As used herein, the term "approximate" or "approximately" when used in connection with the position of an XRPD peak typically refers to the stated position ±0.2° 2θ, preferably ±0.15° 2θ. As used herein, DSC, TGA and TGA-FTIR data are typically those which can be obtained using a heating rate of 10 K/min, 5 K/min and 10 K/min respectively.

Form A Polymorph

The Form A polymorph is a first particularly preferred polymorphic form. It was the only anhydrous crystalline form identified. It was found to have good solubility and be thermodynamically stable as well as stable to prolonged grinding conditions. The Form A polymorph is therefore suitable for development as a drug product.

The Form A polymorph typically has an XRPD diffractogram comprising peaks at approximately: 5.14 °2θ, 16.30 °2θ, and 20.66 °2θ. More typically, the Form A polymorph has an XRPD diffractogram comprising peaks at approximately: 5.14 °2θ, 16.30 °2θ, 20.00 °2θ, and 20.66 °2θ. More typically, the Form A polymorph has an XRPD diffractogram comprising peaks at approximately: 5.14 °2θ, 16.30 °2θ, 20.66 °2θ, and 22.54 °2θ. More typically, the Form A polymorph has an XRPD diffractogram comprising peaks at approximately: 5.14 °2θ, 16.30 °2θ, 17.86 °2θ, 20.00 °2θ, and 20.66 °2θ. Still more typically, the Form A polymorph has an XRPD diffractogram comprising peaks at approximately: 5.14 °2θ, 16.30 °2θ, 17.86 °2θ, 18.60 °2θ, 20.00 °2θ, 20.66 °2θ, and 22.54 ° 2θ. Still further typically, the Form A polymorph has an XRPD diffractogram comprising peaks at approximately: 5.14 °2θ, 12.60 °2θ, 16.30 °2θ, 17.86 °2θ, 18.60 °2θ, 20.00 °2θ, 20.66 °2θ, 22.54 °2θ, 25.36 °2θ, and 25.90 °2θ. Still further typically, the Form A polymorph has an XRPD diffractogram comprising peaks at approximately: 5.14 °2θ, 12.60 °2θ, 16.30 °2θ, 17.86 °2θ, 18.60 °2θ, 20.00 °2θ, 20.66 °2θ, 22.54 °2θ, 23.70 °2θ, 25.36 °2θ, 25.90 °2θ, 32.50 °2θ, and 36.56 °2θ. Still further typically, the Form A polymorph has an XRPD diffractogram comprising peaks at approximately: 5.14 °2θ, 8.90 °2θ, 12.60 °2θ, 16.30 °2θ, 17.86 °2θ, 18.60 °2θ, 20.00 °2θ, 20.66 °2θ, 22.54 °2θ, 23.70 °2θ, 24.26 °2θ, 25.36 °2θ, 25.90 °2θ, 28.90 °2θ, 30.30 °2θ, 32.50 °2θ, 32.92 °2θ, 35.40 °2θ, and 36.56 °2θ.

The Form A polymorph typically has an XRPD diffractogram in which the 10 most intense peaks include 5 or more (e.g. 6 or more, 7 or more, 8 or more, 9 or more, or 10) peaks which have an approximate 2θ value selected from: 5.14 °2θ, 8.90 °2θ, 12.60 °2θ, 16.30 °2θ, 17.86 °2θ, 18.60 °2θ, 20.00 °2θ, 20.66 °2θ, 22.54 °2θ, 23.70 °2θ, 24.26 °2θ, 25.36 °2θ, 25.90 °2θ, 28.90 °2θ, 30.30 °2θ, 32.50 °2θ, 32.92 °2θ, 35.40 °2θ, and 36.56 °2θ. More typically, the Form A polymorph has an XRPD diffractogram in which the 10 most intense peaks include 5 or more (e.g. 6 or more, 7 or more, 8 or more, 9 or more, or 10) peaks which have an approximate 2θ value selected from: 5.14 °2θ, 12.60 °2θ, 16.30 °2θ, 17.86 °2θ, 18.60 °2θ, 20.00 °2θ, 20.66 °2θ, 22.54 °2θ, 23.70 °2θ, 25.36 °2θ, 25.90 °2θ, 32.50 °2θ, and 36.56 °2θ. Still more typically, the Form A polymorph has an XRPD diffractogram in which the 10 most intense peaks include 5 or more (e.g. 6 or more, 7 or more, 8 or more, 9 or more, or 10) peaks which have an approximate 2θ value selected from: 5.14 °2θ, 12.60 °2θ, 16.30 °2θ, 17.86 °2θ, 18.60 °2θ, 20.00 °2θ, 20.66 °2θ, 22.54 °2θ, 25.36 °2θ, and 25.90 °2θ.

The Form A polymorph may have an XRPD diffractogram approximately as set out in Table 1 below:

TABLE 1

| Form A | |
|---|---|
| Angle/°2θ | Intensity % |
| 5.14 | 100 |
| 8.90 | 5 |
| 10.28 | 4 |
| 12.60 | 11 |
| 13.62 | 3 |
| 15.44 | 4 |
| 16.30 | 42 |
| 17.86 | 22 |
| 18.60 | 18 |
| 20.00 | 28 |
| 20.66 | 31 |
| 22.54 | 14 |
| 23.70 | 6 |
| 24.26 | 5 |
| 25.36 | 8 |
| 25.90 | 8 |
| 26.92 | 2 |
| 27.44 | 2 |
| 28.42 | 2 |
| 28.90 | 5 |
| 29.84 | 4 |
| 30.30 | 5 |
| 31.18 | 3 |
| 31.62 | 3 |
| 32.50 | 7 |
| 32.92 | 5 |
| 34.16 | 4 |
| 35.40 | 5 |
| 36.18 | 3 |
| 36.56 | 7 |
| 37.32 | 2 |
| 37.72 | 2 |
| 38.82 | 3 |
| 39.54 | 3 |
| 39.92 | 2 |
| 40.62 | 1 |
| 40.96 | 4 |

Figure 1B:
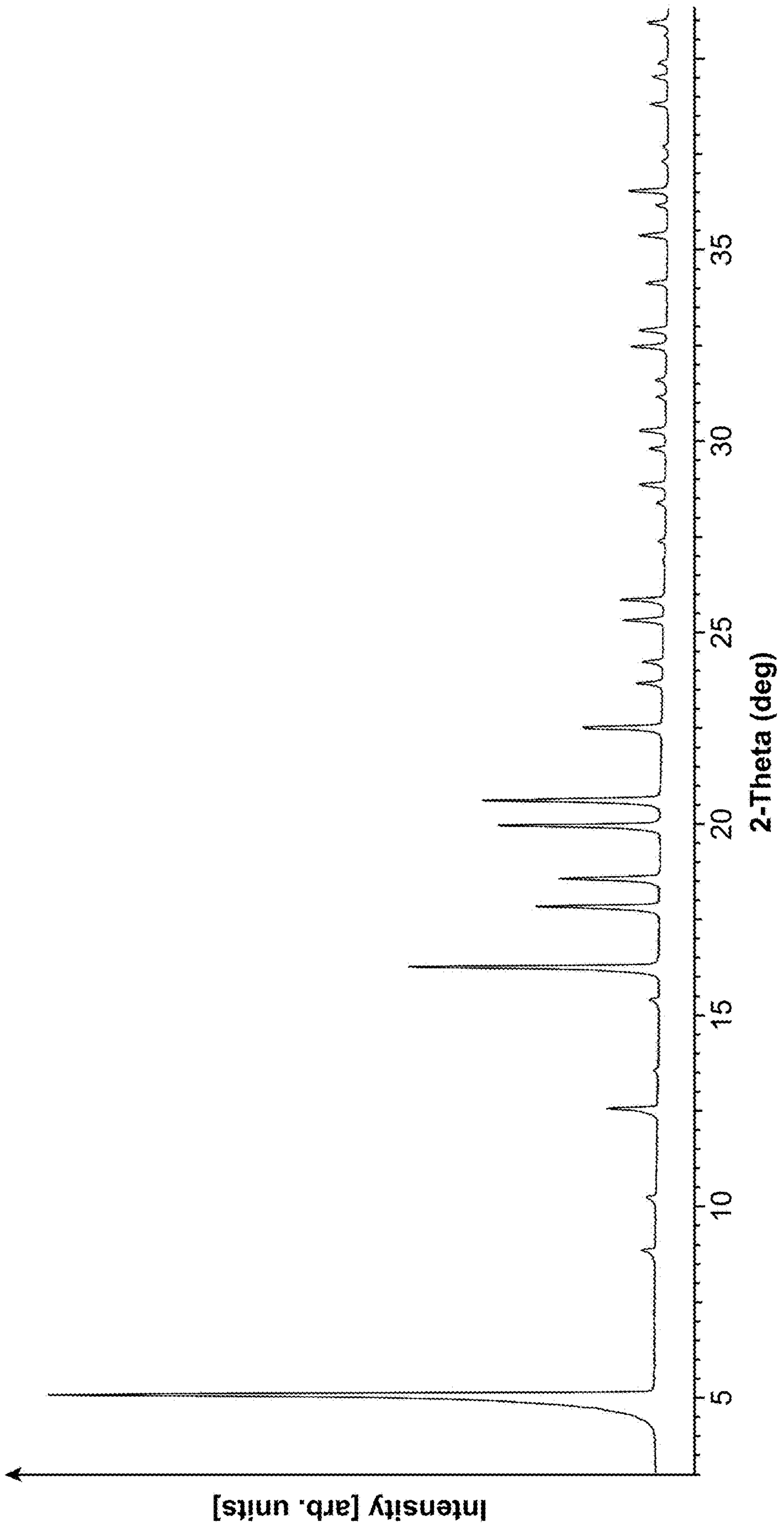

The Form A polymorph may have an XRPD diffractogram approximately as set out in FIG. 1A or 1B.

The Form A polymorph is an anhydrous polymorphic form. The Form A polymorph was the only anhydrous crystalline form identified.

The Form A polymorph is also hygroscopic and can contain varying amounts of non-assimilated water (i.e. not water of hydration). The amount of non-assimilated water depends on the preparation and storage conditions used. Amounts of up to about 3% of non-assimilated water have been observed for the Form A polymorph. When stored at ambient conditions (about 20-40% RH (typically about 30% RH) and about 20-25° C.), Form A polymorph typically contains from about 1% to about 1.5% non-assimilated water.

The Form A polymorph typically has a TGA profile comprising weight loss of up to about 3% (typically up to about 2.5%, typically up to about 2%) between 25° C. and 210° C.

Figure 2:
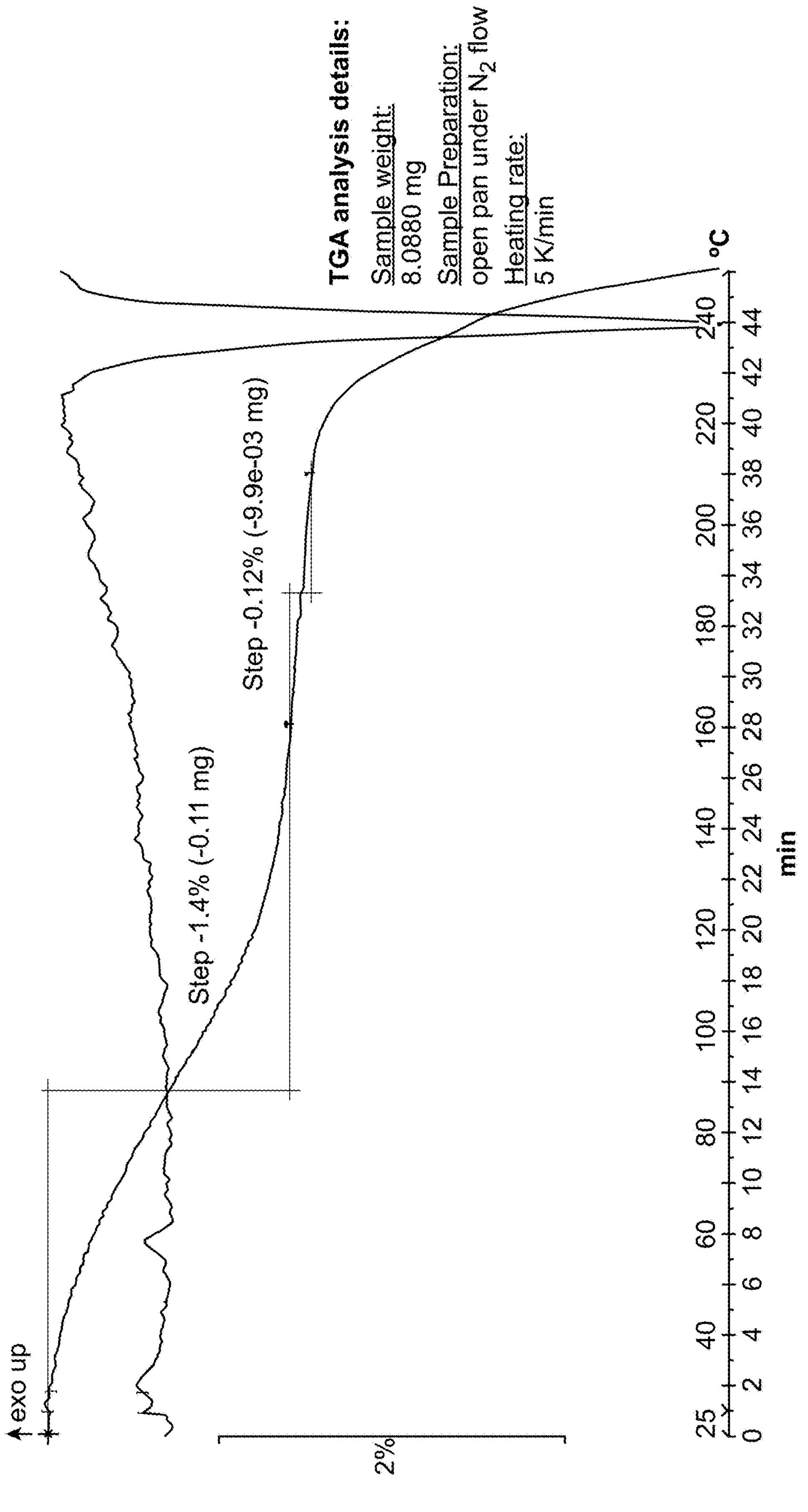
FIG. 2 shows a TGA analysis of polymorphic Form A.

The Form A polymorph may have a TGA profile approximately as set out in FIG. 2.

The Form A polymorph typically has a DSC profile comprising a single endothermic event, which is believed to be melting with decomposition. The endothermic event of the Form A polymorph typically has an onset at a temperature in a range from about 227° C. to about 247° C. (e.g. a temperature in a range from about 232° C. to about 242° C., a temperature in a range from about 233° C. to about 241° C., or at a temperature of about 237° C.). The endothermic event of the Form A polymorph typically has a peak at a temperature in a range from about 233° C. to about 253° C. (e.g. a temperature in a range from about 238° C. to about 248° C., a temperature in a range from about 239° C. to about 247° C., or at a temperature of about 243° C.).

Figure 3:
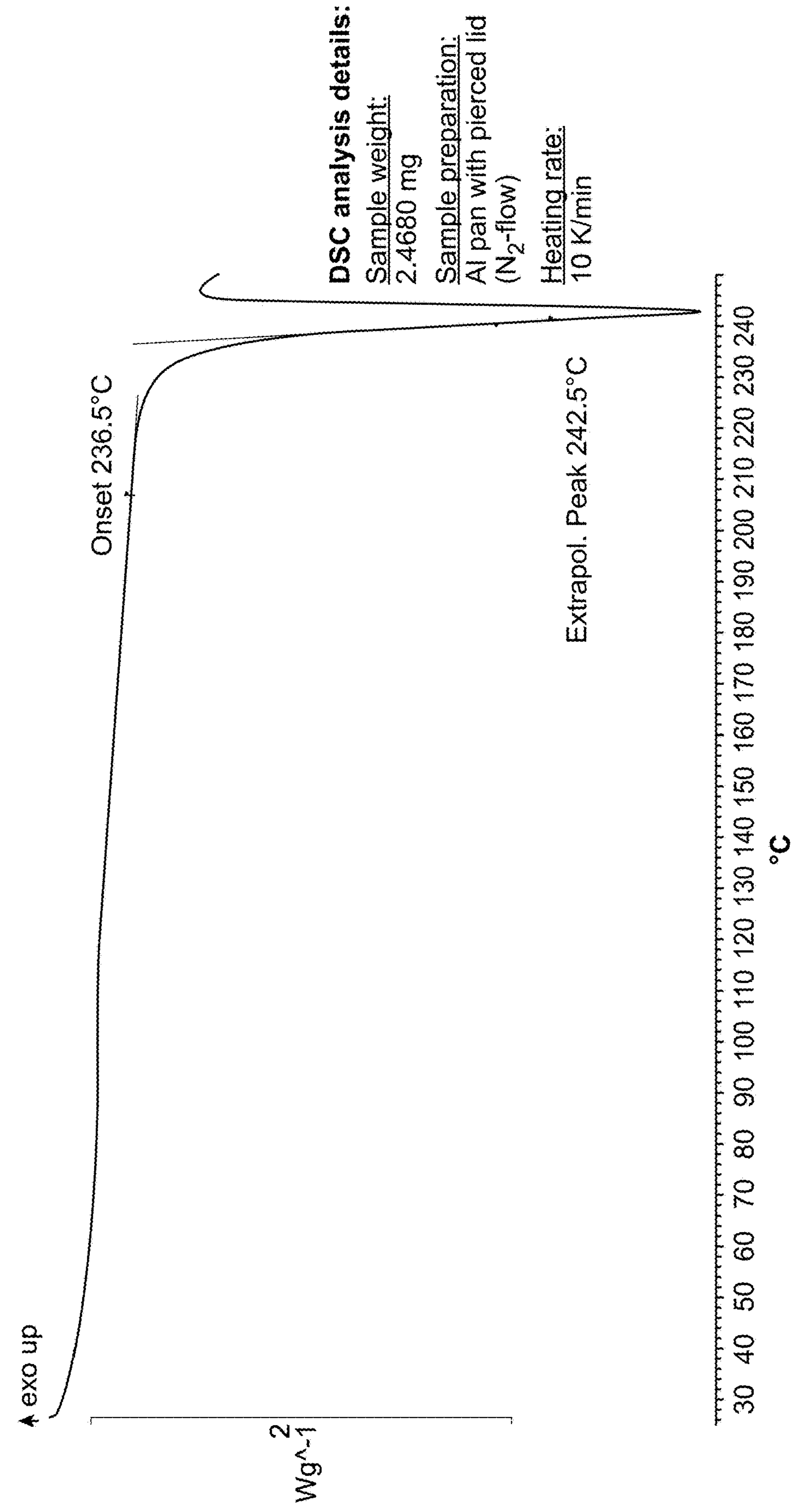
FIG. 3 shows a DSC analysis of polymorphic Form A.

The Form A polymorph may have a DSC profile approximately as set out in FIG. 3.

The Form A polymorph may be obtained by a process comprising:

(a) suspending 1-ethyl-N-((1,2,3,5,6,7-hexahydro-s-indacen-4-yl)carbamoyl)piperidine-4-sulfonamide monopotassium salt in a solvent system to form a suspension; and (b) obtaining a crystalline monopotassium salt of 1-ethyl-N-((1,2,3,5,6,7-hexahydro-s-indacen-4-yl)carbamoyl) piperidine-4-sulfonamide as the Form A polymorph from the suspension.

In a preferred embodiment, the solvent system used in step (a) comprises a solvent selected from acetone, methylethyl ketone, acetonitrile, propionitrile, tert-butyl methyl ether, methyl acetate, ethyl acetate, isopropyl acetate, 2-methyl tetrahydrofuran, nitromethane, toluene, anisole, chlorobenzene, and mixtures thereof. In a preferred embodiment, the solvent system used in step (a) consists of a solvent selected from acetone, methylethyl ketone, acetonitrile, propionitrile, tert-butyl methyl ether, methyl acetate, ethyl acetate, isopropyl acetate, 2-methyl tetrahydrofuran, nitromethane, toluene, anisole, chlorobenzene, and mixtures thereof. In a preferred embodiment, the solvent system used in step (a) comprises a solvent selected from acetone, acetonitrile, and mixtures thereof. In a preferred embodiment, the solvent system used in step (a) consists of a solvent selected from acetone, acetonitrile, and mixtures thereof. In a preferred embodiment, the solvent system consists of acetone or acetonitrile.

In some embodiments, step (a) is carried out at a temperature in a range of 5° C. to 60° C., or a range of 10° C. to 30° C., or a range of 15° C. to 25° C.

Form D Polymorph

The Form D polymorph is a second particularly preferred polymorphic form. It was found to have good solubility and be stable in the presence of water, either as solvent or co-solvent or humidity (such as >30% RH at 25° C.). The Form D polymorph is therefore also suitable for development as a drug product.

The Form D polymorph typically has an XRPD diffractogram comprising peaks at approximately: 4.86 °2θ, 9.74 °2θ, 16.08 °2θ, and 19.16 °2θ. More typically, the Form D polymorph has an XRPD diffractogram comprising peaks at approximately: 4.86 °2θ, 8.42 °2θ, 9.74 °2θ, 16.08 °2θ, and 19.16 °2θ. More typically, the Form D polymorph has an XRPD diffractogram comprising peaks at approximately: 4.86 °2θ, 9.74 °2θ, 16.08 °2θ, 16.94 °2θ, and 19.16 °2θ. More typically, the Form D polymorph has an XRPD diffractogram comprising peaks at approximately: 4.86 °2θ, 9.74 °2θ, 14.64 °2θ, 16.08 °2θ, 19.16 °2θ, and 19.46 °2θ. Still more typically, the Form D polymorph has an XRPD diffractogram comprising peaks at approximately: 4.86 °2θ, 9.74 °2θ, 14.64 °2θ, 16.08 °2θ, 16.94 °2θ, 17.62 °2θ, 19.16 °2θ, 19.46° 2θ, and 20.98 °2θ. Still further typically, the Form D polymorph has an XRPD diffractogram comprising peaks at approximately: 4.86 °2θ, 8.42 °2θ, 9.74 °2θ, 12.76 °2θ, 14.64 °2θ, 16.08 °2θ, 16.94 °2θ, 17.62 °2θ, 19.16 °2θ, 19.46 °2θ, 20.06 °2θ, and 20.98 °2θ.

The Form D polymorph typically has an XRPD diffractogram in which the 10 most intense peaks include 5 or more (e.g. 6 or more, 7 or more, 8 or more, 9 or more, or 10) peaks which have an approximate 2θ value selected from: 4.86 °2θ, 8.42 °2θ, 9.74 °2θ, 12.76 °2θ, 14.64 °2θ, 16.08 °2θ, 16.94 °2θ, 17.62 °2θ, 19.16 °2θ, 19.46 °2θ, 20.06 °2θ, 20.98 °2θ, 24.52° 2θ, and 29.56 °2θ. More typically, the Form D polymorph has an XRPD diffractogram in which the 10 most intense peaks include 5 or more (e.g. 6 or more, 7 or more, 8 or more, 9 or more, or 10) peaks which have an approximate 2θ value selected from: 4.86 °2θ, 8.42 °2θ, 9.74 °2θ, 12.76 °2θ, 14.64 °2θ, 16.08 °2θ, 16.94 °2θ, 17.62 °2θ, 19.16 °2θ, 19.46 °2θ, 20.06 °2θ, and 20.98 °2θ. Still more typically, the Form D polymorph has an XRPD diffractogram in which the 10 most intense peaks include 5 or more (e.g. 6 or more, 7 or more, 8 or more, 9 or more, or 10) peaks which have an approximate 2θ value selected from: 4.86 °2θ, 9.74 °2θ, 14.64 °2θ, 16.08 °2θ, 16.94 °2θ, 17.62 °2θ, 19.16 °2θ, 19.46 °2θ, 20.06 °2θ, and 20.98 °2θ.

The Form D polymorph may have an XRPD diffractogram approximately as set out in Table 2 below:

TABLE 2

| Form D | |
|---|---|
| Angle/°2θ | Intensity % |
| 4.86 | 100 |
| 8.42 | 5 |
| 9.74 | 13 |
| 12.76 | 5 |
| 14.64 | 7 |
| 16.08 | 12 |
| 16.94 | 6 |
| 17.62 | 6 |
| 19.16 | 19 |
| 19.46 | 8 |
| 20.06 | 5 |
| 20.98 | 6 |
| 24.52 | 4 |
| 27.36 | 3 |
| 27.76 | 3 |
| 29.08 | 2 |
| 29.56 | 3 |
| 31.12 | 3 |

Figure 4A:
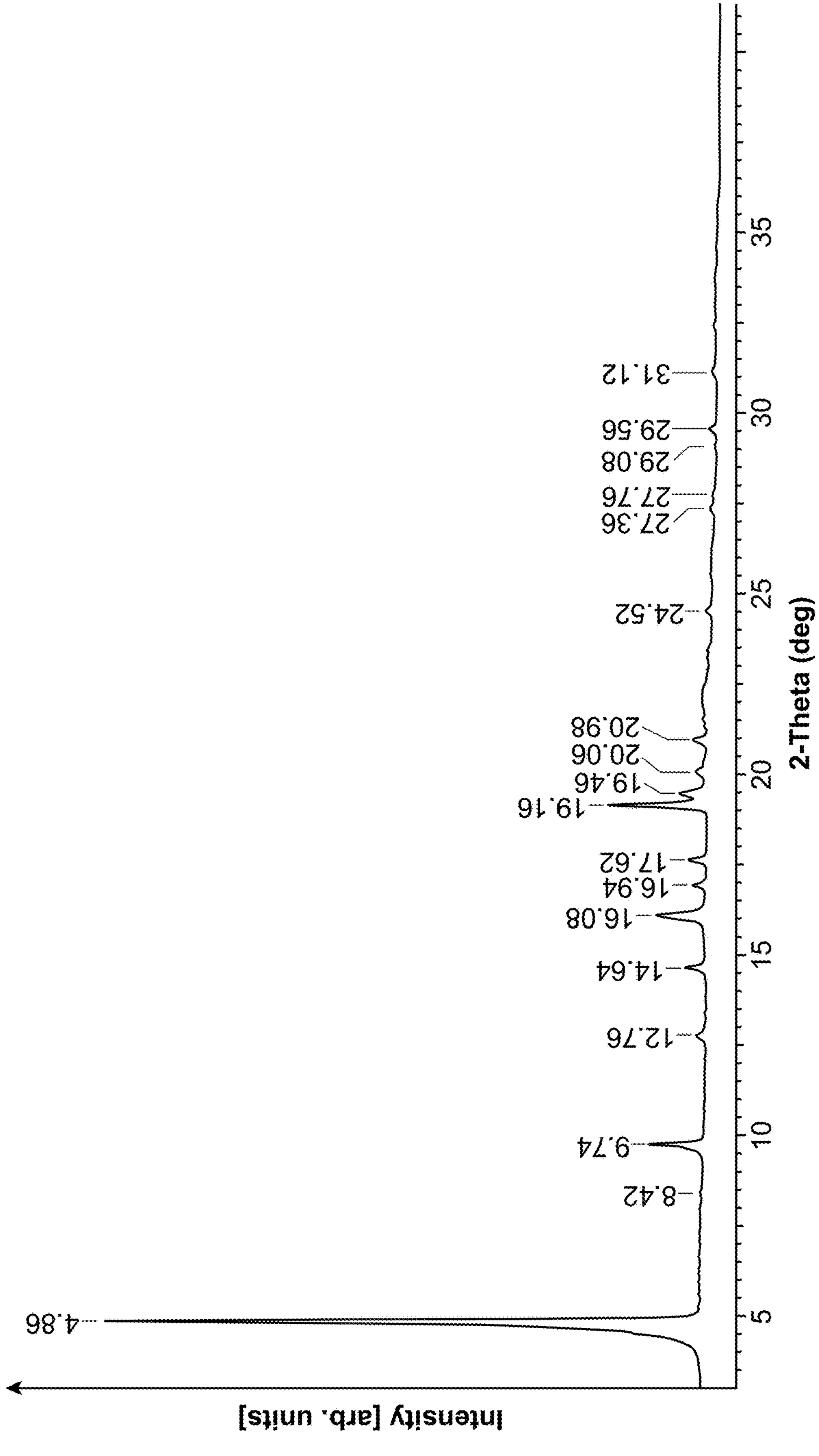
FIGS. 4A and 4B show an XRPD analysis of polymorphic Form D.
Figure 4B:
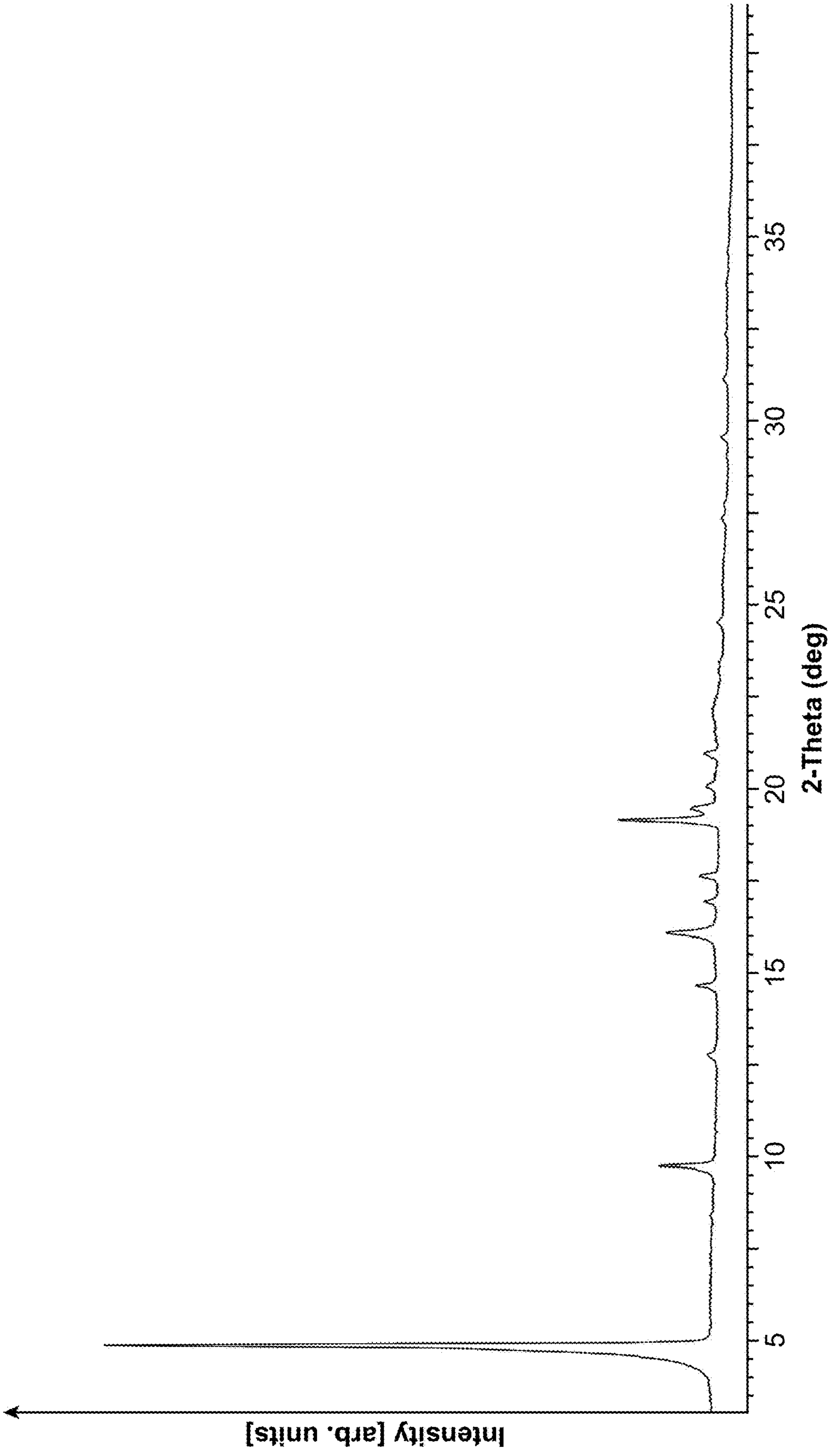

The Form D polymorph may have an XRPD diffractogram approximately as set out in FIG. 4A or 4B.

The Form D polymorph is a hydrate. It contains between about 4% and about 8% water. When stored at ambient conditions (about 20-40% RH (typically about 30% RH) and about 20-25° C.), Form D polymorph typically contains from about 6% to about 7% water (about 1.5 mol to about 1.8 mol per mol 1-ethyl-N-((1,2,3,5,6,7-hexahydro-s-indacen-4-yl)carbamoyl)piperidine-4-sulfonamide monopotassium).

The Form D polymorph typically has a TGA profile comprising weight loss of about 4.3% to about 8.3% (e.g. weight loss of about 5.3% to about 7.3%, weight loss of about 5.8% to about 6.8%, weight loss of about 6.1% to about 6.5%, or weight loss of about 6.3%) between 25° C. and 160° C.

Figure 5:
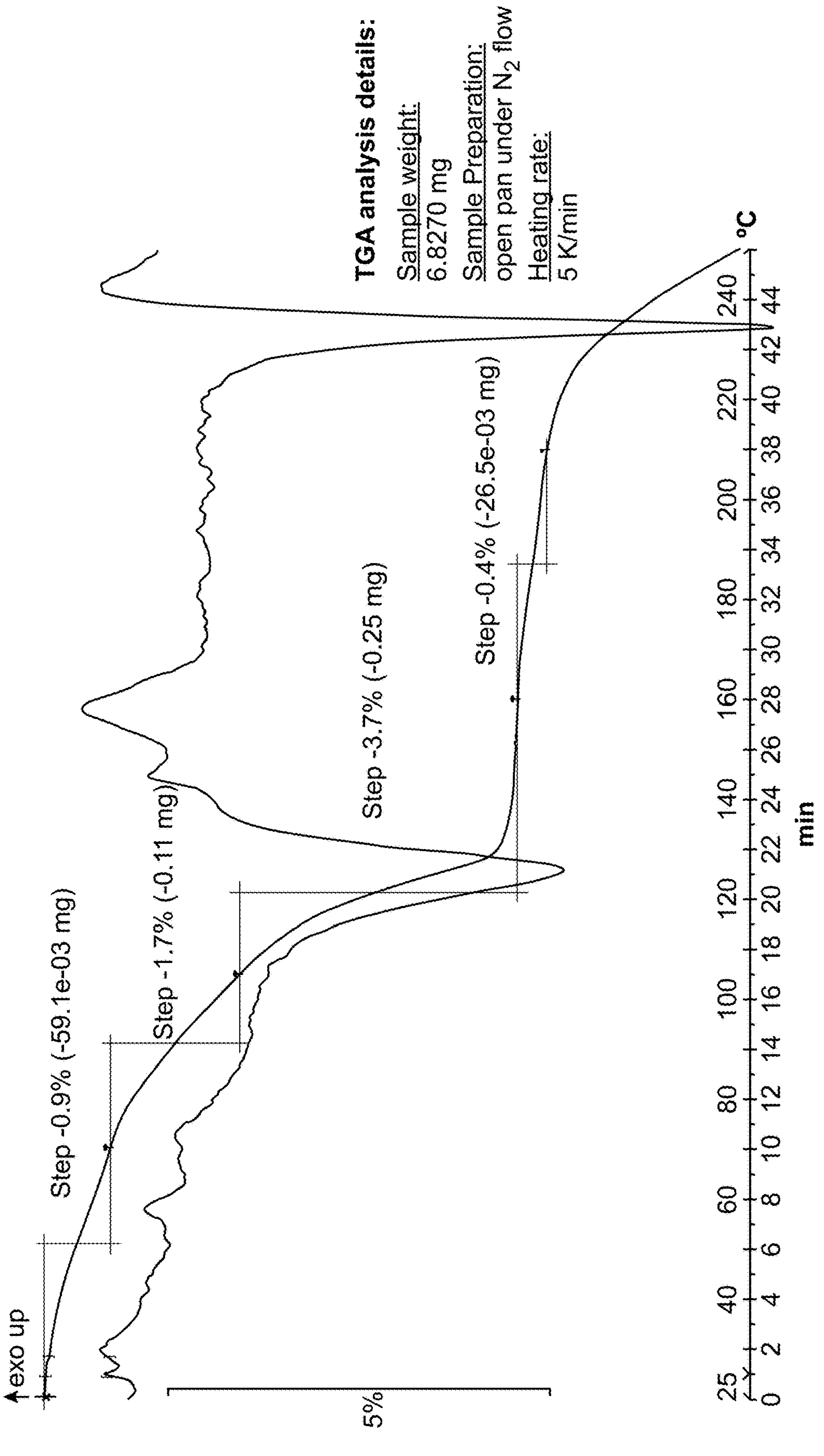
FIG. 5 shows a TGA analysis of polymorphic Form D.

The Form D polymorph may have a TGA profile approximately as set out in FIG. 5.

The Form D polymorph typically has a DSC profile comprising a first endothermic event (which is believed to be loss of water of hydration), an exothermic event (which is believed to be phase transformation to Form A polymorph), and a second endothermic event (which is believed to be melting with decomposition).

The first endothermic event of the Form D polymorph is a broad endothermic event occurring from about 25° C. to about 138° C.

The exothermic event of the Form D polymorph typically has a first onset at a temperature in a range from about 137° C. to about 157° C. (e.g. a temperature in a range from about 142° C. to about 152° C., a temperature in a range from about 143° C. to about 151° C., or at a temperature of about 147° C.) and a second onset at a temperature in a range from about 141° C. to about 161° C. (e.g. a temperature in a range from about 146° C. to about 156° C., a temperature in a range from about 147° C. to about 155° C., or at a temperature of about 151° C.). The exothermic event of the Form D polymorph typically has a first peak at a temperature in a range from about 140° C. to about 160° C. (e.g. a temperature in a range from about 145° C. to about 155° C., a temperature in a range from about 146° C. to about 154° C., or at a temperature of about 150° C.) and a second peak at a temperature in a range from about 152° C. to about 172° C. (e.g. a temperature in a range from about 157° C. to about 167° C., a temperature in a range from about 158° C. to about 166° C., or at a temperature of about 162° C.).

The second endothermic event of the Form D polymorph typically has an onset at a temperature in a range from about 223° C. to about 243° C. (e.g. a temperature in a range from about 228° C. to about 238° C., a temperature in a range from about 229° C. to about 237° C., or at a temperature of about 233° C.). The second endothermic event of the Form D polymorph typically has a peak at a temperature in a range from about 229° C. to about 249° C. (e.g. a temperature in a range from about 234° C. to about 244° C., a temperature in a range from about 235° C. to about 243° C., or at a temperature of about 239° C.

Figure 6:
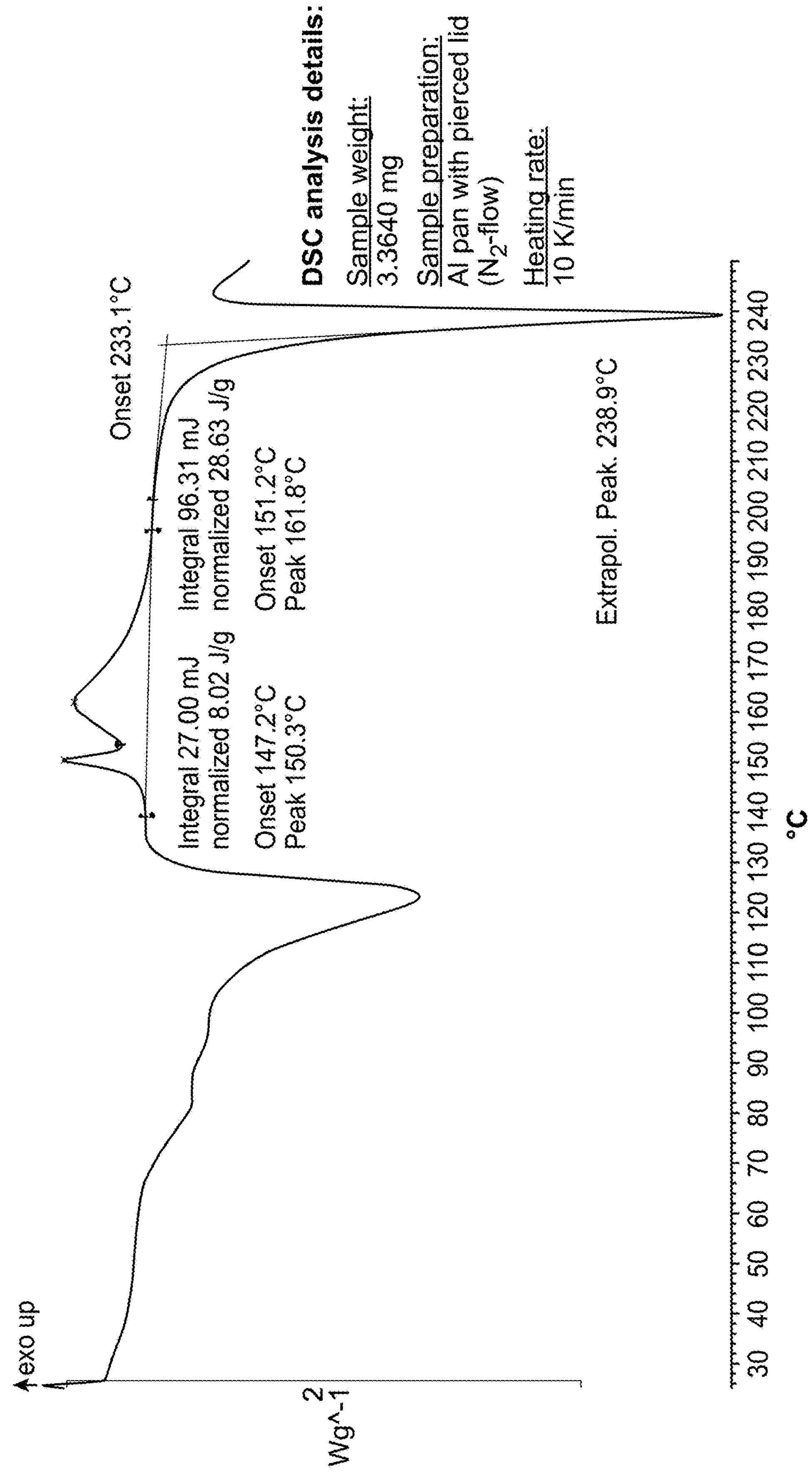
FIG. 6 shows a DSC analysis of polymorphic Form D.

The Form D polymorph may have a DSC profile approximately as set out in FIG. 6.

The Form D polymorph may be obtained by a process comprising:

(a) suspending 1-ethyl-N-((1,2,3,5,6,7-hexahydro-s-indacen-4-yl)carbamoyl)piperidine-4-sulfonamide monopotassium salt in a solvent system comprising methylethyl ketone, tetrahydrofuran, acetone or a mixture thereof to form a suspension;

(b) adding water to the suspension to dissolve the 1-ethyl-N-((1,2,3,5,6,7-hexahydro-s-indacen-4-yl)carbamoyl) piperidine-4-sulfonamide monopotassium salt to form a solution; and (c) obtaining a crystalline monopotassium salt of 1-ethyl-N-((1,2,3,5,6,7-hexahydro-s-indacen-4-yl)carbamoyl) piperidine-4-sulfonamide as the Form D polymorph from the solution.

In a preferred embodiment, the solvent system used in step (a) comprises methylethyl ketone. In a preferred embodiment, the solvent system used in step (a) consists of methylethyl ketone.

In a preferred embodiment, the volume ratio of the solvent system of step (a) to the water of step (b) is from 100:1 to 1:1 (e.g. from 40:1 to 1:1, or about 12.5:1).

In a preferred embodiment, in step (b), the suspension is heated to form a solution and, in step (c), the solution is cooled (e.g. to room temperature or to about 20-25° C.) to obtain the Form D polymorph from the solution.

Form B Polymorph

The Form B polymorph typically has an XRPD diffractogram comprising peaks at approximately: 4.90 °2θ, 6.60 °2θ, and 7.06 °2θ. More typically, the Form B polymorph has an XRPD diffractogram comprising peaks at approximately: 4.90 °2θ, 6.60 °2θ, 7.06 °2θ, and 13.28 °2θ. More typically, the Form B polymorph has an XRPD diffractogram comprising peaks at approximately: 4.90 °2θ, 6.60 °2θ, 7.06 °2θ, and 18.58 °2θ. More typically, the Form B polymorph has an XRPD diffractogram comprising peaks at approximately: 4.90 °2θ, 6.60 °2θ, 7.06 °2θ, 13.06 °2θ, 13.28 °2θ, and 18.58 °2θ. Still more typically, the Form B polymorph has an XRPD diffractogram comprising peaks at approximately: 4.90 °2θ, 6.60 °2θ, 7.06 °2θ, 11.64 °2θ, 13.06 °2θ, 13.28 °2θ, 18.58 °2θ, 20.36 ° 2θ, and 21.36 °2θ. Still further typically, the Form B polymorph has an XRPD diffractogram comprising peaks at approximately: 4.58 °2θ, 4.90 °2θ, 6.60 °2θ, 7.06 °2θ, 11.64 °2θ, 13.06 °2θ, 13.28 °2θ, 17.98 °2θ, 18.58 °2θ, 18.74 °2θ, 20.36 °2θ, and 21.36 °2θ. Still further typically, the Form B polymorph has an XRPD diffractogram comprising peaks at approximately: 4.58 °2θ, 4.90 °2θ, 6.60 °2θ, 7.06 °2θ, 9.26 °2θ, 9.84 °2θ, 11.64 °2θ, 13.06 °2θ, 13.28 °2θ, 14.16 °2θ, 16.32 °2θ, 17.24 °2θ, 17.98 °2θ, 18.58 °2θ, 18.74 °2θ, 19.78 °2θ, 20.36 °2θ, and 21.36 °2θ.

The Form B polymorph typically has an XRPD diffractogram in which the 10 most intense peaks include 5 or more (e.g. 6 or more, 7 or more, 8 or more, 9 or more, or 10) peaks which have an approximate 2θ value selected from: 4.58 °2θ, 4.90 °2θ, 6.60 °2θ, 7.06 °2θ, 9.26 °2θ, 9.84 °2θ, 11.64 °2θ, 13.06 °2θ, 13.28 °2θ, 14.16 °2θ, 16.32 °2θ, 17.24 °2θ, 17.98 °2θ, 18.58 °2θ, 18.74 °2θ, 19.78 °2θ, 20.36 °2θ, and 21.36 °2θ. More typically, the Form B polymorph has an XRPD diffractogram in which the 10 most intense peaks include 5 or more (e.g. 6 or more, 7 or more, 8 or more, 9 or more, or 10) peaks which have an approximate 2θ value selected from: 4.58 °2θ, 4.90 °2θ, 6.60 °2θ, 7.06 °2θ, 11.64 °2θ, 13.06 °2θ, 13.28 °2θ, 17.98 °2θ, 18.58 °2θ, 18.74 °2θ, 20.36 °2θ, and 21.36 °2θ. Still more typically, the Form B polymorph has an XRPD diffractogram in which the 10 most intense peaks include 5 or more (e.g. 6 or more, 7 or more, 8 or more, 9 or more, or 10) peaks which have an approximate 2θ value selected from: 4.58 °2θ, 4.90 °2θ, 6.60 °2θ, 7.06 °2θ, 11.64 °2θ, 13.06 °2θ, 13.28 °2θ, 18.58 °2θ, 20.36 °2θ, and 21.36 °2θ.

The Form B polymorph may have an XRPD diffractogram approximately as set out in Table 3 below:

TABLE 3

| Form B | |
|---|---|
| Angle/°2θ | Intensity % |
| 4.58 | 9 |
| 4.90 | 100 |
| 6.60 | 21 |
| 7.06 | 32 |
| 9.26 | 7 |
| 9.84 | 7 |
| 10.20 | 5 |
| 11.64 | 11 |
| 13.06 | 13 |
| 13.28 | 13 |
| 14.16 | 7 |
| 14.44 | 5 |
| 14.52 | 5 |
| 14.88 | 4 |
| 15.18 | 4 |
| 15.60 | 4 |
| 16.32 | 7 |
| 17.24 | 7 |
| 17.46 | 5 |
| 17.98 | 9 |
| 18.58 | 14 |
| 18.74 | 9 |
| 19.00 | 5 |
| 19.20 | 5 |
| 19.50 | 5 |
| 19.78 | 8 |
| 20.36 | 10 |
| 20.70 | 5 |
| 21.16 | 5 |
| 21.36 | 10 |
| 22.02 | 6 |

TABLE 3-continued

| Form B | |
|---|---|
| Angle/°2θ | Intensity % |
| 22.98 | 6 |
| 23.46 | 5 |
| 24.04 | 5 |
| 24.64 | 5 |
| 25.04 | 6 |
| 25.86 | 3 |
| 26.20 | 3 |
| 26.84 | 3 |
| 27.30 | 4 |
| 28.58 | 5 |
| 28.78 | 5 |

Figure 7A:
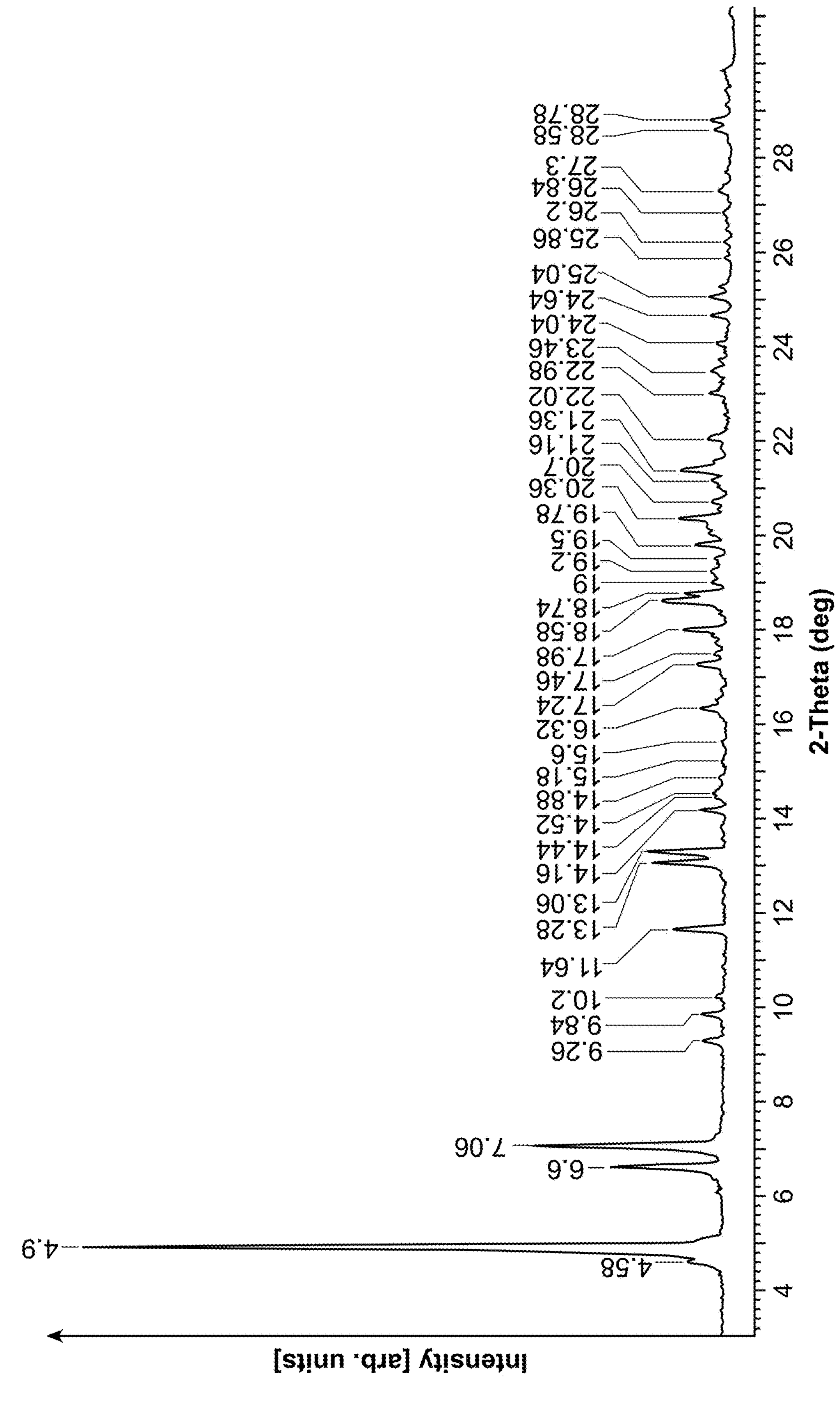
FIGS. 7A and 7B show an XRPD analysis of polymorphic Form B.
Figure 7B:
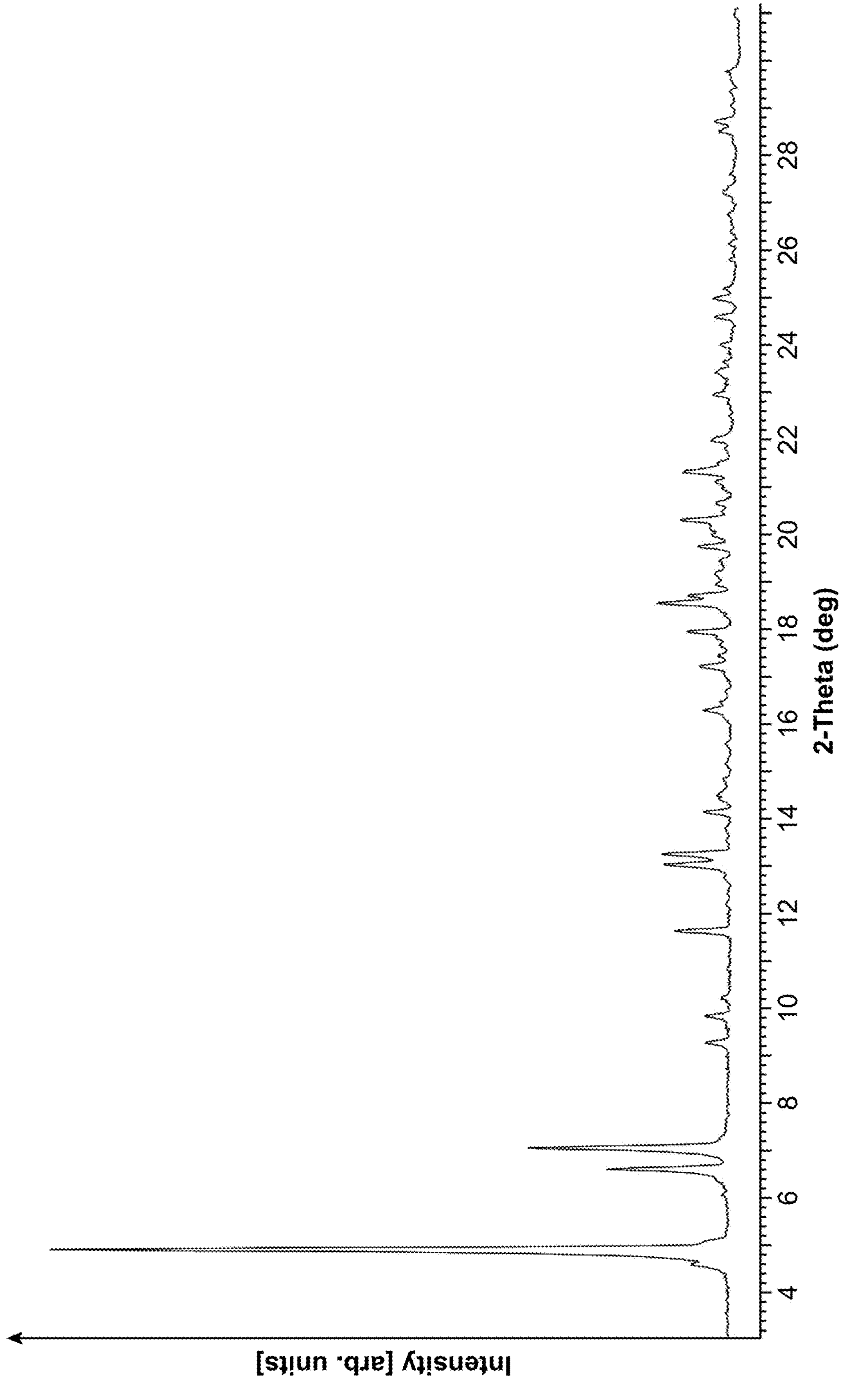

The Form B polymorph may have an XRPD diffractogram approximately as set out in FIG. 7A or 7B.

The Form B polymorph is a hydrate.

The Form B polymorph typically has a TGA profile comprising weight loss of about 8.9% to about 12.9% (e.g. weight loss of about 9.9% to about 11.9%, weight loss of about 10.4% to about 11.4%, weight loss of about 10.7% to about 11.1%, or weight loss of about 10.9%) between 25° C. and 150° C.

Figure 8:
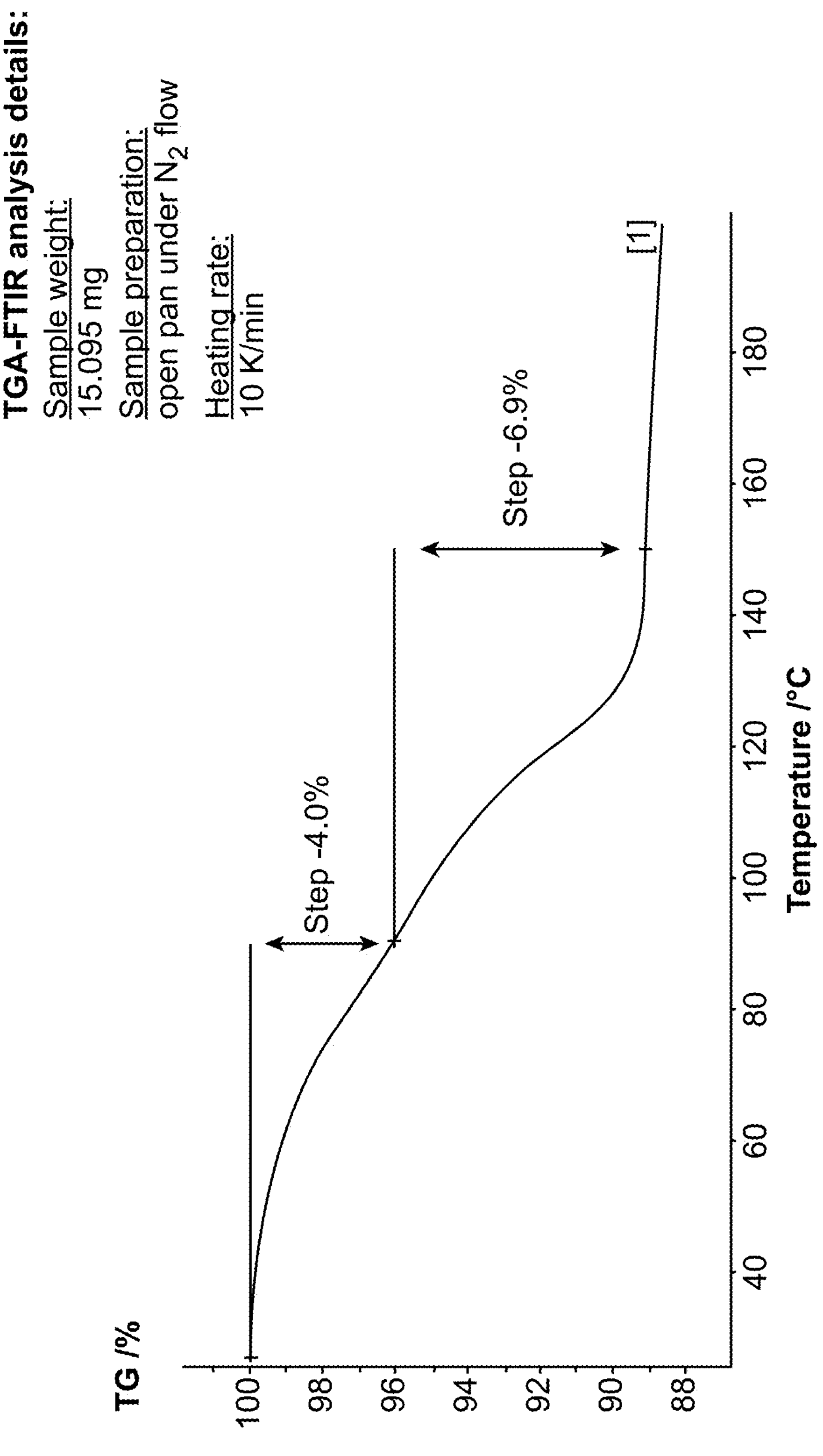
FIG. 8 shows a TGA analysis of polymorphic Form B.

The Form B polymorph may have a TGA profile approximately as set out in FIG. 8.

The Form B polymorph typically has a DSC profile comprising a triple endothermic event (which is believed to be water release), followed by a weak exothermic event, followed by a weak endothermic event, followed by a broad endothermic event.

Figure 9:
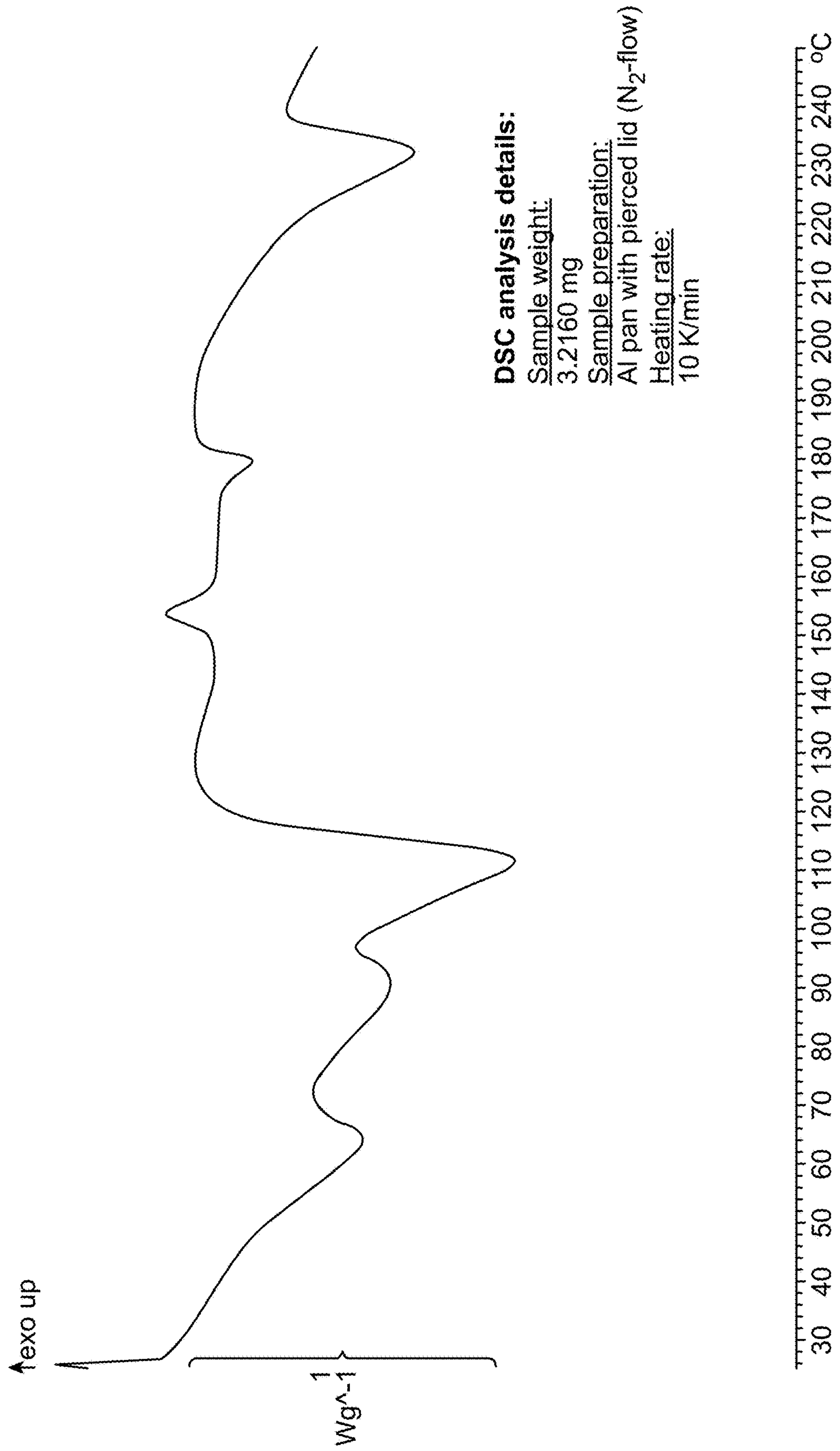
FIG. 9 shows a DSC analysis of polymorphic Form B.

The Form B polymorph may have a DSC profile approximately as set out in FIG. 9.

The Form B polymorph may be obtained by a process comprising:

(a) providing 1-ethyl-N-((1,2,3,5,6,7-hexahydro-s-indacen-4-yl)carbamoyl)piperidine-4-sulfonamide monopotassium salt in methanol to form a mixture; and (b) obtaining a crystalline monopotassium salt of 1-ethyl-N-((1,2,3,5,6,7-hexahydro-s-indacen-4-yl)carbamoyl)piperidine-4-sulfonamide as the Form B polymorph from the mixture.

In a preferred embodiment, in step (b), the mixture is kept at ambient conditions (about 20-40% RH (typically about 30% RH) and about 20-25° C.) under stirring until the solvent has evaporated to obtain the Form B polymorph from the mixture.

Form C Polymorph

The Form C polymorph typically has an XRPD diffractogram comprising peaks at approximately: 5.1 °2θ, 8.9 °2θ, 9.1 °2θ, 15.2 °2θ, and 22.7 °2θ. More typically, the Form C polymorph has an XRPD diffractogram comprising peaks at approximately: 5.1 °2θ, 8.2 °2θ, 8.9 °2θ, 9.1 °2θ, 13.3 °2θ, 15.2 °2θ, 17.2 °2θ, 21.4 °2θ, 22.7 °2θ, and 23.1 °2θ. Still more typically, the Form C polymorph has an XRPD diffractogram comprising peaks at approximately: 5.1 °2θ, 8.2 °2θ, 8.9 °2θ, 9.1 °2θ, 11.8 °2θ, 12.3 °2θ, 12.4 °2θ, 13.3 °2θ, 15.1 °2θ, 15.2 °2θ, 16.4 °2θ, 17.2 °2θ, 20.9 °2θ, 21.2 °2θ, 21.4 °2θ, 22.2 °2θ, 22.7 °2θ, 23.1 °2θ, 25.5 °2θ, and 27.7 °2θ.

The Form C polymorph typically has an XRPD diffractogram in which the 10 most intense peaks include 5 or more (e.g. 6 or more, 7 or more, 8 or more, 9 or more, or 10) peaks which have an approximate 2θ value selected from: 5.1 °2θ, 8.2 °2θ, 8.9 °2θ, 9.1 °2θ, 11.8 °2θ, 12.3 °2θ, 12.4 °2θ, 13.3 °2θ, 15.1 °2θ, 15.2 °2θ, 16.4 °2θ, 17.2 °2θ, 20.9 °2θ, 21.2 °2θ, 21.4 °2θ, 22.2 °2θ, 22.7 °2θ, 23.1 °2θ, 25.5 °2θ, and 27.7 °2θ. More typically, the Form C polymorph has an XRPD diffractogram in which the 10 most intense peaks include 5 or more (e.g. 6 or more, 7 or more, 8 or more, 9 or more, or 10) peaks which have an approximate 2θ value selected from: 5.1 °2θ, 8.2 °2θ, 8.9 °2θ, 9.1 °2θ, 13.3 °2θ, 15.2 °2θ, 17.2 °2θ, 21.4 °2θ, 22.7 °2θ, and 23.1 °2θ.

The Form C polymorph may have an XRPD diffractogram approximately as set out in Table 4 below:

TABLE 4

| Form C | |
|---|---|
| Angle/°2θ | Intensity % |
| 5.1 | 100 |
| 8.2 | 20 |
| 8.9 | 32 |
| 9.1 | 63 |
| 11.8 | 19 |
| 12.3 | 13 |
| 12.4 | 13 |
| 13.3 | 20 |
| 15.1 | 18 |
| 15.2 | 33 |
| 16.4 | 14 |
| 17.2 | 22 |
| 20.9 | 16 |
| 21.2 | 16 |
| 21.4 | 29 |
| 22.2 | 13 |
| 22.7 | 33 |
| 23.1 | 26 |
| 25.5 | 15 |
| 27.7 | 14 |

Figure 12:
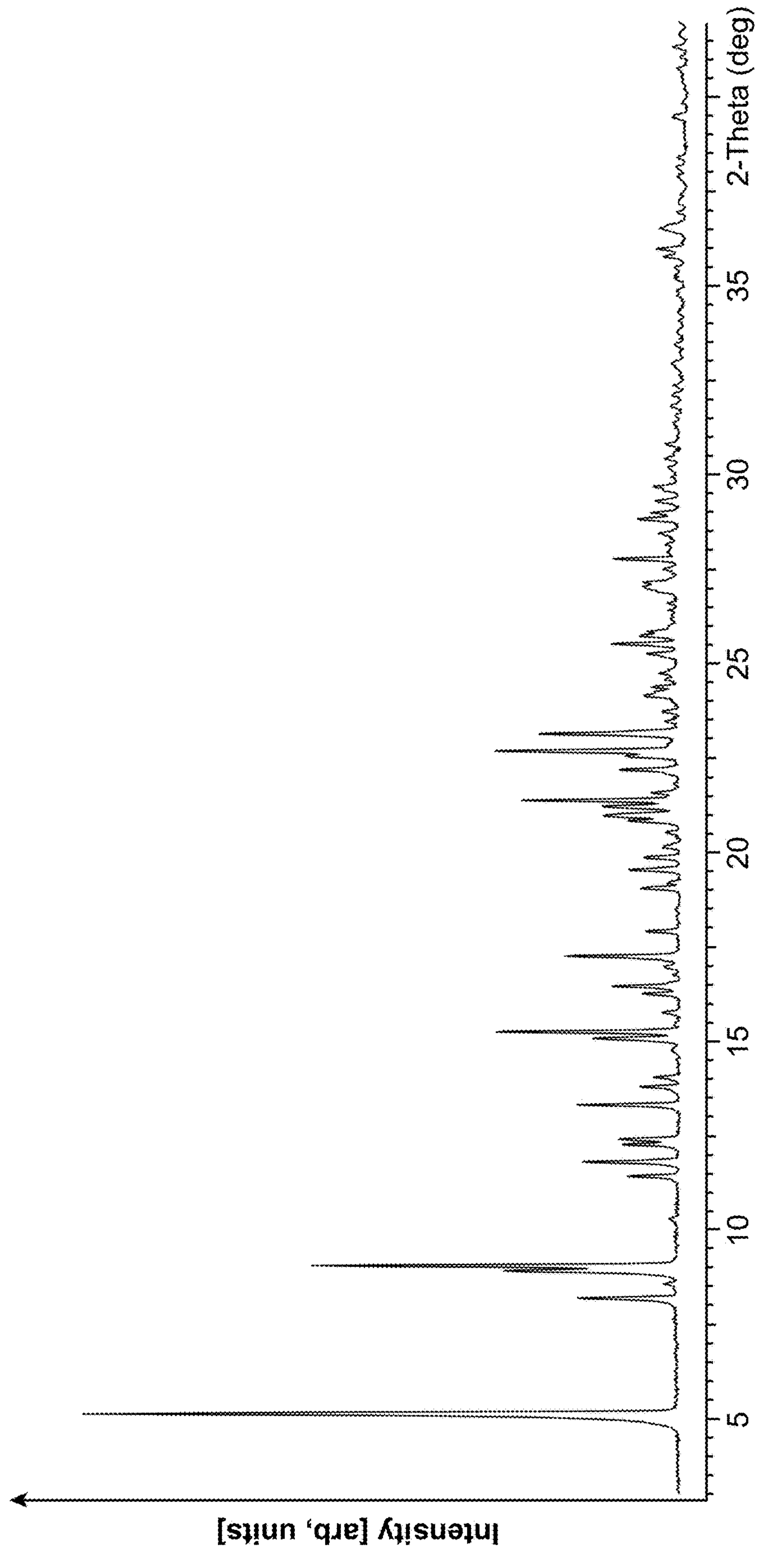
FIG. 12 shows an XRPD analysis of polymorphic Form C.

The Form C polymorph may have an XRPD diffractogram approximately as set out in FIG. 12.

The Form C polymorph is a hydrate.

The Form C polymorph may be obtained by a process comprising:

(a) keeping 1-ethyl-N-((1,2,3,5,6,7-hexahydro-s-indacen-4-yl)carbamoyl)piperidine-4-sulfonamide monopotassium salt in Form A at about 100% RH in a closed vessel over water; and (b) obtaining a crystalline monopotassium salt of 1-ethyl-N-((1,2,3,5,6,7-hexahydro-s-indacen-4-yl)carbamoyl)piperidine-4-sulfonamide as the Form C polymorph.

In a preferred embodiment, in step (a), the 1-ethyl-N-((1,2,3,5,6,7-hexahydro-s-indacen-4-yl)carbamoyl)piperidine-4-sulfonamide monopotassium salt is kept at a temperature of about 15-25° C. (preferably about 23° ° C.) for about 5-20 days (preferably about 13 days).

Form E Polymorph

The Form E polymorph typically has an XRPD diffractogram comprising peaks at approximately: 5.6 °2θ, 6.2 °2θ, 10.7 °2θ, 11.3 °2θ, and 21.7 °2θ. More typically, the Form E polymorph has an XRPD diffractogram comprising peaks at approximately: 5.6 °2θ, 6.2 °2θ, 8.7 °2θ, 10.7 °2θ, 11.3 °2θ, 14.4 °2θ, 20.8 °2θ, 21.5 °2θ, 21.7 °2θ, and 21.9 °2θ. Still more typically, the Form E polymorph has an XRPD diffractogram comprising peaks at approximately: 5.6 °2θ, 6.2 °2θ, 8.7 °2θ, 9.1 °2θ, 10.7 °2θ, 11.3 °2θ, 11.5 °2θ, 11.7 °2θ, 12.4 °2θ, 13.1 °2θ, 13.4 °2θ, 14.4 °2θ, 15.6 °2θ, 16.6 °2θ, 18.7 °2θ, 19.0 °2θ, 20.8 °2θ, 21.5 °2θ, 21.7 °2θ, and 21.9 °2θ.

The Form E polymorph typically has an XRPD diffractogram in which the 10 most intense peaks include 5 or more (e.g. 6 or more, 7 or more, 8 or more, 9 or more, or 10) peaks which have an approximate 2θ value selected from: 5.6 °2θ, 6.2 °2θ, 8.7 °2θ, 9.1 °2θ, 10.7 °2θ, 11.3 °2θ, 11.5 °2θ, 11.7 °2θ, 12.4 °2θ, 13.1 °2θ, 13.4 °2θ, 14.4 °2θ, 15.6 °2θ, 16.6 °2θ, 18.7 °2θ, 19.0 °2θ, 20.8 °2θ, 21.5 °2θ, 21.7 °2θ, and 21.9 °2θ. More typically, the Form E polymorph has an XRPD diffractogram in which the 10 most intense peaks include 5 or more (e.g. 6 or more, 7 or more, 8 or more, 9 or more, or 10) peaks which have an approximate 2θ value selected from: 5.6 °2θ, 6.2 °2θ, 8.7 °2θ, 10.7 °2θ, 11.3 °2θ, 14.4 °2θ, 20.8 °2θ, 21.5 °2θ, 21.7 °2θ, and 21.9 °2θ.

The Form E polymorph may have an XRPD diffractogram approximately as set out in Table 5 below:

TABLE 5

| Form E | |
|---|---|
| Angle/°2θ | Intensity % |
| 5.6 | 98 |
| 6.2 | 100 |
| 8.7 | 24 |
| 9.1 | 22 |
| 10.7 | 28 |
| 11.3 | 28 |
| 11.5 | 22 |
| 11.7 | 20 |
| 12.4 | 21 |
| 13.1 | 23 |
| 13.4 | 21 |
| 14.4 | 27 |
| 15.6 | 22 |
| 16.6 | 22 |
| 18.7 | 23 |
| 19.0 | 19 |
| 20.8 | 23 |
| 21.5 | 24 |
| 21.7 | 37 |
| 21.9 | 27 |

Figure 13:
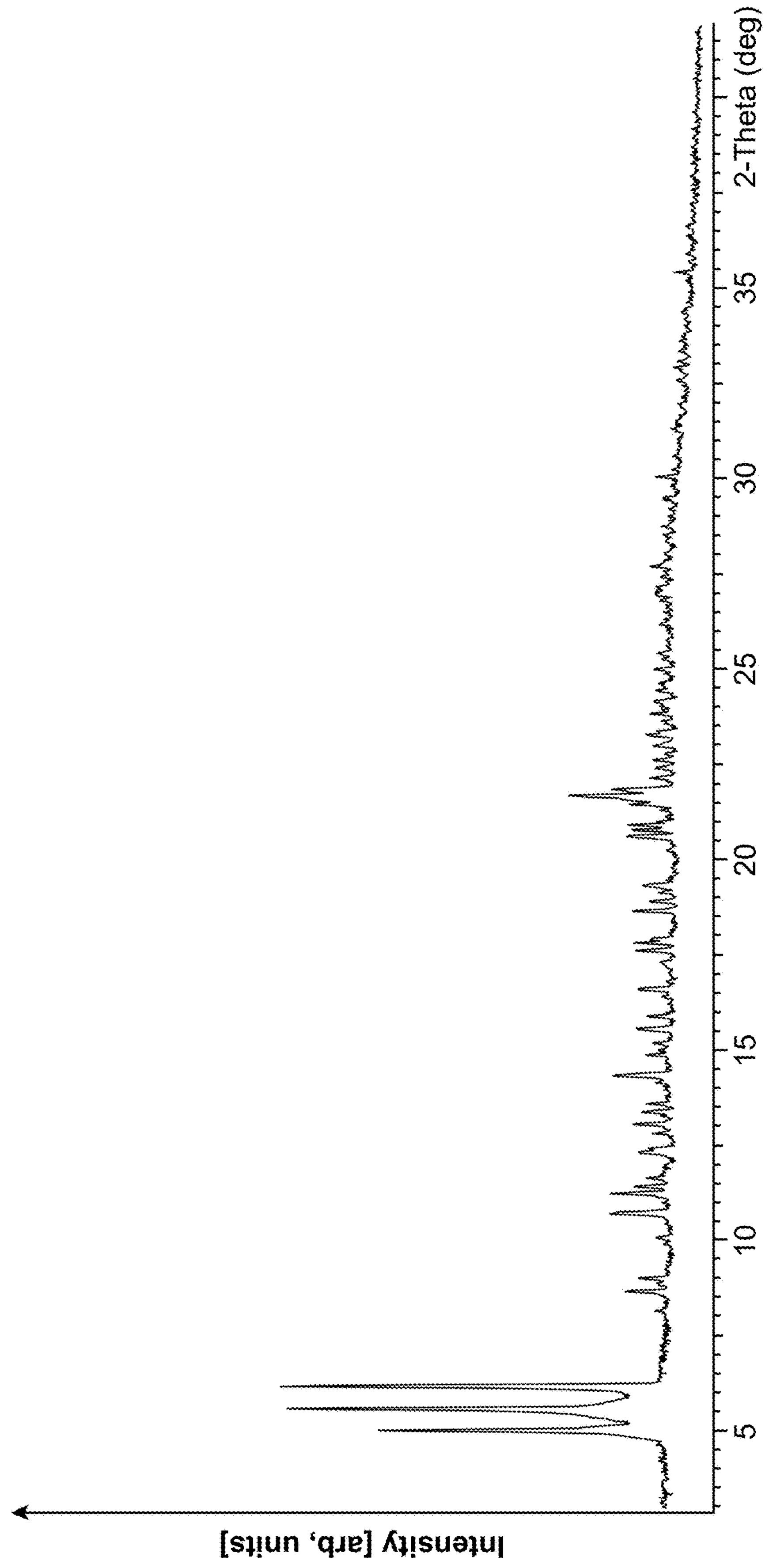
FIG. 13 shows an XRPD analysis of polymorphic Form E.

The Form E polymorph may have an XRPD diffractogram approximately as set out in FIG. 13.

The Form E polymorph is a hydrate.

The Form E polymorph may be obtained by a process comprising:

(a) suspending 1-ethyl-N-((1,2,3,5,6,7-hexahydro-s-indacen-4-yl)carbamoyl)piperidine-4-sulfonamide monopotassium salt (preferably in Form A) in a mixture of acetonitrile/water in a ratio of about 5/95 (v/v) to form a suspension; and (b) obtaining a crystalline monopotassium salt of 1-ethyl-N-((1,2,3,5,6,7-hexahydro-s-indacen-4-yl)carbamoyl) piperidine-4-sulfonamide as the Form E polymorph from the suspension.

In a preferred embodiment, in step (a), the suspension is kept at a temperature of about 15-25° C. (preferably about 23° C.) for about 1-20 days (preferably about 6 days), preferably in a closed vessel.

Form F Polymorph

The Form F polymorph typically has an XRPD diffractogram comprising peaks at approximately: 4.9 °2θ, 9.8 °2θ, 19.1 °2θ, 20.5 °2θ, and 22.2 °2θ0. More typically, the Form F polymorph has an XRPD diffractogram comprising peaks at approximately: 4.9 °2θ, 9.8 °2θ, 15.6 °2θ, 17.0 °2θ, 19.1 °2θ, 19.4 °2θ, 19.9 °2θ, 20.5 °2θ, 21.7°2θ, and 22.2 °2θ. Still more typically, the Form F polymorph has an XRPD diffractogram comprising peaks at approximately: 4.9 °2θ, 6.5 °2θ, 9.8 °2θ, 12.9 °2θ, 13.9 °2θ, 14.7 °2θ, 15.6 °2θ, 15.9 °2θ, 16.4 °2θ, 17.0 °2θ, 17.6 °2θ, 19.1 °2θ, 19.4 °2θ, 19.9 °2θ, 20.1 °2θ, 20.5 °2θ, 20.9 °2θ, 21.2 °2θ, 21.7 °2θ, and 22.2 °2θ.

The Form F polymorph typically has an XRPD diffractogram in which the 10 most intense peaks include 5 or more (e.g. 6 or more, 7 or more, 8 or more, 9 or more, or 10) peaks which have an approximate 2θ value selected from: 4.9 °2θ, 6.5 °2θ, 9.8 °2θ, 12.9 °2θ, 13.9 °2θ, 14.7 °2θ, 15.6 °2θ, 15.9 °2θ, 16.4 °2θ, 17.0 °2θ, 17.6 °2θ, 19.1 °2θ, 19.4 °2θ, 19.9 °2θ, 20.1 °2θ, 20.5 °2θ, 20.9 °2θ, 21.2 °2θ, 21.7 °2θ, and 22.2 °2θ. More typically, the Form F polymorph has an XRPD diffractogram in which the 10 most intense peaks include 5 or more (e.g. 6 or more, 7 or more, 8 or more, 9 or more, or 10) peaks which have an approximate 2θ value selected from: 4.9 °2θ, 9.8 °2θ, 15.6 °2θ, 17.0 °2θ, 19.1 °2θ, 19.4 °2θ, 19.9 °2θ, 20.5 °2θ, 21.7 °2θ, and 22.2 °2θ.

The Form F polymorph may have an XRPD diffractogram approximately as set out in Table 6 below:

TABLE 6

| Form F | |
|---|---|
| Angle/°2θ | Intensity % |
| 4.9 | 100 |
| 6.5 | 4 |
| 9.8 | 10 |
| 12.9 | 5 |
| 13.9 | 6 |
| 14.7 | 6 |
| 15.6 | 7 |
| 15.9 | 4 |
| 16.4 | 4 |
| 17.0 | 9 |
| 17.6 | 6 |
| 19.1 | 25 |
| 19.4 | 9 |
| 19.9 | 7 |
| 20.1 | 6 |
| 20.5 | 13 |
| 20.9 | 7 |
| 21.2 | 6 |
| 21.7 | 8 |
| 22.2 | 11 |

Figure 14:
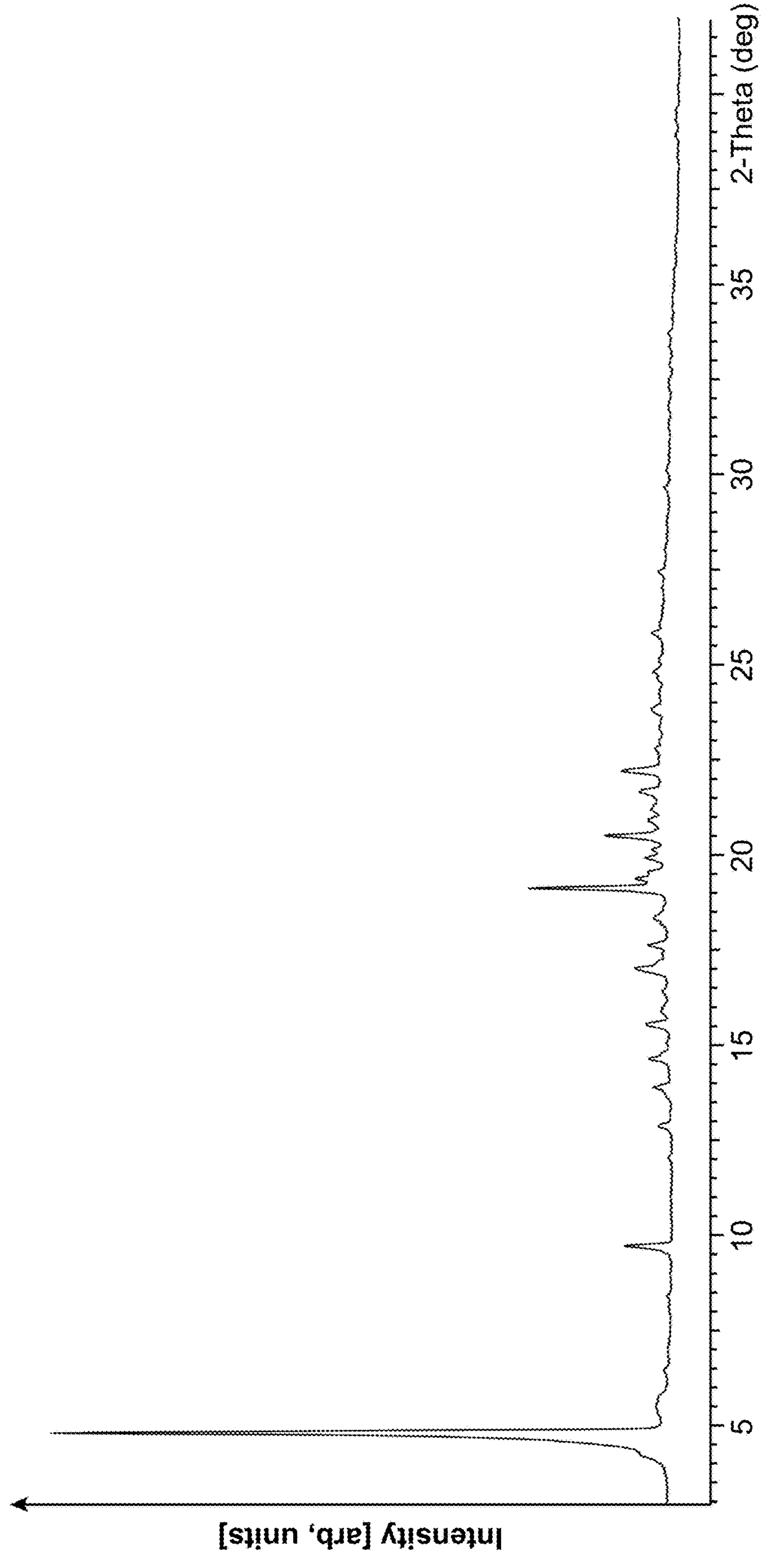
FIG. 14 shows an XRPD analysis of polymorphic Form F.

The Form F polymorph may have an XRPD diffractogram approximately as set out in FIG. 14.

The Form F polymorph is a hydrate.

The Form F polymorph may be obtained by a process comprising:

(a) suspending 1-ethyl-N-((1,2,3,5,6,7-hexahydro-s-indacen-4-yl)carbamoyl)piperidine-4-sulfonamide monopotassium salt (preferably in Form A) in a mixture of acetonitrile/water in a ratio of about 95/5 (w/w) to form a suspension; and (b) obtaining a crystalline monopotassium salt of 1-ethyl-N-((1,2,3,5,6,7-hexahydro-s-indacen-4-yl)carbamoyl) piperidine-4-sulfonamide as the Form F polymorph from the suspension.

In a preferred embodiment, in step (a), the suspension is kept at a temperature of about 15-25° C. (preferably about) 21° C. for about 1-20 days (preferably about 3 days), preferably in a closed vessel.

Form G Polymorph

The Form G polymorph typically has an XRPD diffractogram comprising peaks at approximately: 4.8 °2θ, 8.7 °2θ, 9.0 °2θ, 16.4 °2θ, and 18.0 °2θ. More typically, the Form G polymorph has an XRPD diffractogram comprising peaks at approximately: 4.8 °2θ, 8.7 °2θ, 9.0 °2θ, 10.5 °2θ, 14.5 °2θ, 15.8 °2θ, 16.4 °2θ, 18.0 °2θ, 20.3 °2θ, and 22.7 °2θ. Still more typically, the Form G polymorph has an XRPD diffractogram comprising peaks at approximately: 4.8 °2θ, 8.7°2θ, 9.0 °2θ, 9.6 °2θ, 10.1 °2θ, 10.5 °2θ, 13.5 °2θ, 14.5 °2θ, 15.8 °2θ, 16.4 °2θ, 18.0 °2θ, 19.8 °2θ, 20.3 °2θ, 21.8 °2θ, 22.7 °2θ, 23.4 °2θ, 23.7 °2θ, 24.9 °2θ, 27.2 °2θ, and 29.2 °2θ.

The Form G polymorph typically has an XRPD diffractogram in which the 10 most intense peaks include 5 or more (e.g. 6 or more, 7 or more, 8 or more, 9 or more, or 10) peaks which have an approximate 2θ value selected from: 4.8 °2θ, 8.7 °2θ, 9.0 °2θ, 9.6 °2θ, 10.1 °2θ, 10.5 °2θ, 13.5 °2θ, 14.5 °2θ, 15.8 °2θ, 16.4 °2θ, 18.0 °2θ, 19.8 °2θ, 20.3 °2θ, 21.8 °2θ, 22.7 °2θ, 23.4 °2θ, 23.7 °2θ, 24.9 °2θ, 27.2 °2θ, and 29.2 °2θ. More typically, the Form G polymorph has an XRPD diffractogram in which the 10 most intense peaks include 5 or more (e.g. 6 or more, 7 or more, 8 or more, 9 or more, or 10) peaks which have an approximate 2θ value selected from: 4.8 °2θ, 8.7 °2θ, 9.0 °2θ, 14.5 °2θ, 15.8 °2θ, 16.4 °2θ, 18.0 °2θ, 20.3 °2θ, and 22.7 °2θ.

The Form G polymorph may have an XRPD diffractogram approximately as set out in Table 7 below:

TABLE 7

| Form G | |
|---|---|
| Angle/°2θ | Intensity % |
| 4.8 | 100 |
| 8.7 | 33 |
| 9.0 | 30 |
| 9.6 | 6 |
| 10.1 | 5 |
| 10.5 | 7 |
| 13.5 | 5 |
| 14.5 | 7 |
| 15.8 | 6 |
| 16.4 | 7 |
| 18.0 | 10 |
| 19.8 | 4 |
| 20.3 | 7 |
| 21.8 | 5 |
| 22.7 | 6 |
| 23.4 | 5 |
| 23.7 | 6 |
| 24.9 | 6 |
| 27.2 | 4 |
| 29.2 | 3 |

Figure 15:
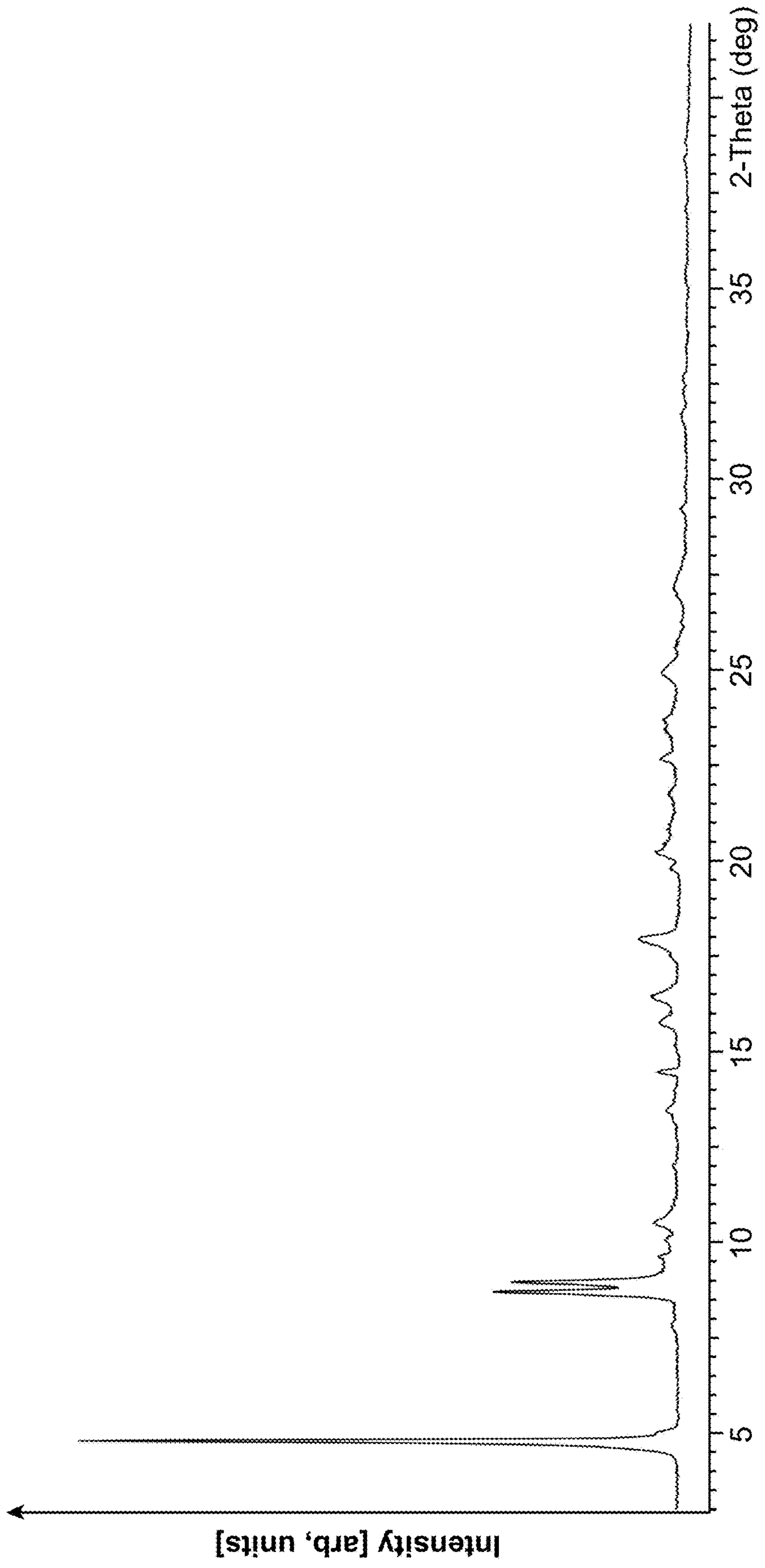
FIG. 15 shows an XRPD analysis of polymorphic Form G.

The Form G polymorph may have an XRPD diffractogram approximately as set out in FIG. 15.

The Form G polymorph is a hydrate.

The Form G polymorph may be obtained by a process comprising:

(a) drying 1-ethyl-N-((1,2,3,5,6,7-hexahydro-s-indacen-4-yl)carbamoyl)piperidine-4-sulfonamide monopotassium salt in Form C at about 0% RH; and (b) obtaining a crystalline monopotassium salt of 1-ethyl-N-((1,2,3,5,6,7-hexahydro-s-indacen-4-yl)carbamoyl) piperidine-4-sulfonamide as the Form G polymorph.

In a preferred embodiment, in step (a), the 1-ethyl-N-((1,2,3,5,6,7-hexahydro-s-indacen-4-yl)carbamoyl)piperidine-4-sulfonamide monopotassium salt is dried at a temperature of about 15-25° C. (preferably about 23° C.) for about 1-10 days (preferably about 5 days).

Form H Polymorph

The Form H polymorph typically has an XRPD diffractogram comprising peaks at approximately: 5.1 °2θ, 5.6 °2θ, 6.5 °2θ, 14.9 °2θ, and 21.4 °2θ. More typically, the Form H polymorph has an XRPD diffractogram comprising peaks at approximately: 5.1 °2θ, 5.6 °2θ, 6.5 °2θ, 13.1 °2θ, 14.9 °2θ, 15.2 °2θ, 17.7 °2θ, 17.9 °2θ, 21.4 °2θ, and 22.3 °2θ. Still more typically, the Form H polymorph has an XRPD diffractogram comprising peaks at approximately: 5.1 °2θ, 5.6 °2θ, 6.5 °2θ, 8.6 °2θ, 10.2 °2θ, 11.3 °2θ, 11.6 °2θ, 12.9 °2θ, 13.1 °2θ, 13.3 °2θ, 14.2 °2θ, 14.9 °2θ, 15.2 °2θ, 15.3 °2θ, 15.6 °2θ, 17.7 °2θ, 17.9 °2θ, 19.6 °2θ, 21.4 °2θ, and 22.3 °2θ.

The Form H polymorph typically has an XRPD diffractogram in which the 10 most intense peaks include 5 or more (e.g. 6 or more, 7 or more, 8 or more, 9 or more, or 10) peaks which have an approximate 2θ value selected from: 5.1 °2θ, 5.6 °2θ, 6.5 °2θ, 8.6 °2θ, 10.2 °2θ, 11.3 °2θ, 11.6 °2θ, 12.9 °2θ, 13.1 °2θ, 13.3 °2θ, 14.2 °2θ, 14.9 °2θ, 15.2 °2θ, 15.3 °2θ, 15.6 °2θ, 17.7 °2θ, 17.9 °2θ, 19.6 °2θ, 21.4 °2θ, and 22.3 °2θ. More typically, the Form H polymorph has an XRPD diffractogram in which the 10 most intense peaks include 5 or more (e.g. 6 or more, 7 or more, 8 or more, 9 or more, or 10) peaks which have an approximate 2θ value selected from: 5.1 °2θ, 5.6 °2θ, 6.5 °2θ, 13.1 °2θ, 14.9 °2θ, 15.2 °2θ, 17.7 °2θ, 17.9 °2θ, 21.4 °2θ, and 22.3 °2θ.

The Form H polymorph may have an XRPD diffractogram approximately as set out in Table 8 below:

TABLE 8

| Form H | |
|---|---|
| Angle/°2θ | Intensity % |
| 5.1 | 100 |
| 5.6 | 22 |
| 6.5 | 28 |
| 8.6 | 12 |
| 10.2 | 8 |
| 11.3 | 12 |
| 11.6 | 9 |
| 12.9 | 13 |
| 13.1 | 13 |
| 13.3 | 11 |
| 14.2 | 10 |
| 14.9 | 21 |
| 15.2 | 13 |
| 15.3 | 8 |
| 15.6 | 10 |
| 17.7 | 14 |
| 17.9 | 16 |
| 19.6 | 11 |
| 21.4 | 18 |
| 22.3 | 16 |

Figure 16:
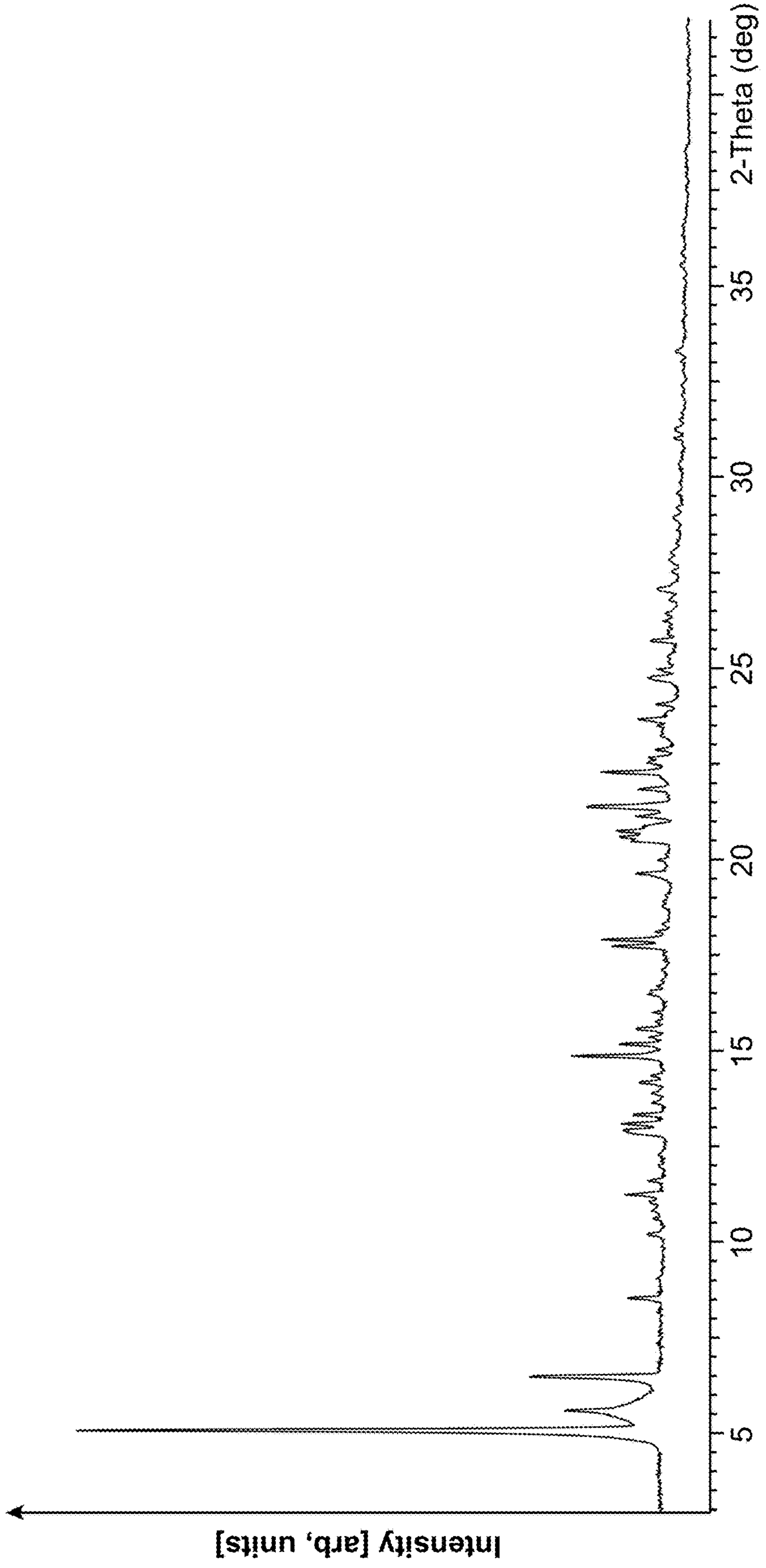
FIG. 16 shows an XRPD analysis of polymorphic Form H.

The Form H polymorph may have an XRPD diffractogram approximately as set out in FIG. 16.

The Form H polymorph is a hydrate.

The Form H polymorph may be obtained by a process comprising:

(a) suspending 1-ethyl-N-((1,2,3,5,6,7-hexahydro-s-indacen-4-yl)carbamoyl)piperidine-4-sulfonamide monopotassium salt (preferably in Form A) in a mixture of acetonitrile/water in a ratio of about 85/15 (v/v) to form a suspension; and (b) obtaining a crystalline monopotassium salt of 1-ethyl-N-((1,2,3,5,6,7-hexahydro-s-indacen-4-yl)carbamoyl) piperidine-4-sulfonamide as the Form H polymorph from the suspension.

In a preferred embodiment, in step (a), the suspension is kept at a temperature of about 15-25° C. (preferably about 23° C.) for about 1-20 days (preferably about 13 days), preferably in a closed vessel.

Form I Polymorph

The Form I polymorph typically has an XRPD diffractogram comprising peaks at approximately: 4.7 °2θ, 5.0 °2θ, 6.2 °2θ, 6.7 °2θ, and 15.6 °2θ. More typically, the Form I polymorph has an XRPD diffractogram comprising peaks at approximately: 3.7 °2θ, 4.7 °2θ, 5.0 °2θ, 6.2 °2θ, 6.7 °2θ, 10.2 °2θ, 12.3 °2θ, 12.9 °2θ, 14.6 °2θ, and 15.6 °2θ. Still more typically, the Form I polymorph has an XRPD diffractogram comprising peaks at approximately: 3.7 °2θ, 4.7 °2θ, 5.0 °2θ, 6.2 °2θ, 6.7 °2θ, 7.0 °2θ, 7.1 °2θ, 7.7 °2θ, 9.5 °2θ, 9.8 °2θ, 10.2 °2θ, 10.4 °2θ, 10.8 °2θ, 11.0 °2θ, 11.3 °2θ, 12.3 °2θ, 12.9 °2θ, 14.6 °2θ, 14.9 °2θ, and 15.6 °20.

The Form I polymorph typically has an XRPD diffractogram in which the 10 most intense peaks include 5 or more (e.g. 6 or more, 7 or more, 8 or more, 9 or more, or 10) peaks which have an approximate 2θ value selected from: 3.7 °2θ, 4.7 °2θ, 5.0 °2θ, 6.2 °2θ, 6.7 °2θ, 7.0 °2θ, 7.1 °2θ, 7.7 °2θ, 9.5 °2θ, 9.8 °2θ, 10.2 °2θ, 10.4 °2θ, 10.8 °2θ, 11.0 °2θ, 11.3 °2θ, 12.3 °2θ, 12.9 °2θ, 14.6 °2θ, 14.9 °2θ, and 15.6 °2θ. More typically, the Form I polymorph has an XRPD diffractogram in which the 10 most intense peaks include 5 or more (e.g. 6 or more, 7 or more, 8 or more, 9 or more, or 10) peaks which have an approximate 2θ value selected from: 3.7 °2θ, 4.7 °2θ, 5.0 °2θ, 6.2 °2θ, 6.7 °2θ, 10.2 °2θ, 12.3 °2θ, 12.9 °2θ, 14.6 °2θ, and 15.6 °2θ.

The Form I polymorph may have an XRPD diffractogram approximately as set out in Table 9 below:

TABLE 9

| Form I | |
|---|---|
| Angle/°2θ | Intensity % |
| 3.7 | 12 |
| 4.7 | 100 |
| 5.0 | 65 |
| 6.2 | 58 |
| 6.7 | 13 |
| 7.0 | 11 |
| 7.1 | 11 |
| 7.7 | 10 |
| 9.5 | 11 |
| 9.8 | 11 |
| 10.2 | 12 |
| 10.4 | 10 |
| 10.8 | 11 |
| 11.0 | 10 |
| 11.3 | 11 |
| 12.3 | 12 |
| 12.9 | 11 |
| 14.6 | 12 |
| 14.9 | 11 |
| 15.6 | 14 |

Figure 17:
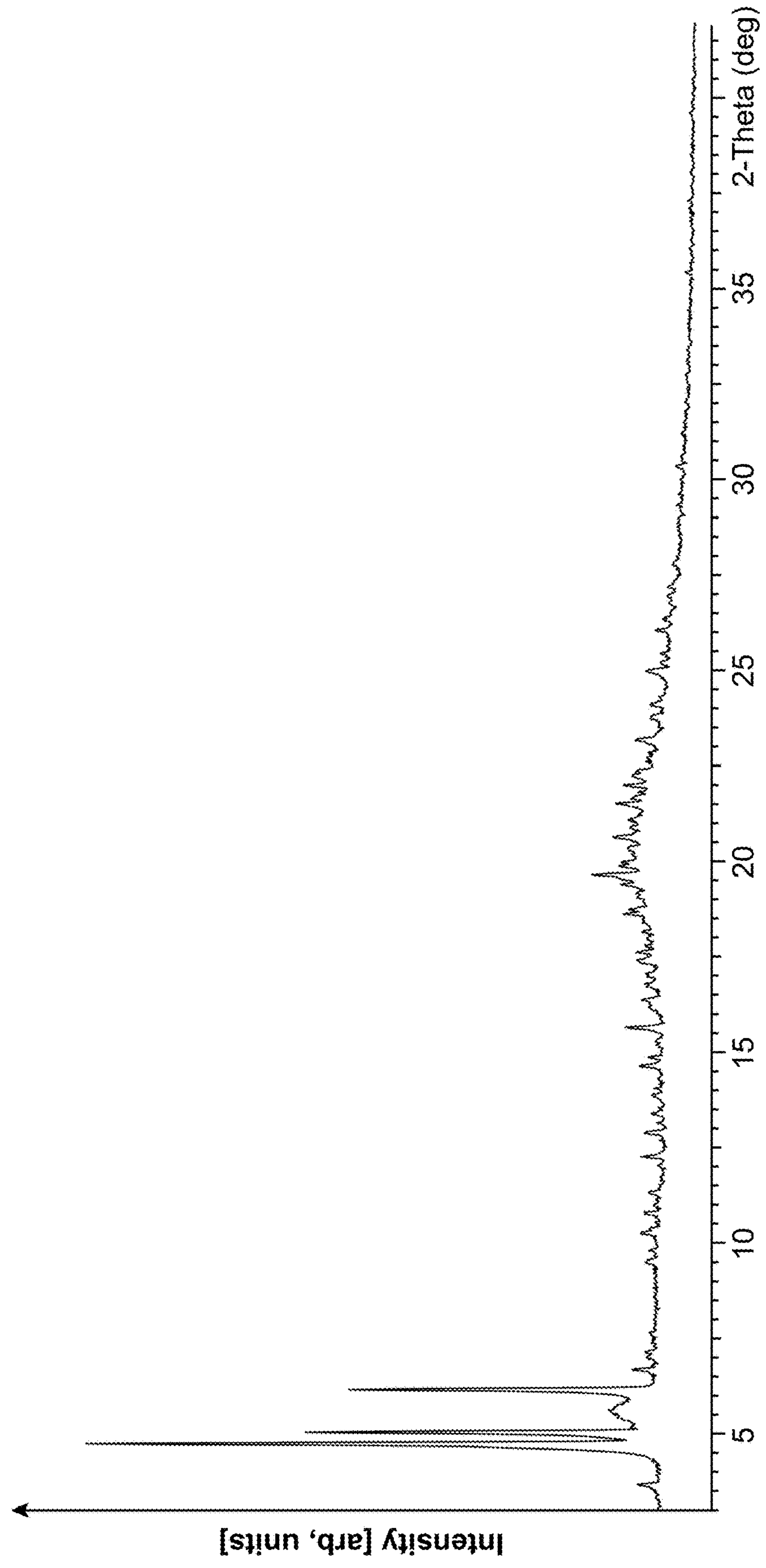
FIG. 17 shows an XRPD analysis of polymorphic Form I.

The Form I polymorph may have an XRPD diffractogram approximately as set out in FIG. 17.

The Form I polymorph is believed to be an n-propanol solvate.

The Form I polymorph may be obtained by a process comprising:

(a) suspending 1-ethyl-N-((1,2,3,5,6,7-hexahydro-s-indacen-4-yl)carbamoyl)piperidine-4-sulfonamide monopotassium salt (preferably in Form A) in n-propanol to form a suspension (preferably in a closed vessel); and (b) obtaining a crystalline monopotassium salt of 1-ethyl-N-((1,2,3,5,6,7-hexahydro-s-indacen-4-yl)carbamoyl) piperidine-4-sulfonamide as the Form I polymorph from the suspension.

In a preferred embodiment, in step (a), the suspension is kept at a temperature of about 15-25° C. (preferably about 23° C.) for about 1-24 hours (preferably about 2 hours), preferably in a closed vessel.

Form J Polymorph

The Form J polymorph typically has an XRPD diffractogram comprising peaks at approximately: 5.2 °2θ, 5.7 °2θ, 19.2 °2θ, 21.6 °2θ, and 22.9 °2θ. More typically, the Form J polymorph has an XRPD diffractogram comprising peaks at approximately: 5.2 °2θ, 5.7 °2θ, 19.2 °2θ, 19.7 °2θ, 20.6 °2θ, 21.2 °2θ, 21.6 °2θ, 21.9 °2θ, 22.9 °2θ, and 23.6 °2θ. Still more typically, the Form J polymorph has an XRPD diffractogram comprising peaks at approximately: 5.2 °2θ, 5.7 °2θ, 6.6 °2θ, 17.0 °2θ, 19.2 °2θ, 19.7 °2θ, 20.3 °2θ, 20.4 °2θ, 20.6 °2θ, 20.7 °2θ, 21.0 °2θ, 21.2 °2θ, 21.6 °2θ, 21.8 °2θ, 21.9 °2θ, 22.0 °2θ, 22.9 °2θ, 23.6 °2θ, 24.4 °2θ, and 24.5 °2θ.

The Form J polymorph typically has an XRPD diffractogram in which the 10 most intense peaks include 5 or more (e.g. 6 or more, 7 or more, 8 or more, 9 or more, or 10) peaks which have an approximate 2θ value selected from: 5.2 °2θ, 5.7 °2θ, 6.6 °2θ, 17.0 °2θ, 19.2 °2θ, 19.7 °2θ, 20.3 °2θ, 20.4 °2θ, 20.6 °2θ, 20.7 °2θ, 21.0 °2θ, 21.2 °2θ, 21.6 °2θ, 21.8 °2θ, 21.9 °2θ, 22.0 °2θ, 22.9 °2θ, 23.6 °2θ, 24.4 °2θ, and 24.5 °2θ. More typically, the Form J polymorph has an XRPD diffractogram in which the 10 most intense peaks include 5 or more (e.g. 6 or more, 7 or more, 8 or more, 9 or more, or 10) peaks which have an approximate 2θ value selected from: 5.2 °2θ, 5.7 °2θ, 19.2 °2θ, 19.7 °2θ, 20.6 °2θ, 21.2 °2θ, 21.6 °2θ, 21.9 °2θ, 22.9 °2θ, and 23.6 °2θ.

The Form J polymorph may have an XRPD diffractogram approximately as set out in Table 10 below:

TABLE 10

| Form J | |
|---|---|
| Angle/°2θ | Intensity % |
| 5.2 | 100 |
| 5.7 | 32 |
| 6.6 | 15 |
| 17.0 | 15 |
| 19.2 | 30 |
| 19.7 | 16 |
| 20.3 | 14 |
| 20.4 | 15 |
| 20.6 | 16 |
| 20.7 | 15 |
| 21.0 | 16 |
| 21.2 | 16 |
| 21.6 | 18 |
| 21.8 | 15 |
| 21.9 | 16 |
| 22.0 | 15 |
| 22.9 | 20 |
| 23.6 | 17 |
| 24.4 | 15 |
| 24.5 | 15 |

Figure 18:
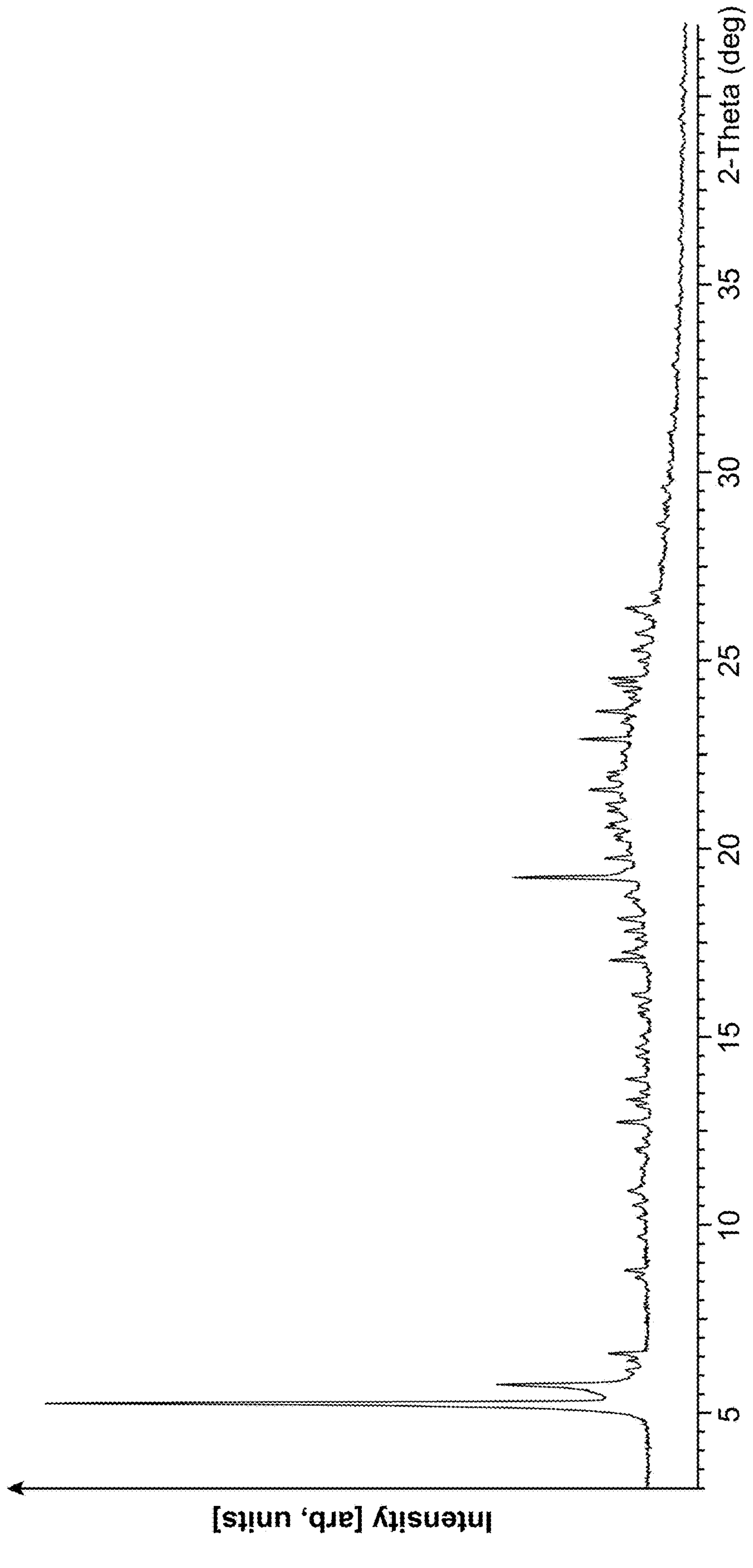
FIG. 18 shows an XRPD analysis of polymorphic Form J.

The Form J polymorph may have an XRPD diffractogram approximately as set out in FIG. 18.

The Form J polymorph is believed to be an ethanol solvate.

The Form J polymorph may be obtained by a process comprising:

(a) suspending 1-ethyl-N-((1,2,3,5,6,7-hexahydro-s-indacen-4-yl)carbamoyl)piperidine-4-sulfonamide monopotassium salt (preferably in Form A) in ethanol to form a suspension (preferably in a closed vessel); and (b) obtaining a crystalline monopotassium salt of 1-ethyl-N-((1,2,3,5,6,7-hexahydro-s-indacen-4-yl)carbamoyl) piperidine-4-sulfonamide as the Form J polymorph from the suspension.

In a preferred embodiment, in step (a), the suspension is kept at a temperature of about 15-25° C. (preferably about 23° C.) for about 1-24 hours (preferably about 2 hours), preferably in a closed vessel.

Form K Polymorph

The Form K polymorph typically has an XRPD diffractogram comprising peaks at approximately: 5.1 °2θ, 6.1 °2θ, 18.2 °2θ, 19.3 °2θ, and 20.6 °2θ. More typically, the Form K polymorph has an XRPD diffractogram comprising peaks at approximately: 5.1 °2θ, 5.8 °2θ, 6.1 °2θ, 11.7 °2θ, 16.2 °2θ, 18.2 °2θ, 18.5 °2θ, 19.3 °2θ, 20.6 °2θ, and 21.7 °2θ. Still more typically, the Form K polymorph has an XRPD diffractogram comprising peaks at approximately: 5.1 °2θ, 5.8 °2θ, 6.1 °2θ, 9.1 °2θ, 10.1 °2θ, 11.7 °2θ, 12.2 °2θ, 13.5 °2θ, 15.2 °2θ, 15.6 °2θ, 16.2 °2θ, 17.2 °2θ, 18.2 °2θ, 18.5 °2θ, 19.0 °2θ, 19.3 °2θ, 19.5 °2θ, 20.3 °2θ, 20.6 °2θ, and 21.7 °2θ.

The Form K polymorph typically has an XRPD diffractogram in which the 10 most intense peaks include 5 or more (e.g. 6 or more, 7 or more, 8 or more, 9 or more, or 10) peaks which have an approximate 2θ value selected from: 5.1 °2θ, 5.8 °2θ, 6.1 °2θ, 9.1 °2θ, 10.1 °2θ, 11.7 °2θ, 12.2 °2θ, 13.5 °2θ, 15.2 °2θ, 15.6 °2θ, 16.2 °2θ, 17.2 °2θ, 18.2 °2θ, 18.5 °2θ, 19.0 °2θ, 19.3 °2θ, 19.5 °2θ, 20.3 °2θ, 20.6 °2θ, and 21.7 °2θ. More typically, the Form K polymorph has an XRPD diffractogram in which the 10 most intense peaks include 5 or more (e.g. 6 or more, 7 or more, 8 or more, 9 or more, or 10) peaks which have an approximate 2θ value selected from: 5.1 °2θ, 5.8 °2θ, 6.1 °2θ, 11.7 °2θ, 16.2 °2θ, 18.2 °2θ, 18.5 °2θ, 19.3 °2θ, 20.6 °2θ, and 21.7 °2θ.

The Form K polymorph may have an XRPD diffractogram approximately as set out in Table 11 below:

TABLE 11

| Form K | |
|---|---|
| Angle/°2θ | Intensity % |
| 5.1 | 100 |
| 5.8 | 37 |
| 6.1 | 98 |
| 9.1 | 15 |
| 10.1 | 15 |
| 11.7 | 33 |
| 12.2 | 18 |
| 13.5 | 23 |
| 15.2 | 17 |
| 15.6 | 18 |
| 16.2 | 29 |
| 17.2 | 26 |
| 18.2 | 47 |
| 18.5 | 45 |
| 19.0 | 22 |
| 19.3 | 61 |
| 19.5 | 26 |
| 20.3 | 26 |
| 20.6 | 67 |
| 21.7 | 44 |

Figure 19:
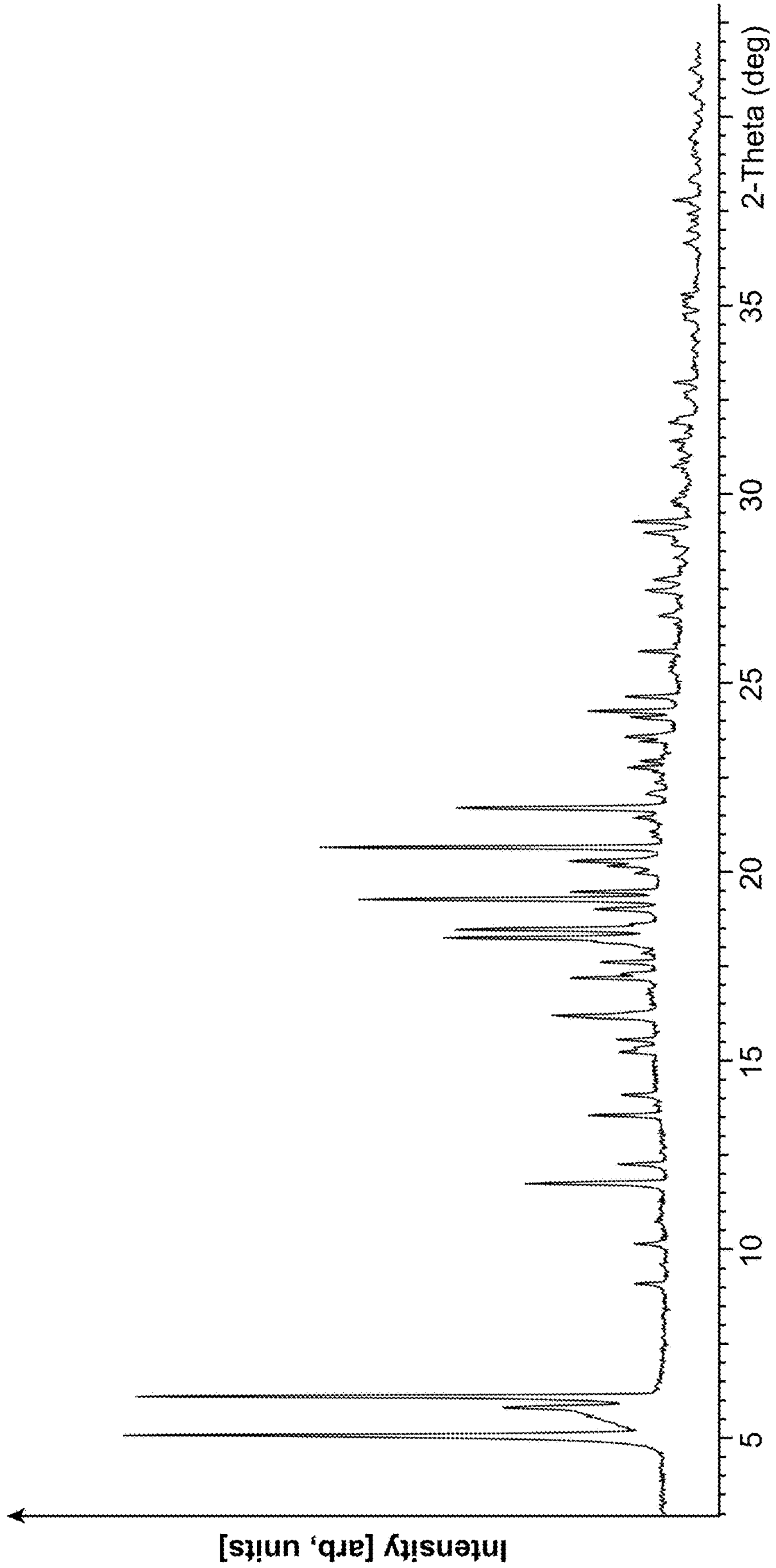
FIG. 19 shows an XRPD analysis of polymorphic Form K.

The Form K polymorph may have an XRPD diffractogram approximately as set out in FIG. 19.

The Form K polymorph is believed to be an n-methyl-2-pyrrolidone (NMP) solvate.

The Form K polymorph may be obtained by a process comprising:

(a) suspending 1-ethyl-N-((1,2,3,5,6,7-hexahydro-s-indacen-4-yl)carbamoyl)piperidine-4-sulfonamide monopotassium salt (preferably in Form A) in n-methyl-2-pyrrolidone (NMP) to form a suspension (preferably in a closed vessel); and (b) obtaining a crystalline monopotassium salt of 1-ethyl-N-((1,2,3,5,6,7-hexahydro-s-indacen-4-yl)carbamoyl) piperidine-4-sulfonamide as the Form K polymorph from the suspension.

In a preferred embodiment, in step (a), the suspension is kept at a temperature of about 15-25° C. (preferably about 23° C.) for about 1-24 hours (preferably about 2 hours), preferably in a closed vessel.

Form L Polymorph

The Form L polymorph typically has an XRPD diffractogram comprising peaks at approximately: 5.0 °2θ, 10.0 °2θ, 11.6 °2θ, 18.1 °2θ, and 18.5 °2θ. More typically, the Form L polymorph has an XRPD diffractogram comprising peaks at approximately: 5.0 °2θ, 5.9 °2θ, 10.0 °2θ, 11.6 °2θ, 18.1 °2θ, 18.3 °2θ, 18.5 °2θ, 19.3 °2θ, 20.2 °2θ, and 20.8 °2θ. Still more typically, the Form L polymorph has an XRPD diffractogram comprising peaks at approximately: 5.0 °2θ, 5.9 °2θ, 10.0 °2θ, 11.6 °2θ, 17.4 °2θ, 18.1 °2θ, 18.3 °2θ, 18.5 °2θ, 18.9 °2θ, 19.1 °2θ, 19.3 °2θ, 20.2 °2θ, 20.8 °2θ, 21.5 °2θ, 23.6 °2θ, 24.6 °2θ, 25.1 °2θ, 27.8 °2θ, 28.8 °2θ, and 30.3 °2θ.

The Form L polymorph typically has an XRPD diffractogram in which the 10 most intense peaks include 5 or more (e.g. 6 or more, 7 or more, 8 or more, 9 or more, or 10) peaks which have an approximate 2θ value selected from: 5.0 °2θ, 5.9 °2θ, 10.0 °2θ, 11.6 °2θ, 17.4 °2θ, 18.1 °2θ, 18.3 °2θ, 18.5 °2θ, 18.9 °2θ, 19.1 °2θ, 19.3 °2θ, 20.2 °2θ, 20.8 °2θ, 21.5 °2θ, 23.6 °2θ, 24.6 °2θ, 25.1 °2θ, 27.8 °2θ, 28.8 °2θ, and 30.3 °2θ. More typically, the Form L polymorph has an XRPD diffractogram in which the 10 most intense peaks include 5 or more (e.g. 6 or more, 7 or more, 8 or more, 9 or more, or 10) peaks which have an approximate 2θ value selected from: 5.0 °2θ, 5.9 °2θ, 10.0 °2θ, 11.6 °2θ, 18.1 °2θ, 18.3 °2θ, 18.5 °2θ, 19.3 °2θ, 20.2 °2θ, and 20.8 °2θ.

The Form L polymorph may have an XRPD diffractogram approximately as set out in Table 12 below:

TABLE 12

| Form L | |
|---|---|
| Angle/°2θ | Intensity % |
| 5.0 | 100 |
| 5.9 | 13 |
| 10.0 | 22 |
| 11.6 | 27 |
| 17.4 | 8 |
| 18.1 | 16 |
| 18.3 | 12 |
| 18.5 | 53 |
| 18.9 | 7 |
| 19.1 | 9 |
| 19.3 | 12 |
| 20.2 | 12 |
| 20.8 | 12 |
| 21.5 | 8 |
| 23.6 | 8 |
| 24.6 | 7 |

TABLE 12-continued

| Form L | |
|---|---|
| Angle/°2θ | Intensity % |
| 25.1 | 9 |
| 27.8 | 9 |
| 28.8 | 7 |
| 30.3 | 8 |

Figure 20:
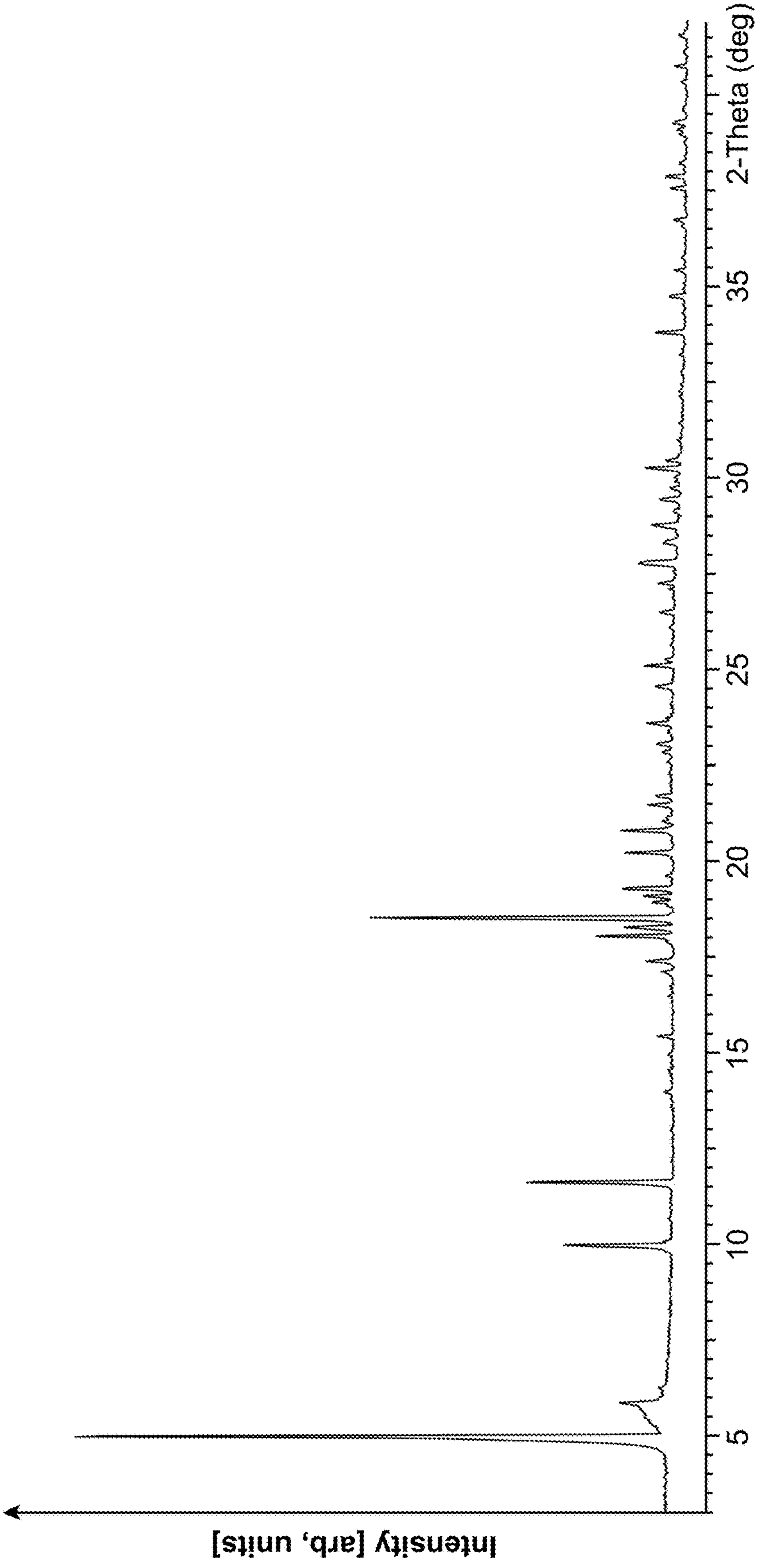
FIG. 20 shows an XRPD analysis of polymorphic Form L.

The Form L polymorph may have an XRPD diffractogram approximately as set out in FIG. 20.

The Form L polymorph is believed to be a methanol solvate.

The Form L polymorph may be obtained by a process comprising:

(a) suspending 1-ethyl-N-((1,2,3,5,6,7-hexahydro-s-indacen-4-yl)carbamoyl)piperidine-4-sulfonamide monopotassium salt (preferably in Form A) in methanol to form a suspension (preferably in a closed vessel); and (b) obtaining a crystalline monopotassium salt of 1-ethyl-N-((1,2,3,5,6,7-hexahydro-s-indacen-4-yl)carbamoyl) piperidine-4-sulfonamide as the Form L polymorph from the suspension.

In a preferred embodiment, in step (a), the suspension is kept at a temperature of about 15-25° C. (preferably about 23° C.) for about 1-24 hours (preferably about 2 hours), preferably in a closed vessel.

Form M Polymorph

The Form M polymorph typically has an XRPD diffractogram comprising peaks at approximately: 5.5 °2θ, 5.7 °2θ, 6.4 °2θ, 19.3 °2θ, and 19.8 °2θ. More typically, the Form M polymorph has an XRPD diffractogram comprising peaks at approximately: 4.6 °2θ, 5.5 °2θ, 5.7 °2θ, 6.4 °2θ, 19.3 °2θ, 19.8 °2θ, 19.9 °2θ, 20.2 °2θ, 21.0 °2θ, and 21.1 °2θ. Still more typically, the Form M polymorph has an XRPD diffractogram comprising peaks at approximately: 4.6 °2θ, 5.5 °2θ, 5.7 °2θ, 6.4 °2θ, 12.8 °2θ, 14.7 °2θ, 15.6 °2θ, 16.2 °2θ, 17.3 °2θ, 17.5 °2θ, 19.3 °2θ, 19.8 °2θ, 19.9 °2θ, 20.2 °2θ, 20.4 °2θ, 21.0 °2θ, 21.1 °2θ, 23.0 °2θ, 24.0 °2θ, and 24.5 °2θ.

The Form M polymorph typically has an XRPD diffractogram in which the 10 most intense peaks include 5 or more (e.g. 6 or more, 7 or more, 8 or more, 9 or more, or 10) peaks which have an approximate 2θ value selected from: 4.6 °2θ, 5.5 °2θ, 5.7 °2θ, 6.4 °2θ, 12.8 °2θ, 14.7 °2θ, 15.6 °2θ, 16.2 °2θ, 17.3 °2θ, 17.5 °2θ, 19.3 °2θ, 19.8 °2θ, 19.9 °2θ, 20.2 °2θ, 20.4 °2θ, 21.0 °2θ, 21.1 °2θ, 23.0 °2θ, 24.0 °2θ, and 24.5 °2θ. More typically, the Form M polymorph has an XRPD diffractogram in which the 10 most intense peaks include 5 or more (e.g. 6 or more, 7 or more, 8 or more, 9 or more, or 10) peaks which have an approximate 2θ value selected from: 4.6 °2θ, 5.5 °2θ, 5.7 °2θ, 6.4 °2θ, 19.3 °2θ, 19.8 °2θ, 19.9 °2θ, 20.2 °2θ, 21.0 °2θ, and 21.1 °2θ.

The Form M polymorph may have an XRPD diffractogram approximately as set out in Table 13 below:

TABLE 13

| Form M | |
|---|---|
| Angle/°2θ | Intensity % |
| 4.6 | 18 |
| 5.5 | 27 |
| 5.7 | 24 |
| 6.4 | 100 |
| 12.8 | 13 |
| 14.7 | 12 |
| 15.6 | 13 |
| 16.2 | 16 |
| 17.3 | 18 |
| 17.5 | 16 |
| 19.3 | 46 |
| 19.8 | 23 |
| 19.9 | 20 |
| 20.2 | 19 |
| 20.4 | 18 |
| 21.0 | 20 |
| 21.1 | 19 |
| 23.0 | 15 |
| 24.0 | 15 |
| 24.5 | 15 |

Figure 21:
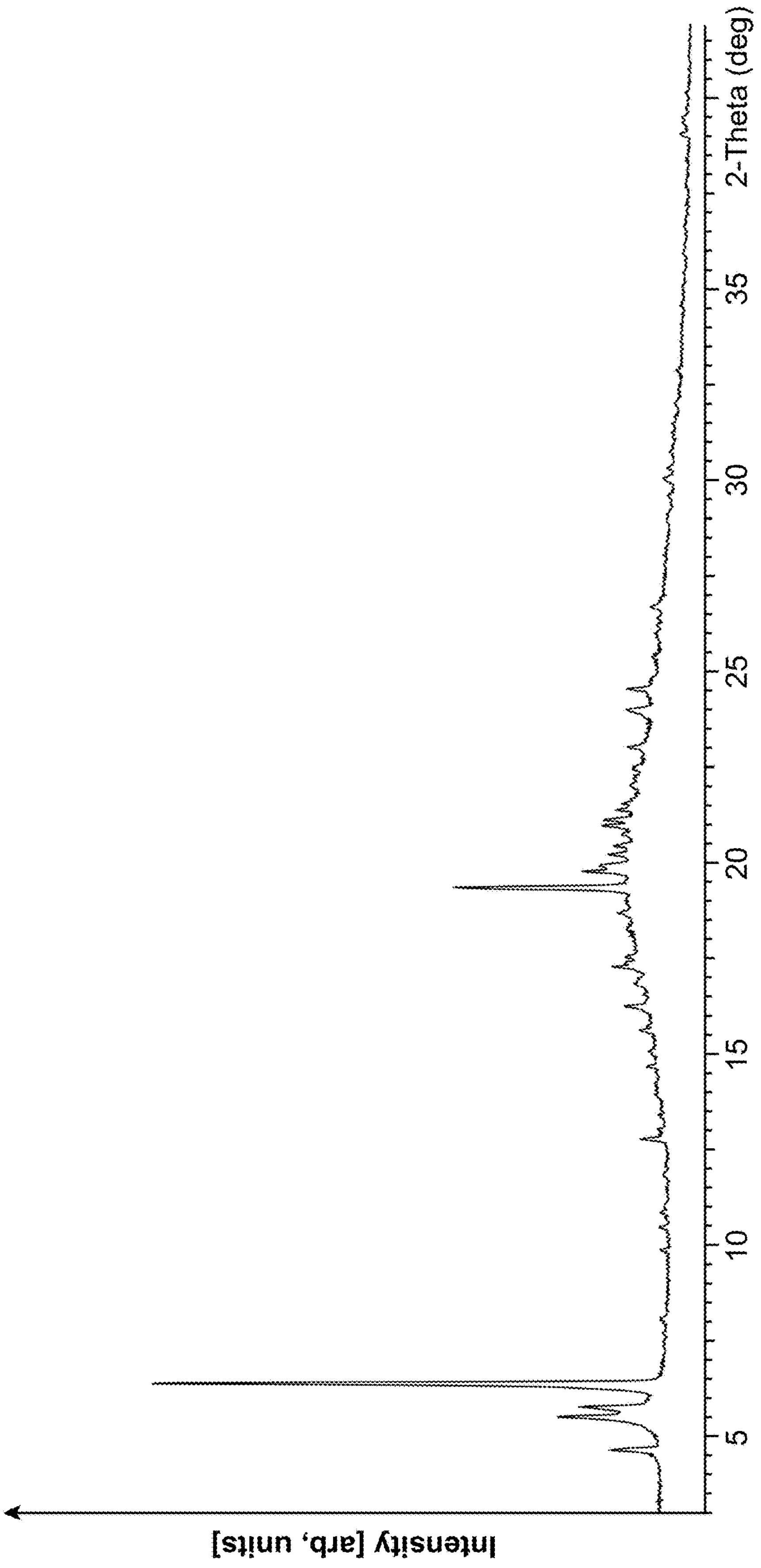
FIG. 21 shows an XRPD analysis of polymorphic Form M.

The Form M polymorph may have an XRPD diffractogram approximately as set out in FIG. 21.

The Form M polymorph is believed to be a dimethylformamide (DMF) solvate.

The Form M polymorph may be obtained by a process comprising:

(a) suspending 1-ethyl-N-((1,2,3,5,6,7-hexahydro-s-indacen-4-yl)carbamoyl)piperidine-4-sulfonamide monopotassium salt (preferably in Form A) in dimethylformamide (DMF) to form a suspension (preferably in a closed vessel); and (b) obtaining a crystalline monopotassium salt of 1-ethyl-N-((1,2,3,5,6,7-hexahydro-s-indacen-4-yl)carbamoyl) piperidine-4-sulfonamide as the Form M polymorph from the suspension.

In a preferred embodiment, in step (a), the suspension is kept at a temperature of about 15-25° C. (preferably about 23° C.) for about 1-15 days (preferably about 9 days), preferably in a closed vessel.

Form N Polymorph

The Form N polymorph typically has an XRPD diffractogram comprising peaks at approximately: 5.0 °2θ, 5.8 °2θ, 17.7 °2θ, 20.2 °2θ, and 22.7 °2θ. More typically, the Form N polymorph has an XRPD diffractogram comprising peaks at approximately: 5.0 °2θ, 5.4 °2θ, 5.8 °2θ, 11.3 °2θ, 17.7 °2θ, 19.0 °2θ, 20.2 °2θ, 21.1 °2θ, 21.6 °2θ, and 22.7 °2θ. Still more typically, the Form N polymorph has an XRPD diffractogram comprising peaks at approximately: 5.0 °2θ, 5.4 °2θ, 5.8 °2θ, 6.3 °2θ, 7.3 °2θ, 10.7 °2θ, 11.3 °2θ, 12.4 °2θ, 13.7 °2θ, 14.6 °2θ, 15.2 °2θ, 17.7 °2θ, 19.0 °2θ, 20.2 °2θ, 20.9 °2θ, 21.1 °2θ, 21.6 °2θ, 22.7 °2θ, 23.3 °2θ, and 25.4 °2θ.

The Form N polymorph typically has an XRPD diffractogram in which the 10 most intense peaks include 5 or more (e.g. 6 or more, 7 or more, 8 or more, 9 or more, or 10) peaks which have an approximate 2θ value selected from: 5.0 °2θ, 5.4 °2θ, 5.8 °2θ, 6.3 °2θ, 7.3 °2θ, 10.7 °2θ, 11.3 °2θ, 12.4 °2θ, 13.7 °2θ, 14.6 °2θ, 15.2 °2θ, 17.7 °2θ, 19.0 °2θ, 20.2 °2θ, 20.9 °2θ, 21.1 °2θ, 21.6 °2θ, 22.7 °2θ, 23.3 °2θ, and 25.4 °2θ. More typically, the Form N polymorph has an XRPD diffractogram in which the 10 most intense peaks include 5 or more (e.g. 6 or more, 7 or more, 8 or more, 9 or more, or 10) peaks which have an approximate 2θ value selected from: 5.0 °2θ, 5.4 °2θ, 5.8 °2θ, 11.3 °2θ, 17.7 °2θ, 19.0 °2θ, 20.2 °2θ, 21.1 °2θ, 21.6 °2θ, and 22.7 °2θ.

The Form N polymorph may have an XRPD diffractogram approximately as set out in Table 14 below:

TABLE 14

| Form N | |
|---|---|
| Angle/°2θ | Intensity % |
| 5.0 | 100 |
| 5.4 | 18 |
| 5.8 | 43 |
| 6.3 | 14 |
| 7.3 | 11 |
| 10.7 | 11 |
| 11.3 | 14 |
| 12.4 | 8 |
| 13.7 | 8 |
| 14.6 | 8 |
| 15.2 | 11 |
| 17.7 | 20 |
| 19.0 | 17 |
| 20.2 | 41 |
| 20.9 | 13 |
| 21.1 | 15 |
| 21.6 | 19 |
| 22.7 | 21 |
| 23.3 | 12 |
| 25.4 | 13 |

Figure 22:
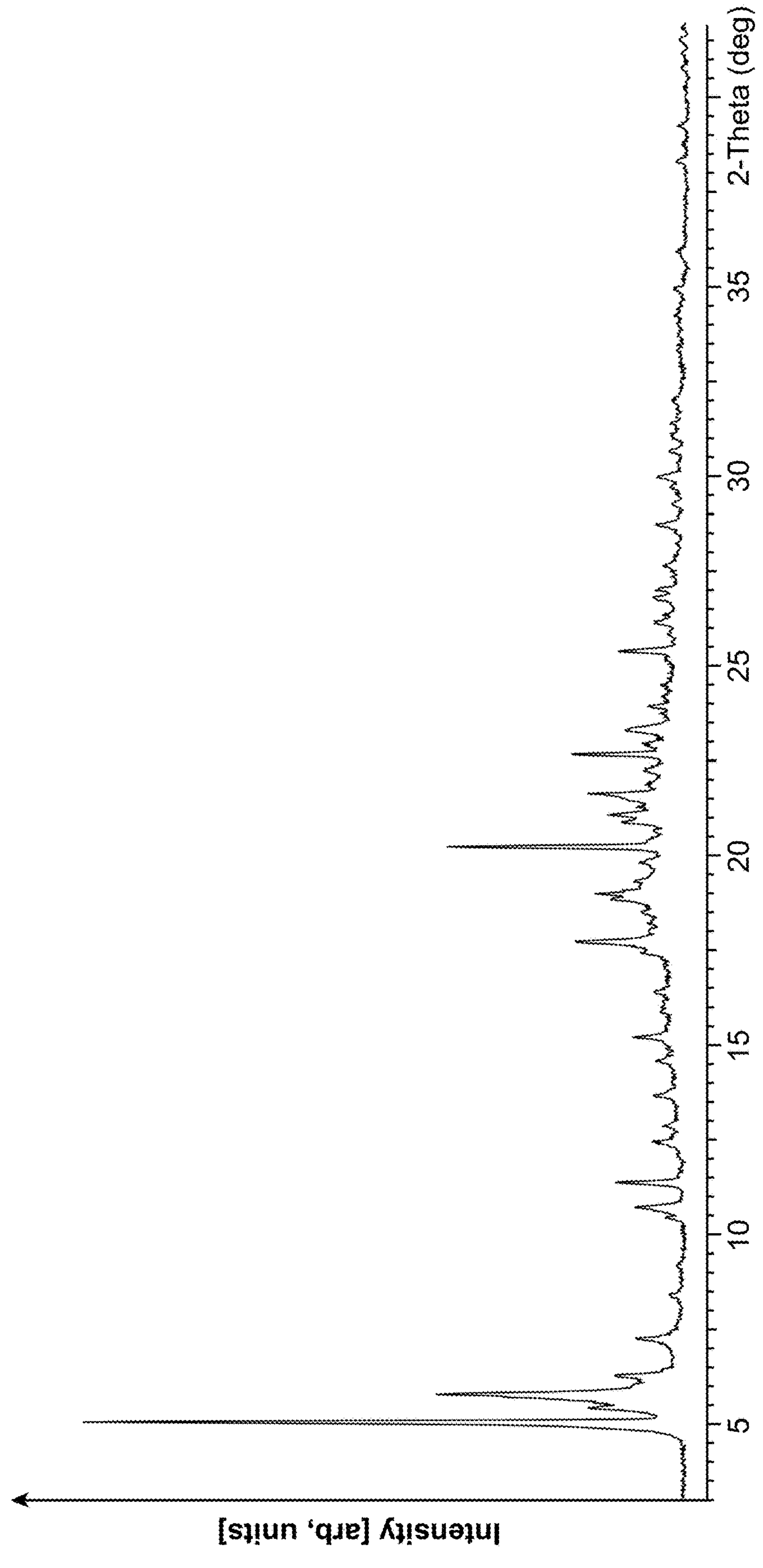
FIG. 22 shows an XRPD analysis of polymorphic Form N.

The Form N polymorph may have an XRPD diffractogram approximately as set out in FIG. 22.

The Form N polymorph is believed to be a dimethylsulfoxide (DMSO) solvate.

The Form N polymorph may be obtained by a process comprising:

(a) suspending 1-ethyl-N-((1,2,3,5,6,7-hexahydro-s-indacen-4-yl)carbamoyl)piperidine-4-sulfonamide monopotassium salt (preferably in Form A) in dimethylsulfoxide (DMSO) to form a suspension (preferably in a closed vessel); and (b) obtaining a crystalline monopotassium salt of 1-ethyl-N-((1,2,3,5,6,7-hexahydro-s-indacen-4-yl)carbamoyl) piperidine-4-sulfonamide as the Form N polymorph from the suspension.

In a preferred embodiment, in step (a), the suspension is kept at a temperature of about 15-25° C. (preferably about 23° C.) for about 1-15 days (preferably about 9 days), preferably in a closed vessel.

A third aspect of the present invention provides a pharmaceutical composition comprising a crystalline form of the first aspect of the invention or a polymorphic form of the second aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, 4$^{th}$ Ed., 2013. Pharmaceutically acceptable excipients including adjuvants, diluents or carriers that may be used in the pharmaceutical compositions of the invention, are those conventionally employed in the field of pharmaceutical formulation.

A fourth aspect of the invention provides a crystalline form of the first aspect of the invention, a polymorphic form of the second aspect of the invention, or a pharmaceutical composition of the third aspect of the invention, for use in medicine, and/or for use in the treatment or prevention of a disease, disorder or condition.

A fifth aspect of the invention provides the use of a crystalline form of the first aspect of the invention, a polymorphic form of the second aspect of the invention, or a pharmaceutical composition of the third aspect of the invention, in the manufacture of a medicament for the treatment or prevention of a disease, disorder or condition.

A sixth aspect of the invention provides a method of treatment or prevention of a disease, disorder or condition, the method comprising the step of administering an effective amount of a crystalline form of the first aspect of the invention, a polymorphic form of the second aspect of the invention, or a pharmaceutical composition of the third aspect of the invention, to thereby treat or prevent the disease, disorder or condition.

Typically, where the crystalline form of the first aspect of the invention, the polymorphic form of the second aspect of the invention, or the pharmaceutical composition of the third aspect of the invention is used in the treatment or prevention of a disease, disorder and condition, the crystalline form of the first aspect of the invention or the polymorphic form of the second aspect of the invention acts as an NLRP3 inhibitor.

In one embodiment, the disease, disorder or condition to be treated or prevented is selected from:

(i) inflammation;
(ii) an auto-immune disease;
(iii) cancer;
(iv) an infection;
(v) a central nervous system disease;
(vi) a metabolic disease;
(vii) a cardiovascular disease;
(viii) a respiratory disease;
(ix) a liver disease;
(x) a renal disease;
(xi) an ocular disease;
(xii) a skin disease;
(xiii) a lymphatic condition;
(xiv) a psychological disorder;
(xv) pain; and
(xvi) any disease where an individual has been determined to carry a germline or somatic non-silent mutation in NLRP3.

Typically, the treatment or prevention of the disease, disorder or condition comprises the administration of the crystalline form of the first aspect of the invention, the polymorphic form of the second aspect of the invention, or the pharmaceutical composition of the third aspect of the invention, to a subject.

A seventh aspect of the invention provides a method of inhibiting NLRP3, the method comprising the use of a crystalline form of the first aspect of the invention, a polymorphic form of the second aspect of the invention, or a pharmaceutical composition of the third aspect of the invention, to inhibit NLRP3. In one embodiment of the seventh aspect of the present invention, the method is performed ex vivo or in vitro.

Unless stated otherwise, in any of the fourth to seventh aspects of the invention, the subject may be a human or other animal. Typically, the subject is a mammal, more typically a human or a domesticated mammal such as a cow, pig, lamb, sheep, goat, horse, cat, dog, rabbit, mouse etc. Most typically, the subject is a human.

Any of the medicaments employed in the present invention can be administered by oral, parenteral (including intravenous, subcutaneous, intramuscular, intradermal, intratracheal, intraperitoneal, intraarticular, intracranial and epidural), airway (aerosol), rectal, vaginal or topical (including transdermal, buccal, mucosal and sublingual) administration.

Typically, the mode of administration selected is that most appropriate to the disorder, disease or condition to be treated or prevented.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

Examples

All solvents, reagents and compounds were purchased and used without further purification unless stated otherwise.

RH means relative humidity.

X-Ray Powder Diffraction (XRPD), Thermogravimetric Analysis (TGA), Thermogravimetric Analysis coupled to Fourier-Transform Infrared Spectroscopy (TGA-FTIR), and Differential Scanning calorimetry (DSC) techniques referred to in the examples were carried out under the following conditions:

High Resolution X-Ray Powder Diffraction (XRPD)

High resolution X-ray powder diffraction patterns were recorded in transmission geometry. X-ray diffraction patterns were recorded on a STOE STADI P diffractometer with CuKα1 radiation (1.5406 Å) at 20° C. and a Mythen position sensitive detector. The samples (approximately 10 to 50 mg) were prepared between thin polymer films and were usually analysed without further processing (e.g. grinding or sieving) of the substance.

Forms E, F, H, I, J, K, L, M and N were measured between two Kapton® films causing a typical broad reflection between 4.7 °2θ and 6.1 °2θ.

Thermogravimetric Analysis (TGA)

Thermogravimetric analyses were performed on a Mettler-Toledo thermogravimetric analyzer TGA/DSC1, TGA/DSC3+. For the thermogravimetric analyses, approximately 5 to 15 mg of sample were placed in aluminum pans, accurately weighed and hermetically closed with perforation lids. Prior to measurement, the perforation lids were automatically pierced resulting in approx. 0.5 mm pin holes. The samples were then heated under a flow of nitrogen of about 50 mL/min applying a heating rate of 5 K/min up to a maximum temperature of typically 350° C.

Thermogravimetric Analysis Coupled to Fourier-Transform Infrared Spectroscopy (TGA-FTIR)

Thermogravimetric analyses were performed on a Netzsch TG 209 F1 Libra coupled to a Bruker Vertex 70 IR spectrometer to analyse the evolving gas stream at the TGA outlet. For the thermogravimetric analyses, approximately 5 to 15 mg of sample were placed in aluminum pans, accurately weighed and hermetically closed with perforation lids. Prior to measurement, the perforation lids were automatically pierced resulting in approx. 0.5 mm pin holes. The samples were then heated under a flow of nitrogen of about 20 mL/min applying a heating rate of 10 K/min up to a maximum temperature of typically 200° C.

Differential Scanning calorimetry (DSC)

The DSC-thermograms were recorded using a Mettler-Toledo differential scanning calorimeter DSC2. For the measurements, approximately 2 to 6 mg of sample were placed in aluminum pans, accurately weighed and hermetically closed with perforation lids. Prior to measurement, the perforation lids were pierced resulting in approx. 0.5 mm pin holes. In order to measure the sample under pressure, closed lids can also be used. The samples were then heated under a flow of nitrogen of about 100 mL/min applying a heating rate of typically 1-20 K/min, usually 10 K/min to a maximum temperature of typically 180-350° C. (depending on decomposition temperature).

Figure 11:
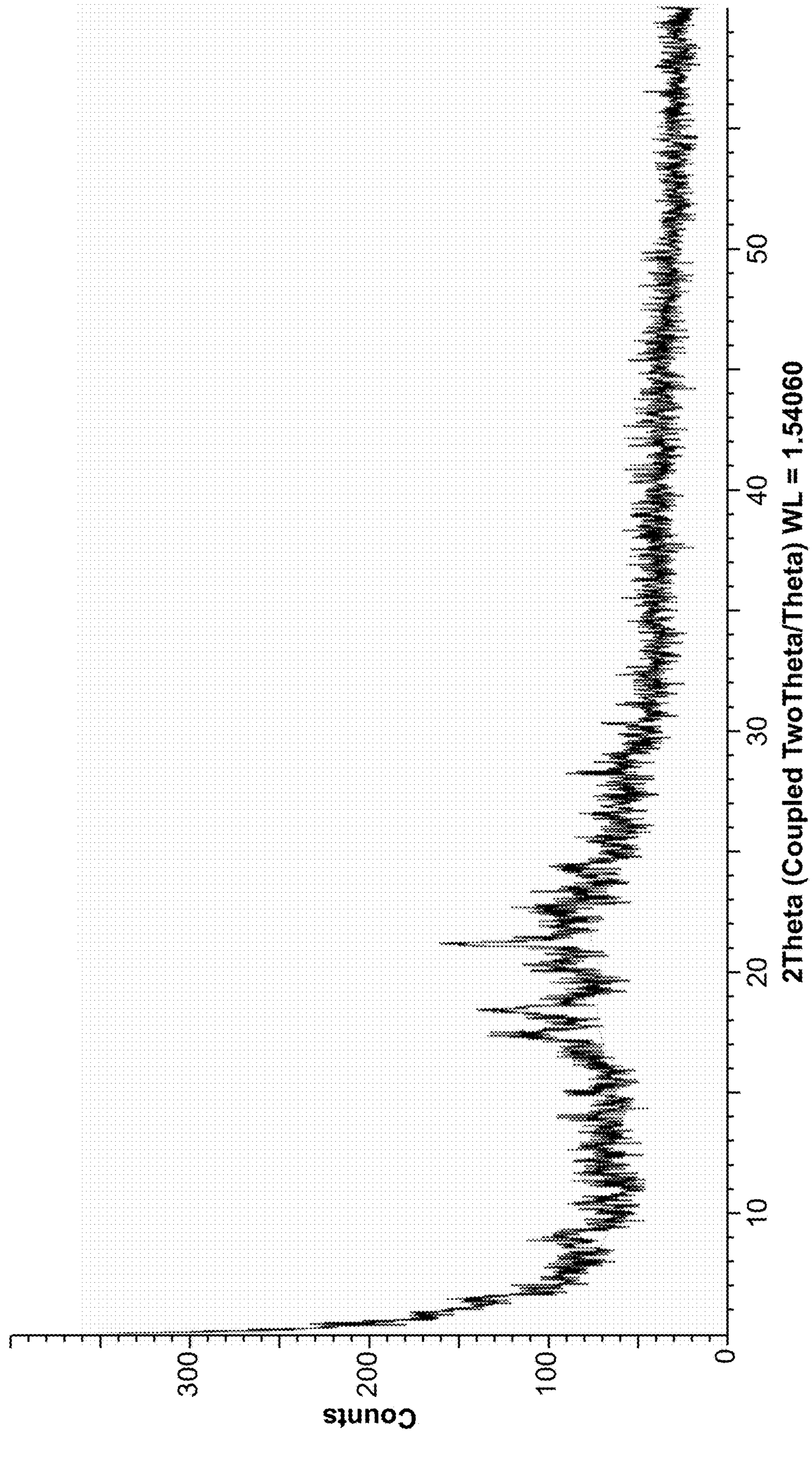
FIG. 11 shows an XRPD analysis of the amorphous product from comparative example 1.

Comparative Example 1: Amorphous 1-Ethyl-N-((1,2,3,5,6,7-hexahydro-s-indacen-4-yl)carbamoyl)piperidine-4-sulfonamide Monopotassium 1-Ethyl-N-((1,2,3,5,6,7-hexahydro-s-indacen-4-yl)carbamoyl)piperidine-4-sulfonamide monopotassium may be prepared as described in WO 2019/008025 (example 6). The procedure described for the preparation 1-ethyl-N-((1,2,3,5,6,7-hexahydro-s-indacen-4-yl)carbamoyl)piperidine-4-sulfonamide monopotassium in WO 2019/008025 (example 6) was repeated as described therein. Specifically, to a cooled (0° C.) solution of 1-ethylpiperidine-4-sulfonamide in THF was added potassium tert-butoxide. The ice bath was removed and the reaction mixture was stirred whilst being allowed to warm to room temperature over 40 minutes. A solution of 4-isocyanato-1,2,3,5,6,7-hexahydro-s-indacene in THF was added and the mixture was stirred overnight at room temperature. The reaction mixture was concentrated in vacuo and water was added. The suspension was filtered over cotton wool and subsequently submitted for purification by automated reversed phase column chromatography (using water for 5 minutes, followed by a gradual change over 25 minutes to water: MeOH in a ratio of 30:70) to afford 1-ethyl-N-((1,2,3,5,6,7-hexahydro-s-indacen-4-yl)carbamoyl)piperidine-4-sulfonamide monopotassium as a white solid, which was analysed by XRPD and found to be amorphous. The XRPD of the amorphous form is shown in FIG. 11.

Example 1: 1-Ethyl-N-((1,2,3,5,6,7-hexahydro-s-indacen-4-yl)carbamoyl)piperidine-4-sulfonamide Monopotassium Form A Portions of 1-ethyl-N-((1,2,3,5,6,7-hexahydro-s-indacen-4-yl)carbamoyl)piperidine-4-sulfonamide monopotassium (50 mg, 1 wt.) and the appropriate solvent (1000 μl, 20 vol.) listed in Table 15 were charged to separate vessels and stirred for 7 days at 20° C. After this time, the products were isolated by filtration, washed with recycled maturation solvent, dried under reduced pressure at 40° C. and analysed by XRPD.

TABLE 15

| No. | Solvent | Output form | Yield % |
|---|---|---|---|
| 1A | acetone | Form A | 57% |
| 1B | acetonitrile | Form A | 78% |
| 1C | anisole | Form A | 70% |
| 1D | t-butyl methyl ether | Form A | 36% |
| 1E | chlorobenzene | Form A | 67% |
| 1F | ethyl acetate | Form A | 61% |
| 1G | isopropyl acetate | Form A | 65% |
| 1H | methyl acetate | Form A | 73% |
| 1I | methylethyl ketone | Form A | 58% |
| 1J | 2-methyl tetrahydrofuran | Form A | 75% |

TABLE 15-continued

| No. | Solvent | Output form | Yield % |
|---|---|---|---|
| 1K | nitromethane | Form A | 83% |
| 1L | propionitrile | Form A | 63% |
| 1M | toluene | Form A | 55% |

The XRPD, TGA and DSC spectra for Form A are shown in FIGS. 1-3 respectively. Form A is anhydrous by DSC.

Example 2: 1-Ethyl-N-((1,2,3.5.6,7-hexahydro-s-indacen-4-yl)carbamovl)piperidine-4-sulfonamide Monopotassium Form A 1-Ethyl-N-((1,2,3,5,6,7-hexahydro-s-indacen-4-yl)carbamoyl)piperidine-4-sulfonamide monopotassium (14.71 Kg) was charged to a reaction vessel. Methanol (116.4 Kg) was charged to the vessel, the temperature was adjusted to 15 to 25° C. as required with stirring for 10 to 20 minutes (until a homogeneous cloudy solution with no lumps of solid present was formed). The solution was filtered through a 1 µm filter at 15 to 25° C. The filter was washed with methanol (11.3 Kg) at 15 to 25° C. The solution was concentrated to ca. 44 L at 25 to 35° C. Acetonitrile (116.6 Kg) was charged to the mixture and the solution was concentrated to ca. 74 L at 25 to 35° C. Acetonitrile (58.7 Kg) was charged to the mixture and the mixture was concentrated to ca. 74 L at ≤35° C. The mixture was analysed for residual methanol content by 1H NMR. Pass criterion ≤3.0% w/w methanol.

Acetonitrile (58.8 Kg) was charged to the vessel and the temperature was adjusted to 15 to 25° C. The slurry was aged for at least 1 hour (target 1 to 2 hours) at 15 to 25° C. and then filtered over 20 µm cloth at 15 to 25° C. The filter cake was twice washed with acetonitrile (23.9 Kg, 23.6 Kg) at 15 to 25° C.

The damp filter cake was analysed for residual phenol by HPLC. Pass criterion ≤0.20% area phenol. The solid was dried at up to 50° C. under a flow of nitrogen for at least 2 hours and analysed for residual water content using KF. Pass criterion ≤2.0% w/w water. Drying continued whilst the sample was being analysed.

The solid was analysed for residual acetonitrile by $^1$H NMR. Pass criterion ≤0.2% w/w MeCN. The solid was analysed for residual DMSO by $^1$H NMR. Pass criterion ≤0.4% w/w DMSO. The solid was analysed for residual solvent levels by GC. Pass criteria ≤3750 ppm DMSO, ≤2250 ppm MeOH and ≤308 ppm MeCN.

The product 1-ethyl-N-((1,2,3,5,6,7-hexahydro-s-indacen-4-yl)carbamoyl)piperidine-4-sulfonamide monopotassium Form A was obtained with:

Output: 14.42 Kg
Yield: 98%
HPLC purity: 99.5%

XRPD, TGA and DSC spectra similar to those in FIGS. 1-3 were observed.

Example 3: 1-Ethyl-N-((1,2,3.5,6,7-hexahydro-s-indacen-4-yl)carbamoyl)piperidine-4-sulfonamide Monopotassium Form D 1-Ethyl-N-((1,2,3,5,6,7-hexahydro-s-indacen-4-yl)carbamoyl)piperidine-4-sulfonamide monopotassium (75 mg, 1 wt.) was charged to a vial and methylethyl ketone was added (750 µl, 10 vol.). The suspension was heated on a hot plate set to 85° C. and water co-solvent (60 µl) was added until complete dissolution was achieved. The solution was cooled and left to stand undisturbed for 24 hours. The product 1-ethyl-N-((1,2,3,5,6,7-hexahydro-s-indacen-4-yl)carbamoyl)piperidine-4-sulfonamide monopotassium Form D was isolated by centrifugation and the pellets were oven dried under reduced pressure for 20 hours at 40° C., off-loaded and analysed by XRPD. Yield 56%.

The XRPD, TGA and DSC spectra for Form D are shown in FIGS. 4-6 respectively. Form D is a hydrate by DSC.

Example 4: 1-Ethyl-N-((1,2,3,5,6,7-hexahydro-s-indacen-4-yl)carbamoyl)piperidine-4-sulfonamide Monopotassium Form D 1-Ethyl-N-((1,2,3,5,6,7-hexahydro-s-indacen-4-yl)carbamoyl)piperidine-4-sulfonamide monopotassium (75 mg, 1 wt.) was charged to a vial and acetone was added (750 µl, 10 vol.). The suspension was heated on a hot plate set to 85° C. and water co-solvent (100 µl) was added until complete dissolution was achieved. The solution was cooled and left to stand undisturbed for 24 hours. The product 1-ethyl-N-((1,2,3,5,6,7-hexahydro-s-indacen-4-yl)carbamoyl)piperidine-4-sulfonamide monopotassium Form D was isolated by centrifugation and the pellets were oven dried under reduced pressure for 20 hours at 40° C., off-loaded and analysed by XRPD. Yield 46%.

XRPD, TGA and DSC spectra similar to those in FIGS. 4-6 were observed.

Example 5: 1-Ethyl-N-((1,2,3,5,6,7-hexahydro-s-indacen-4-yl)carbamoyl)piperidine-4-sulfonamide Monopotassium Form B 1-Ethyl-N-((1,2,3,5,6,7-hexahydro-s-indacen-4-yl)carbamoyl)piperidine-4-sulfonamide monopotassium (501.6 mg) was dissolved in methanol (4 mL) at ambient conditions. The hazy solution obtained was filtered through a 0.22 µm PVDF syringe filter and left for evaporation under stirring (100 rpm) at ambient conditions (~30% RH, 22° C.) until the solvent was evaporated to give 1-ethyl-N-((1,2,3,5,6,7-hexahydro-s-indacen-4-yl)carbamoyl)piperidine-4-sulfonamide monopotassium Form B.

The XRPD, TGA and DSC spectra for Form B are shown in FIGS. 7-9 respectively. Form B is a hydrate by TGA-FTIR.

Example 6: 1-Ethyl-N-((1,2,3,5,6,7-hexahydro-s-indacen-4-yl)carbamoyl)piperidine-4-sulfonamide Monopotassium Form C 1-Ethyl-N-((1,2,3,5,6,7-hexahydro-s-indacen-4-yl)carbamoyl)piperidine-4-sulfonamide monopotassium Form A (50 mg) was stored for 13 days at 100% RH in a closed vessel over pure water at 23° C. The resulting white solid was removed from the high humidity storage and immediately analysed by XRPD as 1-ethyl-N-((1,2,3,5,6,7-hexahydro-s-indacen-4-yl)carbamoyl)piperidine-4-sulfonamide monopotassium Form C.

The XRPD for Form C is shown in FIG. 12.

Example 7: 1-Ethyl-N-((1,2,3,5,6,7-hexahydro-s-indacen-4-yl)carbamoyl)piperidine-4-sulfonamide Monopotassium Form E 1-Ethyl-N-((1,2,3,5,6,7-hexahydro-s-indacen-4-yl)carbamoyl)piperidine-4-sulfonamide monopotassium Form A (500 mg) was suspended in acetonitrile/water 5/95 (v/v) (3 mL) for 6 days at 23° C. in a closed vessel. The white slurry was filtered and the resulting solid was analysed immediately by XRPD without further drying the resulting 1-ethyl-N-((1,2,3,5,6,7-hexahydro-s-indacen-4-yl)carbamoyl)piperidine-4-sulfonamide monopotassium Form E.

The XRPD for Form E is shown in FIG. 13.

Example 8: 1-Ethyl-N-((1,2,3,5,6,7-hexahydro-s-indacen-4-yl)carbamoyl)piperidine-4-sulfonamide Monopotassium Form F 1-Ethyl-N-((1,2,3,5,6,7-hexahydro-s-indacen-4-yl)carbamoyl)piperidine-4-sulfonamide monopotassium Form A (200 mg) was suspended in acetonitrile/water 95/5 (w/w) (2.6 g) for 3 days at 21° C. in a closed vessel. An aliquot of the white homogenous suspension was placed on a filter paper to remove the liquid phase. The solid material was analysed immediately by XRPD without further drying the resulting 1-ethyl-N-((1,2,3,5,6,7-hexahydro-s-indacen-4-yl) carbamoyl)piperidine-4-sulfonamide monopotassium Form F.

The XRPD for Form F is shown in FIG. 14.

Example 9: 1-Ethyl-N-((1,2,3.5,6,7-hexahydro-s-indacen-4-vl)carbamoyl)piperidine-4-sulfonamide Monopotassium Form G 1-Ethyl-N-((1,2,3,5,6,7-hexahydro-s-indacen-4-yl)carbamoyl)piperidine-4-sulfonamide monopotassium Form G was obtained by drying Form C at 0% RH at 23° C. for 5 days. The resulting white solid material was removed from the dry atmosphere and analysed immediately by XRPD as 1-ethyl-N-((1,2,3,5,6,7-hexahydro-s-indacen-4-yl)carbamoyl)piperidine-4-sulfonamide monopotassium Form G.

The XRPD for Form G is shown in FIG. 15.

Example 10: 1-Ethyl-N-((1,2,3,5,6,7-hexahydro-s-indacen-4-yl)carbamoyl)piperidine-4-sulfonamide Monopotassium Form H 1-Ethyl-N-((1,2,3,5,6,7-hexahydro-s-indacen-4-yl)carbamoyl)piperidine-4-sulfonamide monopotassium Form A (124 mg) was suspended in acetonitrile/water 85/15 (v/v) (0.5 mL) for 13 days at 23° C. in a closed vessel. The white slurry was filtered and the resulting solid was analysed immediately by XRPD without further drying the resulting 1-ethyl-N-((1,2,3,5,6,7-hexahydro-s-indacen-4-yl)carbamoyl)piperidine-4-sulfonamide monopotassium Form H.

The XRPD for Form H is shown in FIG. 16.

Example 11: 1-Ethyl-N-((1,2,3,5,6,7-hexahydro-s-indacen-4-yl)carbamoyl)piperidine-4-sulfonamide Monopotassium Form I 1-Ethyl-N-((1,2,3,5,6,7-hexahydro-s-indacen-4-yl)carbamoyl)piperidine-4-sulfonamide monopotassium Form A (100 mg) was suspended in n-propanol (1 mL) for 2 hours at 23° C. in a closed vessel. The white slurry was filtered and the resulting solid was analysed immediately by XRPD without further drying the resulting 1-ethyl-N-((1,2,3,5,6,7-hexahydro-s-indacen-4-yl)carbamoyl)piperidine-4-sulfonamide monopotassium Form I.

The XRPD for Form I is shown in FIG. 17.

Example 12: 1-Ethyl-N-((1,2,3,5,6,7-hexahydro-s-indacen-4-yl)carbamoyl)piperidine-4-sulfonamide Monopotassium Form J 1-Ethyl-N-((1,2,3,5,6,7-hexahydro-s-indacen-4-yl)carbamoyl)piperidine-4-sulfonamide monopotassium Form A (100 mg) was suspended in ethanol (1 mL) for 2 hours at 23° C. in a closed vessel. The white slurry was filtered and the resulting solid was analysed immediately by XRPD without further drying the resulting 1-ethyl-N-((1,2,3,5,6,7-hexahydro-s-indacen-4-yl)carbamoyl)piperidine-4-sulfonamide monopotassium Form J.

The XRPD for Form J is shown in FIG. 18.

Example 13: 1-Ethyl-N-((1,2,3,5,6,7-hexahydro-s-indacen-4-yl)carbamoyl)piperidine-4-sulfonamide Monopotassium Form K 1-Ethyl-N-((1,2,3,5,6,7-hexahydro-s-indacen-4-yl)carbamoyl)piperidine-4-sulfonamide monopotassium Form A (50 mg) was suspended in n-methyl-2-pyrrolidone (NMP) (0.1 mL) for 2 hours at 23° C. in a closed vessel. The white slurry was filtered and the resulting solid was analysed immediately by XRPD without further drying the resulting 1-ethyl-N-((1,2,3,5,6,7-hexahydro-s-indacen-4-yl)carbamoyl)piperidine-4-sulfonamide monopotassium Form K.

The XRPD for Form K is shown in FIG. 19.

Example 14: 1-Ethyl-N-((1,2,3,5,6,7-hexahydro-s-indacen-4-yl)carbamoyl)piperidine-4-sulfonamide Monopotassium Form L 1-Ethyl-N-((1,2,3,5,6,7-hexahydro-s-indacen-4-yl)carbamoyl)piperidine-4-sulfonamide monopotassium Form A (50 mg) was suspended in methanol (0.1 mL) for 2 hours at 23° C. in a closed vessel. The white slurry was filtered and the resulting solid was analysed immediately by XRPD without further drying the resulting 1-ethyl-N-((1,2,3,5,6,7-hexahydro-s-indacen-4-yl)carbamoyl)piperidine-4-sulfonamide monopotassium Form L.

The XRPD for Form L is shown in FIG. 20.

Example 15: 1-Ethyl-N-((1,2,3.5.6,7-hexahydro-s-indacen-4-yl)carbamoyl)piperidine-4-sulfonamide Monopotassium Form M 1-Ethyl-N-((1,2,3,5,6,7-hexahydro-s-indacen-4-yl)carbamoyl)piperidine-4-sulfonamide monopotassium Form A (100 mg) was suspended in dimethylformamide (DMF) (0.5 mL) for 9 days at 23° C. in a closed vessel. The initial white slurry turned into an unstirrable solid block of colourless crystals. The wet solid was analysed immediately by XRPD without further drying the resulting 1-ethyl-N-((1,2,3,5,6,7-hexahydro-s-indacen-4-yl)carbamoyl)piperidine-4-sulfonamide monopotassium Form M.

The XRPD for Form M is shown in FIG. 21.

Example 16: 1-Ethyl-N-((1,2,3,5,6,7-hexahydro-s-indacen-4-yl)carbamoyl)piperidine-4-sulfonamide Monopotassium Form N 1-Ethyl-N-((1,2,3,5,6,7-hexahydro-s-indacen-4-yl)carbamoyl)piperidine-4-sulfonamide monopotassium Form A (50 mg) was suspended in dimethylsulfoxide (DMSO) (0.1 mL) for 9 days at 23° C. in a closed vessel. The initial white slurry turned into an unstirrable solid block of colourless crystals. The wet solid was analysed immediately by XRPD without further drying the resulting 1-ethyl-N-((1,2,3,5,6,7-hexahydro-s-indacen-4-yl)carbamoyl)piperidine-4-sulfonamide monopotassium Form N.

The XRPD for Form N is shown in FIG. 22.

Evaluation Example 1: Competitive Suspension Equilibration

Form A (50 mg, 1 wt.) and Form D (amounts see Table 16) were charged to a vial and anhydrous acetonitrile (1000 µl, 20 vol.) was added. The vials were stirred at 20° C. or 40° C. for 96 hours.

TABLE 16

| No. | Temperature | Form D | Output form |
|---|---|---|---|
| 2A | 20° C. | 8.3 mg | Form A |
| 2B | 20° C. | 5.4 mg | Form A |
| 2C | 40° C. | 9.8 mg | Form A |
| 2D | 40° C. | 7.8 mg | Form A |

When stirred at 20° C. or 40° C. (refer to Table 16), complete turnover into a single form, Form A, was observed after 96 hours. This study shows that Form A is the more thermodynamically stable polymorphic form under these conditions.

Evaluation Example 2: Mechanical Grinding of Form A

Form A (50.4 mg) was ground for 24 hours. The product was recovered and analysed by XRPD to determine if any phase changes had occurred.

Figure 10:
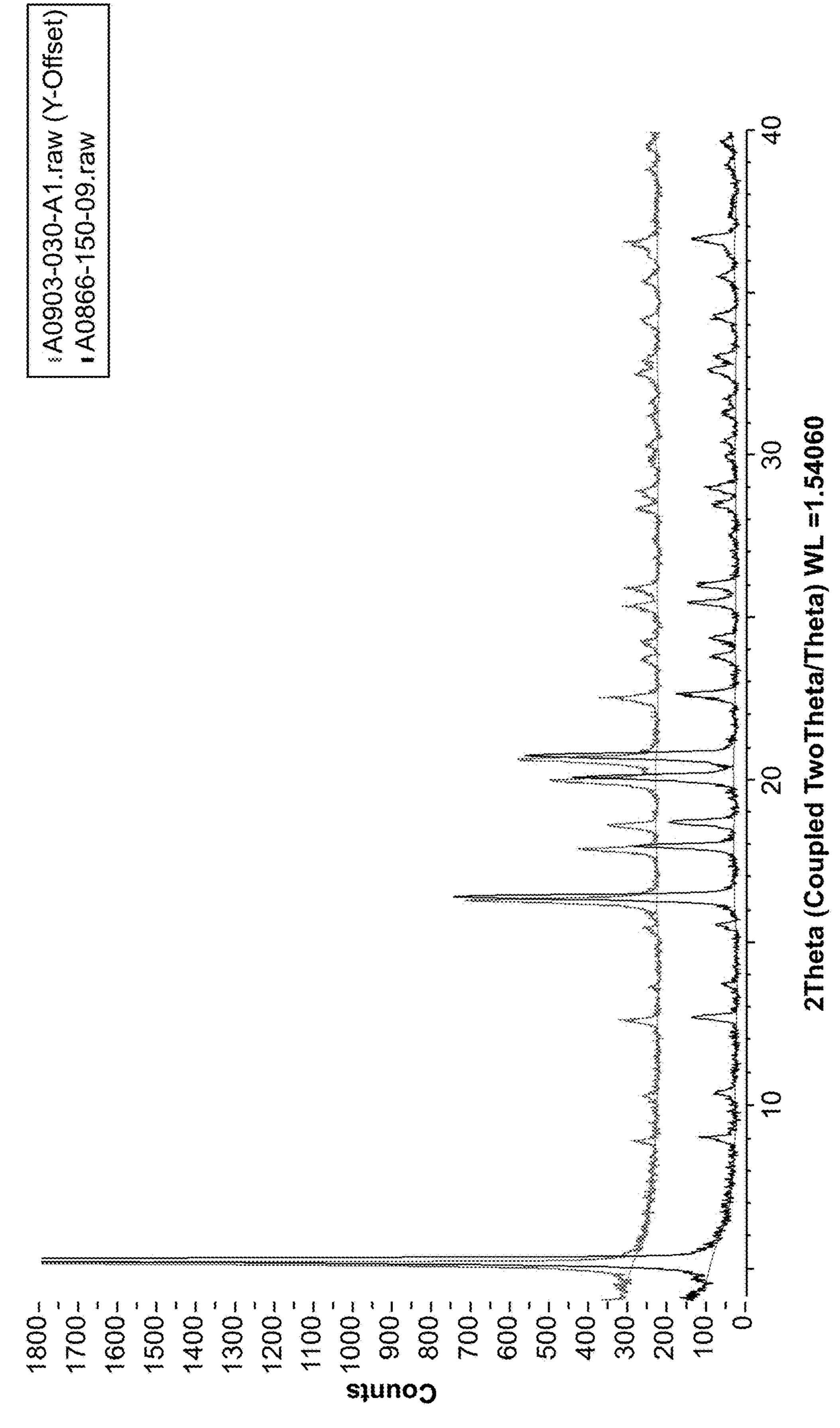
FIG. 10 shows an XRPD analysis of polymorphic Form A post-grinding treatment (upper diffractogram) overlaid with polymorphic Form A pre-grinding treatment (lower diffractogram) as described in evaluation example 2.

FIG. 10 shows the XRPD of Form A post-grinding treatment (upper diffractogram) overlaid with Form A pre-grinding treatment (lower diffractogram). As shown by FIG. 10, no significant change of polymorphic form was observed. This experiment shows that Form A is physically stable to prolonged grinding conditions.

Evaluation Example 3: Solubility Determinations

Crystalline 1-ethyl-N-((1,2,3,5,6,7-hexahydro-s-indacen-4-yl)carbamoyl)piperidine-4-sulfonamide salts (50 mg, 1 wt.) or crystalline 1-ethyl-N-((1,2,3,5,6,7-hexahydro-s-indacen-4-yl)carbamoyl)piperidine-4-sulfonamide free acid (as a control) (50 mg, 1 wt.) were stirred in purified water (1000 µl, 20 vol.) at 20° C. Limit solubilities (mg/ml) were determined after 48 hours at 20° C. measured by Q $^1$H NMR (measured against an internal standard, 2,3,5,6-tetrachloronitrobenzene).

TABLE 17

| | | | Limit solubilities (mg/ml) after 48 h at 20° C.; measured by Q $^1$H NMR | |
|---|---|---|---|---|
| No. | Salt form | Observation at 18 hours | 4-amino-indacene[1] (mg/ml) | Free acid form equivalent (mg/ml) |
| 3A | potassium | feint suspension | 0.0 | 38.0 |
| 3B | calcium | suspension | 0.0 | 6.3 |
| 3C | edisylate | white gum | 2.6 | 4.5 |
| 3D | succinate | suspension | 0.6 | 3.9 |
| 3E | hydrochloride | suspension | 0.8 | 3.3 |
| 3F | phosphate | suspension | 0.8 | 2.1 |
| 3G | acetate | suspension | 0.5 | 1.5 |
| 3H | free form | suspension | 0.0 | 0.6 |
| 3I | benzoate | suspension | 0.0 | 0.3 |
| 3J | zinc | suspension | 0.1 | 0.0 |

[1]Level of hydrolytic precursor measured in solution.

This study shows that the crystalline potassium salt exhibits the greatest solubility under these conditions and the least hydrolysis.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A polymorphic form of a crystalline monopotassium salt of 1-ethyl-N-((1,2,3,5,6,7-hexahydro-s-indacen-4-yl) carbamoyl) piperidine-4-sulfonamide, or a hydrate or solvate thereof having an XRPD diffractogram comprising peaks measured using CuK$\alpha_1$ radiation selected from the group consisting of:

(a) 5.14±0.2° 2θ, 16.30±0.2 °2θ, and 20.66±0.2° 2θ;

(b) 4.86±0.2° 2θ, 9.74±0.2° 2θ, 16.08±0.2° 2θ, and 19.16±0.2° 2θ; or (c) 4.90±0.2° 2θ, 6.60±0.2° 2θ, and 7.06±0.2° 2θ.

2. A polymorphic form of the salt of claim 1, having the XRPD diffractogram comprising peaks measured using CuK$\alpha_1$ radiation at 5.14±0.2° 2θ, 16.30±0.2° 2θ, and 20.66±0.2° 2θ.

3. A polymorphic form of the salt of claim 2, having an XRPD diffractogram in which the 10 most intense peaks measured using CuK$\alpha_1$ radiation include 5 or more peaks which have a 2θ value selected from:

4.14±0.2° 2θ, 8.90±0.2° 2θ, 12.60±0.2° 2θ, 16.30±0.2° 2θ, 17.86±0.2° 2θ, 18.60±0.2° 2θ, 20.00±0.2° 2θ, 20.66±0.2° 2θ, 22.54±0.2° 2θ, 23.70±0.2° 2θ, 24.26±0.2° 2θ, 25.36±0.2° 2θ, 25.90±0.2° 2θ, 28.90±0.2° 2θ, 30.30±0.2° 2θ, 32.50±0.2° 2θ, 32.92±0.2° 2θ, 35.40±0.2° 2θ, and 36.56±0.2° 2θ.

4. The polymorphic form of claim 2, having a TGA profile comprising weight loss of up to about 3% between 25° C. and 210° C.

5. The polymorphic form of claim 2, having a DSC profile comprising a single endothermic event having an onset at a temperature in a range from about 233° C. to about 241° C.

6. A process for preparing the polymorphic form of claim 2, comprising:

(a) suspending 1-ethyl-N-((1,2,3,5,6,7-hexahydro-s-indacen-4-yl) carbamoyl) piperidine-4-sulfonamide monopotassium salt in a solvent system to form a suspension; and (b) obtaining a crystalline monopotassium salt of 1-ethyl-N-((1,2,3,5,6,7-hexahydro-s-indacen-4-yl) carbamoyl) piperidine-4-sulfonamide as the polymorphic form from the suspension.

7. The process of claim 6, wherein the solvent system used in step (a) comprises a solvent selected from acetone, methylethyl ketone, acetonitrile, propionitrile, tert-butyl methyl ether, methyl acetate, ethyl acetate, isopropyl acetate, 2-methyl tetrahydrofuran, nitromethane, toluene, anisole, chlorobenzene, and mixtures thereof.

8. A polymorphic form of the salt of claim 1, having the XRPD diffractogram comprising peaks measured using CuK$\alpha_1$ radiation at 4.86±0.2° 2θ, 9.74±0.2° 2θ, 16.08±0.2° 2θ, and 19.16±0.2° 2θ.

9. A polymorphic form of the salt of claim 8, having an XRPD diffractogram in which the 10 most intense peaks measured using CuK$\alpha_1$ radiation include 5 or more peaks which have a 2θ value selected from:

3.86±0.2° 2θ, 8.42±0.2° 2θ, 9.74±0.2° 2θ, 12.76±0.2° 2θ, 14.64±0.2° 2θ, 16.08±0.2° 2θ, 16.94±0.2° 2θ, 17.62±0.2° 2θ, 19.16±0.2° 2θ, 19.46±0.2° 2θ, 20.06±0.2° 2θ, 20.98=0.2° 2θ, 24.52±0.2° 2θ, and 29.56±0.2° 2θ.

10. The polymorphic form of claim 8, having a TGA profile comprising weight loss of about 5.3% to about 7.3% between 25° C. and 160° C.

11. The polymorphic form of claim 8, having a DSC profile comprising a first broad endothermic event, an exothermic event having a first onset at a temperature in a range from about 143° C. to about 151° C. and a second onset at a temperature in a range from about 147° C. to about 155° C., and a second endothermic event having an onset at a temperature in a range from about 229° C. to about 237° C.

12. A process for preparing the polymorphic form of claim 8, comprising:

(a) suspending 1-ethyl-N-((1,2,3,5,6,7-hexahydro-s-indacen-4-yl) carbamoyl) piperidine-4-sulfonamide monopotassium salt in a solvent system comprising methylethyl ketone, tetrahydrofuran, acetone or a mixture thereof to form a suspension;

(b) adding water to the suspension to dissolve the 1-ethyl-N-((1,2,3,5,6,7-hexahydro-s-indacen-4-yl) carbamoyl) piperidine-4-sulfonamide monopotassium salt to form a solution; and (c) obtaining a crystalline monopotassium salt of 1-ethyl-N-((1,2,3,5,6,7-hexahydro-s-indacen-4-yl) carbamoyl) piperidine-4-sulfonamide as the polymorphic form from the solution.

13. A polymorphic form of the salt of claim 1, having the XRPD diffractogram comprising peaks measured using $CuK\alpha_1$ radiation at 4.90±0.2° 2θ, 6.60±0.2° 2θ, and 7.06±0.2° 2θ.

14. A polymorphic form of the salt of claim 13, having an XRPD diffractogram in which the 10 most intense peaks measured using $CuK\alpha_1$ radiation include 5 or more peaks which have a 2θ value selected from:

3.58±0.2° 2θ, 4.90±0.2° 2θ, 6.60±0.2° 2θ, 7.06±0.2° 2θ, 9.26±0.2° 2θ, 9.84±0.2° 2θ, 11.64±0.2° 2θ, 13.06±0.2° 2θ, 13.28±0.2° 2θ, 14.16±0.2° 2θ, 16.32±0.2° 2θ, 17.24±0.2° 2θ, 17.98±0.2° 2θ, 18.58±0.2° 2θ, 18.74±0.2° 2θ, 19.78±0.2° 2θ, 20.36=0.2° 2θ, and 21.36±0.2° 2θ.

15. The polymorphic form of claim 13, having a TGA profile comprising weight loss of about 9.9% to about 11.9% between 25° C. and 150° C.

16. The polymorphic form of claim 13, having a DSC profile comprising a triple endothermic event, followed by a weak exothermic event, followed by a weak endothermic event, followed by a broad endothermic event.

17. A process for preparing the polymorphic form of claim 13, comprising:

(a) providing 1-ethyl-N-((1,2,3,5,6,7-hexahydro-s-indacen-4-yl) carbamoyl) piperidine-4-sulfonamide monopotassium salt in methanol to form a mixture; and (b) obtaining a crystalline monopotassium salt of 1-ethyl-N-((1,2,3,5,6,7-hexahydro-s-indacen-4-yl) carbamoyl) piperidine-4-sulfonamide as the polymorphic form from the mixture.

18. A pharmaceutical composition comprising one or more of the crystalline salt forms of claim 1, and a pharmaceutically acceptable excipient.

19. A method of treatment of a disease, disorder or condition, the method comprising administering one or more of the crystalline salt forms of claim 1, wherein the disease, disorder or condition is responsive to NLRP3 inhibition.

20. A method of treatment of a disease, disorder or condition, the method comprising administering one or more of the crystalline salt forms of claim 1, wherein the disease, disorder or condition is selected from:

(i) inflammation;
(ii) an auto-immune disease;
(iii) cancer;
(iv) an infection;
(v) a central nervous system disease;
(vi) a metabolic disease;
(vii) a cardiovascular disease;
(viii) a respiratory disease;
(ix) a liver disease;
(x) a renal disease;
(xi) an ocular disease;
(xii) a skin disease;
(xiii) a lymphatic condition;
(xiv) a psychological disorder; and
(xv) pain.

21. A method of inhibiting NLRP3, the method comprising administering one or more of the crystalline salt forms of claim 1 to inhibit NLRP3.

* * * * *